US012674796B2

(12) United States Patent
Jackson et al.

(10) Patent No.: US 12,674,796 B2
(45) Date of Patent: Jul. 7, 2026

(54) SINGLE CELL PATHOLOGY ANALYSIS OF TUMOUR SAMPLES

(71) Applicant: UNIVERSITÄT ZÜRICH, Zürich (CH)

(72) Inventors: Hartland Jackson, Zurich (CH); Jana Fischer, Zurich (CH); Bernd Bodenmiller, Zurich (CH)

(73) Assignee: UNIVERSITÄT ZÜRICH, Zürich (CH)

( * ) Notice: Subject to any disclaimer, the term of this patent is extended or adjusted under 35 U.S.C. 154(b) by 703 days.

(21) Appl. No.: 17/866,587

(22) Filed: Jul. 18, 2022

(65) Prior Publication Data

US 2023/0016003 A1     Jan. 19, 2023

Related U.S. Application Data

(63) Continuation-in-part of application No. PCT/EP2021/050971, filed on Jan. 18, 2021.

(30) Foreign Application Priority Data

| | | | |
|---|---|---|---|
| Jan. 17, 2020 | (EP) | ...................................... | 20152569 |
| Jan. 20, 2020 | (EP) | ...................................... | 20152764 |
| Mar. 28, 2020 | (EP) | ...................................... | 20166533 |

(51) Int. Cl.
*G01N 33/57515*     (2026.01)
*G01N 33/50*     (2006.01)

(52) U.S. Cl.
CPC ... *G01N 33/5088* (2013.01); *G01N 33/57515* (2026.01)

(58) Field of Classification Search
CPC ................................................ G01N 33/57415
See application file for complete search history.

(56) References Cited

U.S. PATENT DOCUMENTS

| | | | |
|---|---|---|---|
| 2017/0010267 A1 * | 1/2017 | Liu | .................... G01N 33/5748 |
| 2019/0004037 A1 * | 1/2019 | Zhang | .................. G01N 33/574 |

FOREIGN PATENT DOCUMENTS

| | | | |
|---|---|---|---|
| WO | WO-2016141169 A1 * | 9/2016 | ........... A61K 31/335 |
| WO | 2018222979 | 12/2018 | |

OTHER PUBLICATIONS

Gerdtsson et al (Multiplex protein detection on circulating tumor cells from liquid biopsies using imaging mass cytometry, Converg Sci Phys Oncol. Mar. 2018 ; 4(1), pp. 1-18) (Year: 2018).*

Denis Schapiro et al, "histoCAT: analysis of cell phenotypes and interactions in multiplex image cytometry data", Nature Methods, vol. 14, No. 9, Sep. 1, 2017 (Sep. 1, 2017), p. 873-876.

Colomer R et al, "Biomarkers in breast cancer: A consensus statement by the Spanish Society of Medical Oncology and the Spanish Society of Pathology", Dec. 22, 2017 (Dec. 22, 2017), vol. 20, No. 7, p. 815-826.

Jackson Hartland W et al, "The single-cell pathology landscape of breast cancer", Jan. 20, 2020 (Jan. 20, 2020), vol. 578, No. 7796, p. 615-620.

Johanna Wagner et al, "A Single-Cell Atlas of the Tumor and Immune Ecosystem of Human Breast Cancer", Cell, vol. 177, May 16, 2019 (May 16, 2019), p. 1330-1345.

Si Qiu et al, "A single-cell immune atlas of triple negative breast cancer reveals novel immune cell subsets", Biorxiv,Jul. 5, 2019 (Jul. 5, 2019).

* cited by examiner

*Primary Examiner* — Nelson B Moseley, II
*Assistant Examiner* — Dennis J Sullivan
(74) *Attorney, Agent, or Firm* — JMB Davis Ben-David

(57) ABSTRACT

The invention relates to a method to indicate the clinical outcome of a cancer patient by labelling a cancer sample with labelled molecular probes, assaying the expression of a plurality of biomolecules at the resolution of a single cell and assigning a cellular identity (CI) to each single cell in the sample based on their expression pattern; then assigning a single cell pathology (SCP) patient group according to the proportion of each CI the sample contains.

The invention in other aspects relates to methods of treatment of a patient with anticancer drugs according to the patient's assignment to particular SCPs. Alternatively, this aspect may be formulated as the provision of certain drugs for treatment of cancer in patients characterized by tumours assigned to certain SCPs.

14 Claims, 35 Drawing Sheets

Tumour communities

Tumour communities

Average cells
per community

14. Hypoxic
15. Apoptotic
16. Proliferative
17. p53$^+$ EGFR$^+$
18. Basal CK
19. CK7$^+$ CK$^+$ Cadherin$^{hi}$
20. CK7$^+$ CK$^+$
21. Epithelial$^{low}$
22. CK$^{low}$ HR$^{low}$
23. CK$^+$ HR$^{hi}$
24. CK$^+$ HR$^+$
25. CK$^+$ HR$^{low}$
26. CK$^{low}$ HR$^{hi}$ p53$^+$
27. Myoepithelial Cellular Metacluster Immune
1. B Cell
2. T & B Cells
3. T Cell
4. Macrophage
5. T Cell
6. Macrophage Stromal
7. Endothelial
8. Vimentin$^{hi}$
9. Small Circular
10. Small Elongated
11. Fibronectin$^{hi}$
12. Large Elongated
13. SMA$^{hi}$Vimentin f   Microenvironment communities Average cells
per community Fig. 11 a (continues)
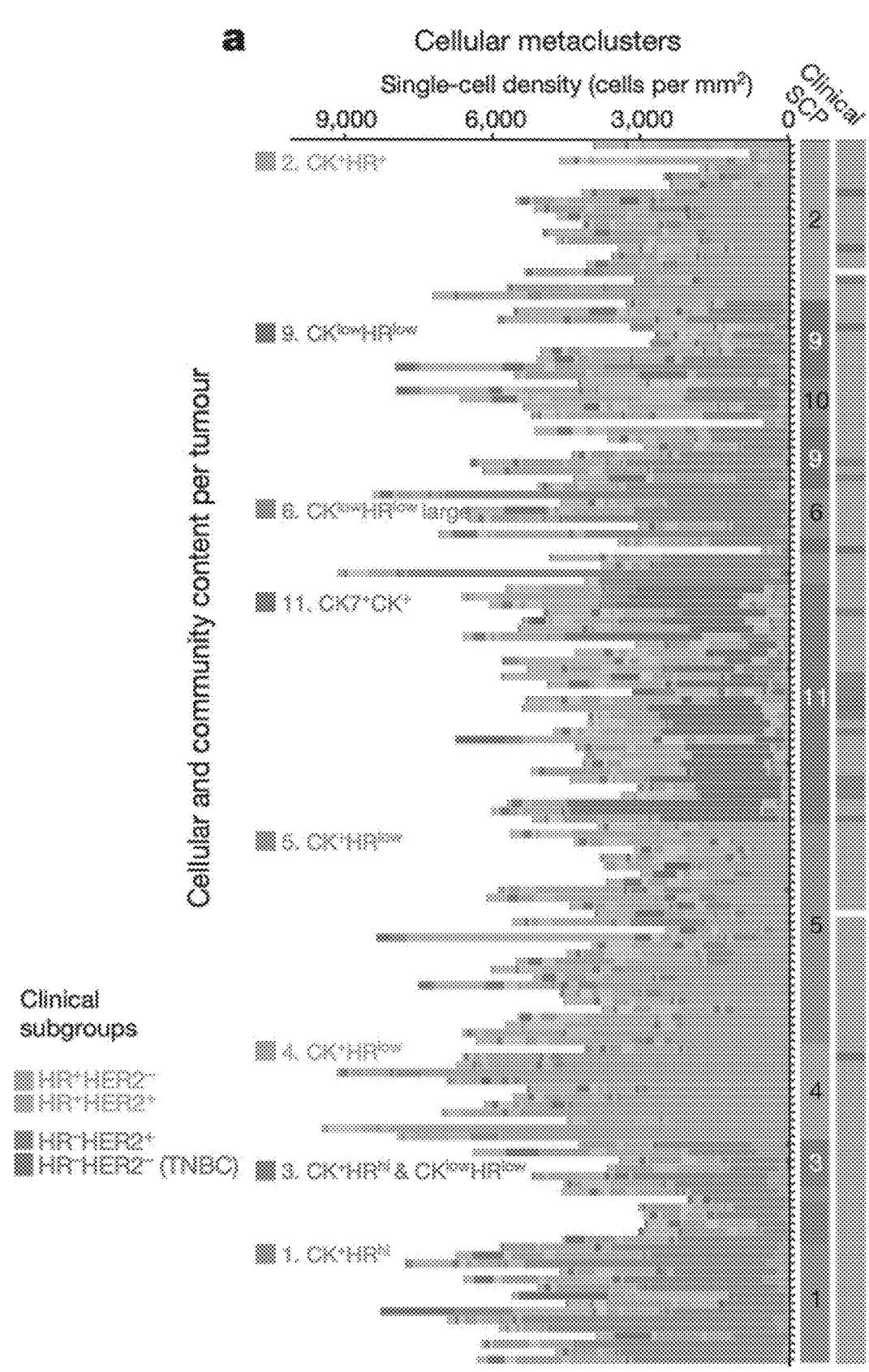

Fig. 16

| Metal Tag | Target | Antibody Clone | Company | Catalogue Number | Lot |
|---|---|---|---|---|---|
| In113 | Histone H3 | D1H2 | Cell Signaling | 4499BF | 12 |
| La139 | H3 (Lys28) trimethylate | C36B11 | Cell Signaling | 9733BF | 11 |
| Pr141 | Cytokeratin 5 | EP1601Y | Abcam | Custom | GR299320-I |
| Nd142 | Fibronectin | 10/Fibronectin | BD Biosciences | 610078 | 6251888 |
| Nd143 | Cytokeratin 19 | Troma-III | Dev Studies Hybridoma Bank | Troma -III | 2003-07-13 |
| Nd144 | Cytokeratin 8/18 | C51 | Cell Signaling | 4546BF | 2 |
| Nd145 | Twist | polyclonal_Twist1_ABD29 | Millipore | ABD29 | 2754704 |
| Nd146 | CD68 | KP1 | E-Bioscience | 14-0688-82 | E15987-105 |
| Sm147 | Keratin 14 (KRT14) | polyclonal_PA5-16722 | Thermo Fischer | PA5-16722 | SE2391461H |
| Nd148 | SMA | 1A4 | Abcam | ab7817 | 033M4768 |
| Sm149 | Vimentin | D21H3 | Cell Signaling | 5741BF | 3 |
| Nd150 | c-Myc | 9000000000 | Biolegend | 626802 | B201394 |
| Eu151 | c-erbB-2 - Her2 | 3B5 | BD Biosciences | 554299 | 6182799 |
| Sm152 | CD3 epsilon | D7A6E | Cell Signaling | 85061 | 2 |
| Eu153 | Histone H3 | HTA28 | Biolegend | 641002 | B200946 |
| Gd155 | Slug | 666633 | R&D Systems | Custom | CFZB021603A |
| Gd156 | Estrogen Receptor Alpha | EP1 | Epitomics | AC-0015EU | |
| Gd156 | Rabbit IgG (H+L) | polyclonal_AI-1000 | Vector Labs | AI-1000 | ZA0911 |
| Gd158 | Progesterone Receptor A/B | SP2 | Spring Bioscience | M3024 C | 131017 |
| Gd158 | Progesterone Receptor A/B | EP2 | Epitomics | AC-0028EU | |
| Tb159 | p53 | 7F5 | Cell Signaling | 2527BF | 5 |
| Gd160 | CD44 | polyclonal_CD44 | R&D Systems | AF3660 | CFOE0216011 |
| Dy162 | CD45 | 2B11 | E-Bioscience | 14-9457-82 | 4298126 |
| Dy163 | GATA3 | L50-823 | BD Biosciences | 558686 | 6132744 |
| Dy164 | CD20 | L26 | E-Bioscience | 14-0202-82 | 4285442 |
| Er166 | Carbonic Anhydrase IX | polyclonal_CAIX | R&D Systems | AF2188 | VNQ0215032 |
| Er167 | E-Cadherin / P-Cadherin | 36/E-Cadherin | BD Biosciences | 610182 | 6251878 |
| Er168 | Ki-67 | 8D5 | Cell Signaling | 9449BF | 2 |
| Tm169 | EGFR | D38B1 | Cell Signaling | 4267BF | 13 |
| Yb170 | p-S6 | D57.2.2E | Cell Signaling | 4858BF | 15 |

Fig. 16 (continued)

| | | | | |
|---|---|---|---|---|
| Yb172 | vWF | poly vwf | Millipore | AB7356 | 2700933 |
| Yb172 | CD31 | JC70A | Novus Biologicals | NB600-562 | B-1 |
| Yb173 | p-mTOR | 49F9 | Cell Signaling | 2976 | 11 |
| Yb174 | Cytokeratin 7 | RCK105 | BD Biosciences | 550507 | 6083676 |
| Lu175 | pan Cytokeratin | AE1 | Millipore | MAB1612 | 2341224 |
| Lu175 | pan Cytokeratin | AE3 | Millipore | MAB1611 | 2607604 |
| Yb176 | cleaved PARP | F21-852 | BD Biosciences | 552596 | 2150663 |
| Yb176 | Cleaved Caspase3 | C92-605 | BD Biosciences | 559565 | 6074683 |

Fig. 17
a)

Coxph Group vs All Others, n = 278, number of events = 56

| Single-Cell Pathology Patient Group | Nr. Patients | coef | exp(coef) | se(coef) | lower.95 | upper.95 | z | Pr(>\|z\|) |
|---|---|---|---|---|---|---|---|---|
| 1 CK$^+$ HR$^{hi}$ | 17 | -18.14 | 0.00 | 4029.00 | 0.00 | Inf | -0.01 | NA |
| 2 CK$^+$ HR$^+$ | 21 | -0.19 | 0.82 | 0.52 | 0.30 | 2.28 | -0.37 | 0.7090 |
| 3 CK$^+$ HR$^{hi}$ & CK$^{low}$ HR$^{low}$ | 20 | 0.41 | 1.51 | 0.41 | 0.68 | 3.35 | 1.02 | 0.3080 |
| 4 CK$^+$ HR$^{low}$ | 12 | 0.36 | 1.43 | 0.60 | 0.45 | 4.62 | 0.61 | 0.5450 |
| 5 CK$^+$ HR$^{low}$ mixed | 32 | -0.64 | 0.53 | 0.47 | 0.21 | 1.33 | -1.36 | 0.1750 |
| 6 CK$^{low}$ HR$^{low}$ | 10 | 0.86 | 2.37 | 0.52 | 0.86 | 6.57 | 1.66 | 0.0962 |
| 7 Epithelial$^{low}$ | 13 | 0.44 | 1.56 | 0.52 | 0.56 | 4.31 | 0.85 | 0.3940 |
| 8 Mixed | 11 | 1.46 | 4.30 | 0.43 | 1.84 | 10.06 | 3.37 | 0.0008 |
| 9 CK$^{low}$ HR$^{low}$ mixed | 20 | -0.21 | 0.81 | 0.59 | 0.25 | 2.59 | -0.36 | 0.7180 |
| 10 Epithelial$^{low}$ mixed | 24 | -0.32 | 0.73 | 0.52 | 0.26 | 2.01 | -0.61 | 0.5390 |
| 11 CK7$^+$ | 31 | -1.98 | 0.14 | 1.01 | 0.02 | 1.00 | -1.97 | 0.0495 |
| 12 CK7$^+$ CK$^{hi}$ E/P-Cadherin$^{hi}$ | 14 | 0.81 | 2.26 | 0.53 | 0.81 | 6.32 | 1.55 | 0.1210 |
| 13 Basal CK | 15 | 0.07 | 1.07 | 0.59 | 0.33 | 3.44 | 0.12 | 0.9040 |
| 14 Proliferative | 11 | 1.05 | 2.85 | 0.52 | 1.03 | 7.91 | 2.02 | 0.0439 |
| 15 EGFR$^+$ p53$^+$ | 8 | 0.50 | 1.65 | 1.01 | 0.23 | 11.98 | 0.49 | 0.6220 |
| 16 Apoptotic | 10 | -17.06 | 0.00 | 3663.00 | 0.00 | Inf | -0.01 | NA |
| 17 Hypoxic | 9 | 0.94 | 2.57 | 0.60 | 0.80 | 8.27 | 1.58 | 0.1140 |
| 18 CK HR$^{hi}$ p53$^+$ excluded | 3 | NA | NA | NA | NA | NA | NA | NA |

Single-Cell Pathology — Coxph Group vs Similar Groups

| Patient Groups | Nr. Patients | Nr. Events | coef | exp(coef) | se(coef) | lower .95 | upper .95 | z | Pr(>\|z\|) |
|---|---|---|---|---|---|---|---|---|---|
| 1 vs 2,3 | 58 | 11 | -19.57 | 0.00 | 8303.00 | 0.00 | Inf | 0.00 | NA |
| 3 vs 1,2 | 58 | 11 | 1.17 | 3.23 | 0.63 | 0.94 | 11.02 | 1.87 | 0.0618 |
| 16 vs 13,14,15,17 | 53 | 11 | -19.44 | 0.00 | 9088.00 | 0.00 | Inf | 0.00 | NA |
| 11 vs 12 | 45 | 5 | -2.62 | 0.07 | 1.14 | 0.01 | 0.68 | -2.30 | 0.0200 | c)

Single-Cell Pathology — Coxph within HR+HER2-, Group vs All Others, n = 173, number of events = 29

| Patient Group | Nr. Patients | coef | exp(coef) | se(coef) | lower .95 | upper .95 | z | Pr(>\|z\|) |
|---|---|---|---|---|---|---|---|---|---|
| 1 $CK^+$ $HR^{hi}$ | 15 | -18.17 | 0.00 | 5085.00 | 0.00 | Inf | 0.00 | NA |
| 2 $CK^+$ $HR^+$ | 10 | -17.11 | 0.00 | 3736.00 | 0.00 | Inf | -0.01 | NA |
| 3 $CK^+$ $HR^{hi}$ & $CK^{low}$ $HR^{low}$ | 18 | 0.52 | 1.69 | 0.49 | 0.64 | 4.44 | 1.06 | 0.2880 |
| 4 $CK^+$ $HR^{low}$ | 10 | 0.36 | 1.43 | 0.74 | 0.34 | 6.09 | 0.49 | 0.6270 |
| 5 $CK^+$ $HR^{low}$ mixed | 30 | -0.49 | 0.61 | 0.54 | 0.21 | 1.77 | -0.90 | 0.3660 |
| 6 $CK^{low}$ $HR^{low}$ | 8 | 1.04 | 2.83 | 0.61 | 0.85 | 9.37 | 1.70 | 0.0893 |
| 7 $Epithelial^{low}$ | 8 | 0.41 | 1.51 | 0.73 | 0.36 | 6.37 | 0.56 | 0.5750 |
| 8 mixed | 4 | 1.14 | 3.12 | 0.73 | 0.74 | 13.17 | 1.55 | 0.1210 |
| 9 $CK^{low}$ $HR^{low}$ mixed | 11 | -0.42 | 0.66 | 1.02 | 0.09 | 4.85 | -0.41 | 0.6820 |
| 10 $Epithelial^{low}$ mixed | 16 | -0.32 | 0.73 | 0.73 | 0.17 | 3.08 | -0.43 | 0.6670 |
| 11 $CK7^+$ | 19 | -18.21 | 0.00 | 4516.00 | 0.00 | Inf | 0.00 | NA |
| 12 $CK7^+$ $CK^{hi}$ E/P-Cadherin$^{hi}$ | 11 | 1.03 | 2.79 | 0.62 | 0.82 | 9.48 | 1.65 | 0.0996 |
| 13 Basal CK | 5 | 0.02 | 1.02 | 1.02 | 0.14 | 7.53 | 0.02 | 0.9840 |
| 14 Proliferative | 3 | 2.30 | 10.00 | 0.75 | 2.30 | 43.54 | 3.07 | 0.0022 |
| 15 $EGFR^+$ $p53^+$ | 0 | NA | NA | NA | NA | NA | NA | NA |
| 16 Apoptotic | 2 | -16.02 | 0.00 | 4880.00 | 0.00 | Inf | 0.00 | NA |
| 17 Hypoxic | 3 | 1.90 | 6.68 | 0.74 | 1.57 | 28.40 | 2.57 | 0.0101 |
| 18 CK $HR^{hi}$ $p53^+$ excluded | NA | NA | NA | NA | NA | NA | NA | NA |

| Single-Cell Pathology Patient Group | Logrank Group vs All Others | | | | | | | |
|---|---|---|---|---|---|---|---|---|
| | N | Observed | Expected | (O-E)^2/E | (O-E)^2/V | Chisq | DF | P |
| 1 CK+ HR^hi | 17 | 0 | 4.25 | 4.25 | 4.25 | | | |
| | 261 | 56 | 51.75 | 0.35 | 0.35 | 4.60 | 1 | 0.0300 |
| 2 CK+ HR+ | 21 | 4 | 4.78 | 0.13 | 0.14 | | | |
| | 257 | 52 | 51.22 | 0.01 | 0.14 | 0.10 | 1 | 0.7000 |
| 3 CK+ HR^hi & CK^low HR^low | 20 | 7 | 4.84 | 0.97 | 1.07 | | | |
| | 258 | 49 | 51.16 | 0.09 | 1.07 | 1.10 | 1 | 0.3000 |
| 4 CK+ HR^low | 12 | 3 | 2.14 | 0.35 | 0.36 | | | |
| | 266 | 53 | 53.86 | 0.01 | 0.36 | 0.40 | 1 | 0.5000 |
| 5 CK+ HR^low mixed | 32 | 5 | 8.70 | 1.57 | 1.90 | | | |
| | 246 | 51 | 47.30 | 0.29 | 1.90 | 1.90 | 1 | 0.2000 |
| 6 CK^low HR^low | 10 | 4 | 1.76 | 2.86 | 2.97 | | | |
| | 268 | 52 | 54.24 | 0.09 | 2.97 | 3.00 | 1 | 0.0800 |
| 7 Epithelial^low | 13 | 4 | 2.65 | 0.69 | 0.73 | | | |
| | 265 | 52 | 53.35 | 0.03 | 0.73 | 0.70 | 1 | 0.4000 |
| 8 mixed | 11 | 6 | 1.55 | 12.74 | 13.20 | | | |
| | 267 | 50 | 54.45 | 0.36 | 13.20 | 13.20 | 1 | 0.0003 |
| 9 CK^low HR^low mixed | 20 | 3 | 3.66 | 0.12 | 0.13 | | | |
| | 258 | 53 | 52.34 | 0.01 | 0.13 | 0.10 | 1 | 0.7000 |
| 10 Epithelial^low mixed | 24 | 4 | 5.36 | 0.34 | 0.38 | | | |
| | 254 | 52 | 50.64 | 0.03 | 0.38 | 0.40 | 1 | 0.5000 |
| 11 CK7+ | 31 | 1 | 6.51 | 4.67 | 5.31 | | | |
| | 247 | 55 | 49.49 | 0.61 | 5.31 | 5.30 | 1 | 0.0200 |
| 12 CK7+ CK20 E/P-Cadherin^hi | 14 | 4 | 1.87 | 2.42 | 2.54 | | | |
| | 264 | 52 | 54.13 | 0.08 | 2.54 | 2.50 | 1 | 0.1000 |
| 13 Basal CK | 15 | 3 | 2.80 | 0.01 | 0.02 | | | |
| | 263 | 53 | 53.20 | 0.00 | 0.02 | 0.00 | 1 | 0.9000 |
| 14 Proliferative | 11 | 4 | 1.47 | 4.34 | 4.49 | | | |
| | 267 | 52 | 54.53 | 0.12 | 4.49 | 4.50 | 1 | 0.0300 |
| 15 EGFR+ p53+ | 8 | 1 | 0.61 | 0.25 | 0.25 | | | |
| | 270 | 55 | 55.39 | 0.00 | 0.25 | 0.30 | 1 | 0.6000 |
| 16 Apoptotic | 10 | 0 | 1.83 | 1.83 | 1.91 | | | |
| | 268 | 56 | 54.17 | 0.06 | 1.91 | 1.90 | 1 | 0.2000 |
| 17 Hypoxic | 9 | 3 | 1.22 | 2.61 | 2.70 | | | |
| | 269 | 53 | 54.78 | 0.06 | 2.70 | 2.70 | 1 | 0.1000 |
| 18 CK- HR^hi p53+ excluded | NA | NA | NA | NA | NA | | | |
| | NA | NA | NA | NA | NA | NA | NA | NA | e)

| Single-Cell Pathology Patient Groups | Logrank Group vs Similar Groups | | | | | | | |
|---|---|---|---|---|---|---|---|---|
| | N | Observed | Expected | (O-E)^2/E | (O-E)^2/V | Chisq | DF | P |
| 1 vs | 17 | 0 | 3.23 | 3.23 | 4.58 | | | |
| 2,3 | 41 | 11 | 7.77 | 1.34 | 4.58 | 4.60 | 1 | 0.0300 |
| 3 vs | 20 | 7 | 3.87 | 2.52 | 3.91 | | | |
| 1,2 | 38 | 4 | 7.13 | 1.37 | 3.91 | 3.90 | 1 | 0.0500 |
| 16 vs | 10 | 0 | 2.56 | 2.56 | 3.36 | | | |
| 13,14,15,17 | 43 | 11 | 8.44 | 0.78 | 3.36 | 3.40 | 1 | 0.0700 |
| 11 vs | 31 | 1 | 3.79 | 2.05 | 8.67 | | | |
| 12 | 14 | 4 | 1.21 | 6.43 | 8.67 | 8.70 | 1 | 0.0030 |

| Single-Cell Pathology Patient Group | Logrank within HR+HER2-, Group vs All Others | | | | | | | |
|---|---|---|---|---|---|---|---|---|
| | N | Observed | Expected | (O-E)^2/E | (O-E)^2/V | Chisq | DF | P |
| 1 CK⁺ HRʰⁱ | 15 | 0 | 2.69 | 2.69 | 3.00 | | | |
| | 158 | 29 | 26.31 | 0.28 | 3.00 | 3.00 | 1 | 0.0800 |
| 2 CK⁺ HR⁺ | 10 | 0 | 1.80 | 1.80 | 1.93 | | | |
| | 163 | 29 | 27.20 | 0.12 | 1.93 | 1.90 | 1 | 0.2000 |
| 3 CK⁺ HRʰⁱ & CKˡᵒʷ HRˡᵒʷ | 18 | 5 | 3.19 | 1.03 | 1.17 | | | |
| | 155 | 24 | 25.81 | 0.13 | 1.17 | 1.20 | 1 | 0.3000 |
| 4 CK⁺ HRˡᵒʷ | 10 | 2 | 1.44 | 0.22 | 0.23 | | | |
| | 163 | 27 | 27.56 | 0.01 | 0.23 | 0.20 | 1 | 0.6000 |
| 5 CK⁺ HRˡᵒʷ mixed | 30 | 4 | 5.97 | 0.65 | 0.84 | | | |
| | 143 | 25 | 23.03 | 0.17 | 0.84 | 0.80 | 1 | 0.4000 |
| 6 CKˡᵒʷ HRˡᵒʷ | 8 | 3 | 1.14 | 3.04 | 3.19 | | | |
| | 165 | 26 | 27.86 | 0.12 | 3.19 | 3.20 | 1 | 0.0700 |
| 7 Epithelialˡᵒʷ | 8 | 2 | 1.73 | 0.29 | 0.31 | | | |
| | 165 | 27 | 27.63 | 0.01 | 0.31 | 0.30 | 1 | 0.6000 |
| 8 Mixed | 4 | 2 | 0.69 | 2.52 | 2.60 | | | |
| | 169 | 27 | 28.31 | 0.06 | 2.60 | 2.60 | 1 | 0.1000 |
| 9 CKˡᵒʷ HRˡᵒʷ mixed | 11 | 1 | 1.49 | 0.16 | 0.17 | | | |
| | 162 | 28 | 27.51 | 0.01 | 0.17 | 0.20 | 1 | 0.7000 |
| 10 Epithelialˡᵒʷ mixed | 16 | 2 | 2.68 | 0.17 | 0.19 | | | |
| | 157 | 27 | 26.32 | 0.02 | 0.19 | 0.20 | 1 | 0.7000 |
| 11 CK7⁺ | 19 | 0 | 3.47 | 3.47 | 3.97 | | | |
| | 154 | 29 | 25.53 | 0.47 | 3.97 | 4.00 | 1 | 0.0500 |
| 12 CK7⁺ CKʰⁱ E/P-Cadherinʰⁱ | 11 | 3 | 1.18 | 2.81 | 3.00 | | | |
| | 162 | 26 | 27.82 | 0.12 | 3.00 | 3.00 | 1 | 0.0800 |
| 13 Basal CK | 5 | 1 | 1.00 | 0.00 | 0.00 | | | |
| | 168 | 28 | 28.00 | 0.00 | 0.00 | 0.00 | 1 | 1.0000 |
| 14 Proliferative | 3 | 2 | 0.22 | 14.21 | 14.50 | | | |
| | 170 | 27 | 28.78 | 0.11 | 14.50 | 14.50 | 1 | 0.0001 |
| 15 EGFR⁺ p53⁺ | NA | NA | NA | NA | NA | | | |
| | NA | NA | NA | NA | NA | NA | NA | NA |
| 16 Apoptotic | 2 | 0 | 0.38 | 0.38 | 0.38 | | | |
| | 171 | 29 | 28.63 | 0.00 | 0.38 | 0.40 | 1 | 0.5000 |
| 17 Hypoxic | 3 | 2 | 0.32 | 8.75 | 8.90 | | | |
| | 170 | 27 | 28.68 | 0.10 | 8.90 | 8.90 | 1 | 0.0030 |
| 18 CK⁻ HRʰⁱ p53⁺ *excluded* | *NA* | *NA* | *NA* | *NA* | *NA* | | | |
| | *NA* | *NA* | *NA* | *NA* | *NA* | *NA* | *NA* | *NA* |

Fig. 18

Likelihood Ratio Tests

| | Coxph models | loglik | Chisq | DF | P(>\|Chi\|) |
|---|---|---|---|---|---|
| Model 1 | Clinical Subgroups | -267.30 | | | |
| Model 2 | Clinical Subgroups + Community Densities | -224.19 | 86.21 | 53.00 | 0.0026 |
| Model 1 | Clinical Subgroups + Grades | -260.20 | | | |
| Model 2 | Clinical Subgroups + Grades + Community Densities | -216.87 | 86.66 | 53.00 | 0.0024 |
| Model 1 | Grades | -262.85 | | | |
| Model 2 | Grades + Community Densities | -230.03 | 65.64 | 53.00 | 0.1140 |
| Model 1 | Grades | -262.85 | | | |
| Model 2 | Grades + Clinical Subgroups | -260.20 | 5.30 | 4.00 | 0.2576 |
| Model 1 | Clinical Subgroups | -284.31 | | | |
| Model 2 | Clinical Subgroups + Single-Cell Densities | -266.62 | 35.38 | 27.00 | 0.1295 |
| Model 1 | Clinical Subgroups + Grade | -278.78 | | | |
| Model 2 | Clinical Subgroups + Grade + Single-Cell Densities | -259.80 | 37.95 | 27.00 | 0.0787 |
| Model 1 | Clinical Subgroups | -278.37 | | | |
| Model 2 | Clinical Subgroups + SCP Groups | -260.36 | 36.02 | 16.00 | 0.0029 |
| Model 1 | Clinical Subgroups + Grade | -272.54 | | | |
| Model 2 | Clinical Subgroups + Grade + SCP Groups | -256.76 | 31.56 | 16.00 | 0.0114 |

Fig. 19

| SCP | Cellular features | Dominant Clinical subgroup | Outcome relative to clinical subgroup | Likely drug sensitivity |
|---|---|---|---|---|
| 1 | Some HR+HER2- cells, and >70% CK+ HR high cells | HR+HER2-/+ | good | hormone targeting SERM, SERD, aromatase inhibitors, and PI3K pathway inhibitors |
| 2 | mixed HER2, and >70% CK+ HR+ cells, | HR+HER2-/+ | intermediate | antiangiogenic, HER2-targeting |
| 3 | A mixture of CK low HR low cells, and ≤70% CK+ HR high cells | HR+HER2-/+ | poor | anti-proliferative e.g. anthracycline-type, mitotic inhibitor-type, antineoplastic platinum complex, alkylating, antimetabolite-type, and hormone targeting, e.g SERM, SERD, aromatase inhibitors, and PI3K pathway inhibitors |
| 4 | >70% CK+ HR low cells | HR+HER2-/+ | intermediate | lack of sensitivity to hormone targeting, e.g. SERM, SERD, aromatase inhibitors |
| 5 | ≤70% CK+ HR low cells | HR+HER2-/+ | intermediate | EZH2 methyltransferase inhibitor |
| 6 | Mixed HER2 and >80% CK low HR low cells, and large cell size | HR+HER2-/+ | poor | HER2-targeting |
| 7 | Mixed HER2, and >80% epithelial marker low cells | Variable | NA, variable clinical group | sensitivity to HER2-targeting, lack of sensitivity to antiangiogenics |
| 8 | ≤70% a mixture of CK low HR low cells, CK+ HR high cells, an CK+ HR low cells | Variable | NA, variable clinical group, but generally poor | None |
| 9 | mixed HER2 expression, 60-80% CK low HR low cells | HR+HER2-/+ | intermediate | HER2-targeting |
| 10 | Epithelial low cells, mixed HER2 and ≤70% a diverse mixture of CK low HR low cells, CK+ HR low cells , and few CK+ HR high cells | HR+HER2-/+ | intermediate | HER2-targeting |
| 11 | HR+ HER2+ cells, and >60% CK7+ CK+ cells, | HR+HER2- or HR-HER2+ | good | HER2 targeting, PI3K pathway inhibitor |
| 12 | H3K27me3+ cells, and >70% CK7+ CK high E-Cadherin high cells | HR+HER2-/+ | poor | EZH2 methyltransferase inhibitor |

Fig.   19 (continued)

| | | | | |
|---|---|---|---|---|
| 13 | Basal, mixed HER2 >50% CK7- CK+ HR- cells, + | Triple Negative | intermediate | HER2-targeting |
| 14 | >60% proliferative Ki67+ cells | Triple Negative | poor | anti-proliferative e.g anthracycline-type, mitotic inhibitor-type, antineoplastic platinum complex, alkylating, antimetabolite-type |
| 15 | >70% p53+ EGFR+ cells | Triple Negative | intermediate | anti-proliferative. e.g anthracycline-type, mitotic inhibitor-type, antineoplastic platinum complex, alkylating, antimetabolite-type, and inhibitors of EGFR |
| 16 | >50% apoptotic p53+ cPARP+ cells | Triple Negative | good | Anti-proliferative. e.g. anthracycline-type, mitotic inhibitor-type, antineoplastic platinum complex, alkylating, or antimetabolite-type |
| 17 | >50% CIAX high EGFR- cells | Triple Negative | poor | Hypoxia targeting e.g quinone-alkylating |
| 18 | HR+HER2- cells, >90% CK- HR+ p53+ cells, low ER | HR+HER2- | NA, small group size | lack of sensitivity to ER-targeting e.g. SERM, SERD, aromatase inhibitors, and sensitivity to PI3K pathway inhibitor |

SINGLE CELL PATHOLOGY ANALYSIS OF TUMOUR SAMPLES

CROSS-REFERENCE TO RELATED APPLICATIONS

This is a Continuation-in-Part of International Patent Application No. PCT/EP2021/050971, filed on Jan. 18, 2021, which in turn claimed priority to European Patent Application Nos. 20152569.8, filed on Jan. 17, 2020; 20152764.5, filed on Jan. 20, 2020; and 20166533.8, filed on Mar. 28, 2020. The contents of the foregoing applications are incorporated by reference herein in their entirety.

FIELD

The present invention relates to a method for analysis of a tumour tissue sample by multiplex staining of the sample with ligands, particularly antibodies, specific for cancer specific biomolecules at cellular level, and subsequent assignment to a likely clinical outcome. An analysis method of particular advantage for practicing the invention is imaging mass cytometry.

The invention further relates to the use of antineoplastic agents for treatment of cancer in patients assigned to specific groups by the methods of the invention.

BACKGROUND OF THE INVENTION

Histologic and phenotypic differences between tumours guide cancer diagnosis, prognosis, and selection of treatment. Currently, breast cancer patients are graded based on tumour structure and cellular morphology, and subcategorized when more than 1% of tumour cells contain hormone receptors or more than 10% express high levels of human epidermal growth factor receptor type 2 (HER2) or have amplified the HER2 gene. This leaves a large portion of cells uncharacterized even though additional molecular sub-classes and morphologic features have been identified as prognostic (Curtis et al., Nature 486, 346-352 (2012); Srlie et al; Proc Natl Acad Sci USA 98, 10869-10874 (2001); Nature 490, 61-70 (2012), Beck et al., Sci. Transl. Med. 3, 108ra113 (2011)).

Using highly multiplexed imaging, multiple complex cellular phenotypes have been identified within the context of the tumour microenvironment, enabling refined histopathology classification of clinical tissue samples http://f1000.com/work/citation?ids=4035995,5721524,6652259, 6862877&pre=&pre=&pre=&pre=&suf=&suf=&suf=&suf=&sa=0,0,0,0 (Schapiro et al.; Nat. Methods 14, 873-876 (2017); Keren et al.; Cell 174, 1373-1387.e19 (2018); Carvajal-Hausdorf et al., Clin. Cancer Res. 25, 3054-3062 (2019); Damond et al., Cell Metab. 29, 755-768.e5 (2019)).

Single-cell analyses have revealed extensive intra- and inter-patient heterogeneity between cancer tissue samples, but complex single-cell phenotypes and their spatial context are not yet reflected in the histologic stratification that is the foundation of clinical decisions.

Based on the above-mentioned state of the art, the objective of the present invention is to provide means and methods to identify multi-cellular features of the tumour microenvironment which can be used to stratify cancer patients, particularly breast cancer patients, into novel subgroups to provide more precise information on clinical outcome than the current histological subcatagories. This objective is attained by the subject-matter of the independent claims of the present specification.

SUMMARY OF THE INVENTION

A first aspect of the invention, relates to a method to classify a tumour according to morphological features, particularly to indicate the clinical outcome or drug sensitivity of a cancer patient, wherein the method comprises the steps of:

a. providing a cancer tissue sample obtained from the patient;

b. labelling the cancer tissue sample with a plurality of molecular probes, each probe being specific for a biomolecule, wherein each of said molecular probes is characterized by a detectable marker;

c. obtaining information about the expression of each of said plurality of biomolecules at the resolution of a single cell;

d. in a cell assignment step, assigning a cellular identity (CI) to each single cell in said labelled tissue sample based on the expression of said plurality of biomolecules, wherein the cellular identity is assigned as a function of the cell's expression of specific biomolecules;

e. in a pathology group assignment step, assigning said cancer tissue sample to a single cell pathology (SCP) patient group according to the proportion of each cellular identity assigned in the cell assignment step the sample contains.

The method according to the invention may comprise constructing of an image of the cancer tissue sample, for example as an output of the methods and/or systems described herein.

Furthermore, in particular embodiments, the method comprises the steps of f. partitioning the image of the cancer tissue sample into multicellular regions, wherein each single cell inside the multicellular region is highly interconnected to neighbouring cells to provide a cellular community;

g. assigning a cellular community identity (CCI) to each cellular community according to the number of cells in the cellular community, and the proportion of each CI it contains.

This aspect of the invention may further comprise the patient's assignment to a probable outcome group according to the type and number of cellular communities.

The invention in other aspects relates to methods of treatment of a patient with anticancer drugs according to the patient's assignment to particular SCPs. Alternatively, this aspect may be formulated as the provision of certain drugs for treatment of cancer in patients characterized by tumours assigned to certain SCPs.

While the inventors have demonstrated the extraordinary utility of the method and the wealth of information that can be obtained to inform treatment decisions for cancer patients, in a large cohort of breast cancer patients, the skilled artisan will recognize that the general methodology can be applied to a number of other cancer types, given appropriate clinical information.

DETAILED DESCRIPTION OF THE INVENTION

Terms and Definitions

For purposes of interpreting this specification, the following definitions will apply and whenever appropriate, terms used in the singular will also include the plural and vice versa. In the event that any definition set forth below conflicts with any document incorporated herein by reference, the definition set forth shall control.

The terms "comprising," "having," "containing," and "including," and other similar forms, and grammatical equivalents thereof, as used herein, are intended to be equivalent in meaning and to be open ended in that an item or items following any one of these words is not meant to be an exhaustive listing of such item or items, or meant to be limited to only the listed item or items. For example, an article "comprising" components A, B, and C can consist of (i.e., contain only) components A, B, and C, or can contain not only components A, B, and C but also one or more other components. As such, it is intended and understood that "comprises" and similar forms thereof, and grammatical equivalents thereof, include disclosure of embodiments of "consisting essentially of" or "consisting of."

Where a range of values is provided, it is understood that each intervening value, to the tenth of the unit of the lower limit, unless the context clearly dictate otherwise, between the upper and lower limit of that range and any other stated or intervening value in that stated range, is encompassed within the disclosure, subject to any specifically excluded limit in the stated range. Where the stated range includes one or both of the limits, ranges excluding either or both of those included limits are also included in the disclosure.

Reference to "about" a value or parameter herein includes (and describes) variations that are directed to that value or parameter per se. For example, description referring to "about X" includes description of "X."

As used herein, including in the appended claims, the singular forms "a," "or," and "the" include plural referents unless the context clearly dictates otherwise.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods (see generally, Sambrook et al., Molecular Cloning: A Laboratory Manual, 4th ed. (2012) Cold Spring Harbor Laboratory Press, Cold Spring Harbor, N.Y. and Ausubel et al., Short Protocols in Molecular Biology (2002) 5th Ed, John Wiley & Sons, Inc.) and chemical methods.

The term membrane-associated in the context of the present specification relates to molecules that are part of, or interact with biological membranes. Common examples include cluster of differentiation (CD) proteins, which are cell surface molecules used for the phenotyping of cells.

The terms gene expression or expression, or alternatively the term gene product, may refer to either of, or both of, the processes—and products thereof—of generation of nucleic acids (RNA) or the generation of a peptide or polypeptide, also referred to transcription and translation, respectively, or any of the intermediate processes that regulate the processing of genetic information to yield polypeptide products. The term gene expression may also be applied to the transcription and processing of a RNA gene product, for example a regulatory RNA or a structural (e.g. ribosomal) RNA. If an expressed polynucleotide is derived from genomic DNA, expression may include splicing of the mRNA in a eukaryotic cell. Expression may be assayed both on the level of transcription and translation, in other words mRNA and/or protein product.

In the present specification, the term positive, when used in the context of expression of a marker, refers to expression of an antigen assayed by a labelled (particularly fluorescently or isotope labelled) antibody, wherein the label's signal (fluorescence or other) on the structure (for example, a cell) referred to as "positive" is at least 30% higher ($\geq$30%), particularly $\geq$50% or $\geq$80%, in median signal (fluorescence or other) intensity in comparison to staining with an isotype-matched labelled antibody which does not specifically bind to the same target. Such expression of a marker is indicated by a superscript "plus" ($^+$), following the name of the marker, e.g. $CD4^+$, or by the addition of the plus sign after the marker name ("$CD4_+$"). If the word "expression" is used herein in the context of "gene expression" or "expression of a marker or biomolecule" and no further qualification of "expression" is mentioned, this implies "positive expression" as defined above.

In the present specification, the term negative, when used in the context of expression of a marker, refers to expression of an antigen, if assayed by a labelled (particularly fluorescently or isotope labelled) antibody, wherein the median label (fluorescence) intensity is less than 30% higher, particularly less than 15% higher, than the median label (fluorescence) intensity of an isotype-matched antibody which does not specifically bind the same target. Such expression of a marker is indicated by a superscript minus ($^-$), following the name of the marker, e.g. CD4-, or by the addition of the minus sign after the marker name ("CD4_").

High expression of a marker, for example high expression of hormone receptor (e.g progesterone or oestrogen receptors, HR), refers to the expression level of such marker in a clearly distinguishable cell population that is detected, for example by FACS, showing the highest signal intensity per cell compared to the other populations characterized by a lower signal intensity per cell. A high expression is indicated by superscript "high" or "hi" following the name of the marker, e.g. $HR^{high}$. The term "is expressed highly" refers to the same feature.

Low expression of a marker, for example low expression of HR, refers to the expression level of such marker in a clearly distinguishable cell population that is detected by FACS showing the lowest signal intensity per cell compared to the other populations characterized by higher signal intensity per cell. A low expression is indicated by superscript "low" or "lo" following the name of the marker, e.g. $HR^{low}$. The term "is expressed lowly" refers to the same feature.

The expression of a marker may be assayed via techniques such as fluorescence microscopy, flow cytometry, ELISPOT, ELISA or multiplex analyses. The current specification encompasses mass spectrometry cytometry as a particularly useful means of marker detection. Another particularly useful means of analysis encompassed herein is imaging mass spectrometry. An exemplary workflow of imaging mass cytometry (IMC) (see Giesen et al., Nature Methods, 2014 April; 11(4):417-22) comprises preparation of tissue sections for metal-chelated antibody labelling using IHC protocols. Then, tissue samples are positioned in a laser ablation chamber. The tissue is ablated and transported by a gas stream into a time of flight mass spectrometer, such as a CyTOF (Fluidigm) for mass cytometry analysis. The measured isotope signals are plotted using the coordinates of each single laser shot, and a multidimensional tissue image is generated. Single-cell features and marker expression are determined, allowing the investigation of cell subpopulation properties within the analysed tissue. Such features and images are, for example, one detail displayed as an output of the methods and/or systems described herein.

The term molecular probe in the context of the present specification relates to a specific ligand, particularly an antibody, antibody fragment, an antibody-like molecule or aptamer, more particularly an antibody or antibody fragment, that can bind to a target molecule, such as a specific surface protein or a specific transcription factor of a T cell with a dissociation constant of $\leq 10^{-7}$ mol/l, particularly $\leq 10^{-8}$ mol/l. The molecular probe comprises a detectable marker such as a particle, bead, dye or enzyme.

The term set of molecular probes relates to a panel of molecular probes for positive and/or negative selection of marker expression.

The term fluorescent dye in the context of the present specification relates to a small molecule capable of fluorescence in the visible or near infrared spectrum. Examples for fluorescent labels or labels presenting a visible color include, without being restricted to, fluorescein isothiocyanate (FITC), rhodamine, allophycocyanine (APC), peridinin chlorophyll (PerCP), phycoerithrin (PE), alexa Fluors (Life Technologies, Carlsbad, CA, USA), dylight fluors (Thermo Fisher Scientific, Waltham, MA, USA) ATTO Dyes (ATTO-TEC GmbH, Siegen, Germany), BODIPY Dyes (4,4-difluoro-4-bora-3a,4a-diaza-s-indacene based dyes) and the like.

The term aptamer relates an oligonucleotide or peptide molecule that binds to a specific target molecule. Aptamers can be created by selecting them from a large random sequence pool. Nucleic acid aptamers can be generated through repeated rounds of in-vitro selection or equivalently, SELEX (systematic evolution of ligands by exponential enrichment) to bind to molecular targets such as small molecules, proteins or nucleic acids through non-covalent interactions. Aptamers offer molecular recognition properties that rival that of antibodies.

The term specific binding in the context of the present invention refers to a property of ligands that bind to their target with a certain affinity and target specificity. The affinity of such a ligand is indicated by the dissociation constant of the ligand. A specifically reactive ligand has a dissociation constant of $\leq 10^{-7}$ mol/L when binding to its target, but a dissociation constant at least three orders of magnitude higher in its interaction with a molecule having a globally similar chemical composition as the target, but a different three-dimensional structure.

As used herein, the term treating or treatment of any disease or disorder (e.g. cancer) refers in one embodiment, to ameliorating the disease or disorder (e.g. slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. Methods for assessing treatment and/or prevention of disease are generally known in the art, unless specifically described hereinbelow.

The term device or system denotes an apparatus comprising one or more processors operable or operating according to one or more programs.

As used herein the term configured encompasses its plain and ordinary meaning. In one example, a device is configured to carry out a method by having software code for that method stored in a memory that is accessible to the processor(s) of the device. The processor(s) access the memory to implement the method. In another example, the instructions for carrying out the method are hard-wired into the processor(s). In yet another example, a portion of the instructions are hard-wired and a portion of them are stored as software code in the memory.

The term module refers to either a software module (e.g. code embodied on a machine-readable medium) or to a hardware module (e.g. a tangible unit capable of performing certain operations and can be configured or arranged in a certain physical manner).

The term output module refers to a hardware module that is configured to convey information to a user, for example by displaying said information. The output module may comprise a screen, a projector, a monitor, a printer, or an equally suited equipment for displaying said information. In certain embodiments, the output module is configured to display an image. In certain embodiments, the output module plots a graphical representation of the information received from the other modules of the system. The output module may comprise receiving and transmitting devices for communicating with other modules of the system. A first aspect of the invention relates to a method to characterise a cancer patient tumour sample according to single cell features. Particularly as part of a method to indicate a prognosis or a likelihood of clinical outcome of a cancer patient. The method of the invention is of particular advantage to patients bearing a hormone receptor expressing cancer, and of even more particular advantage to a breast cancer or ovarian cancer patient.

Certain aspects of the methods of the invention allow identification of breast cancer patients with different survival outcomes, or to assist a clinician to choose the most effective therapy for a particular tumour subtype.

In the most general terms, the method of the invention comprises the steps of:
  a. providing a cancer tissue sample obtained from the patient, the sample comprising cells.
    In many embodiments of the method of the invention, the sample will be in the form of a slide or histological preparation. The invention however encompasses embodiments wherein in an optional step, a single cell preparation is obtained from the cell sample and the information about cell type and subsequent analysis is performed on the single cell preparation.
  b. in a labelling step, the cancer tissue sample or the single cell preparation is labelled with a plurality of molecular probes. Each probe is specific for a biomolecule that could be present in the sample, or the absence of which is to be ascertained. The term "molecular probe" is used synonymously with "ligand bearing a unique detectable label", wherein the label may be for example an atom of distinct mass, or a dye of distinct spectroscopic quality. Probes may also be a nucleic acid sequence specific for an mRNA present in a cell. Each of said molecular probes is characterized by a detectable marker (primer, dye, isotope), thereby labelling the cells of the sample. This labelling step yields a labelled tissue sample.
    The biomolecules targeted by the probes in the labelling step are selected from a list comprising or consisting of
      i. epithelial cadherin (E-cadherin),
      ii. cytokeratin (CK) 18 and/or 19,
      iii. CK7,
      iv. oestrogen receptor (ER) and/or progesterone receptor (PR), v. a marker of cellular proliferation, particularly Ki-67 and/or PCNA, vi. CK5 and/or p63 and/or CK14, vii. p53, viii. a steroid sex hormone receptor (HR), particularly a receptor for oestrogen and/or progesterone (ER and PR, respectively), ix. a marker of apoptosis, particularly the cleaved form of poly ADP-ribose polymerase (cPARP) and/or the cleaved form of caspase3 (cC3) other markers of apoptosis, including but not restricted to annexin V or other permeability dyes are used in FACS, x. epidermal growth factor receptor (EGFR), xi. and a marker of hypoxia, particularly carbonic anhydrase (CAIX). Other markers may be HIF1a or oxygen sensing chemical probes.

Optionally, additional markers which may be used in this step include i. trimethylated H3K27, ii. phosphorylated ribosomal protein S6 (p-S6), iii. phosphorylated mechanistic target of rapamycin mTOR (p-mTOR), iv. human epidermal growth factor receptor 2 (HER2), v. c-myc, vi. histone 3 (H3), and/or vii. a marker of DNA content, particularly a DNA intercalating dye including but not limited to ethidium bromide, propidium iodide or the cyanine dimers CAS NO 169454-15-3, 169454-13-1, 143413-84-7.

Other markers useful in subsequent steps include: TWIST (Uniprot ID Q15672), SLUG (Uniprot ID 043623), placental cadherin (P-cadherin), GATA3, and SMA.

In certain embodiments, it is of advantage to acquire spatial parameters at this stage also, such as area, size, extent eccentricity, and the number of neighbouring or touching cells, defined as within 4 pixels, equivalent to around 4 uM.

In a subsequent reading step, information about the expression per cell of each of said plurality of biomolecules of the labelled tissue sample is obtained at the resolution of a single cell. Expression can be assessed in reference to the (mean) expression of a positive control tissue sample, in which the biomolecule in question is expressed, or relative to a negative control tissue sample, wherein the biomarker in question is not expressed (healthy tissue, or organ such as liver negative for hormone receptors, probe negative samples).

In certain embodiments, the classifications of negative, low, positive and high expression of said biomolecules in said cell reading step are classified relative to, or with reference to absolute measurements from reference samples comprising all biomolecules used in said classification step, particularly samples which have been previously assigned to SCP2, and SCP1 and/or SCP3, and SCP4 and/or SCP5, and SCP6, SCP9 and/or SCP10.

In a subsequent cell assignment step, a mutually exclusive cellular identity (CI) is assigned to essentially each single cell in said labelled tissue sample based on high-dimensional clustering analysis of the expression (or presence, in the case of DNA, or high expression or positive expression in the case of p53) of said plurality of biomolecules, wherein the cellular identity is assigned as a function of the cell's expression of biomolecules identified by markers according to the following list:

CI1: CIAX$^{hi}$, EGFR–, (ER and/or PR)+, (CK5 and/or p63 and/or CK14)+;

CI2. p53$^{hi}$, (cC3 and/or cPARP)+, (ER and/or PR)–, (CK18 and/or CK19)–, (CK5 and/or p63 and/or CK14)–;

CI3. (Ki-67 and/or PCNA)+, CK7–, (CK18 and/or CK19)–, (ER and/or PR)–, (CK5 and/or p63 and/or CK14)–;

CI4. p53$^{hi}$, EGFR+, CIAX$^{hi}$, (ER and/or PR)–, (CK5 and/or p63 and/or CK14)–;

CI5. (CK5 and/or p63 and/or CK14)+, CK7–, (CK18 and/or CK19)–, (ER and/or PR)–;

CI6. E-cadherin$^{hi}$, (CK18 and/or CK19)$^{hi}$, CK7+, (ER and/or PR)+, (CK5 and/or p63 and/or CK14)–;

CI7. CK7+, (CK18 and/or CK19)+, (ER and/or PR)–, (CK5 and/or p63 and/or CK14)–;

CI8. E-cadherin–, CK7–, (CK18 and/or CK19)–, (CK5 and/or p63 and/or CK14)–, (ER and/or PR)–;

CI9. (E-cadherin$^{lo}$ or E-cadherin–), ((CK18 and/or CK19)– or (CK18 and/or CK19)$^{lo}$) (ER and/or PR)$^{lo}$, (CK5 and/or p63 and/or CK14)–;

CI10. ((CK18 and/or CK19)$^{hi}$ or (CK18 and/or CK19)+), E-cadherin+, (ER and/or PR)$^{hi}$, CK5 and/or p63 and/or CK14)–;

CI11. ((CK18 and/or CK19)$^{hi}$ or (CK18 and/or CK19)+), E-cadherin+, (ER and/or PR)+, CK5 and/or p63 and/or CK14)–;

CI12. (E-cadherin$^{lo}$ or E-cadherin+), ((ER and/or PR)$^{lo}$ or (ER and/or PR)–), (CK5 and/or p63 and/or CK14)–;

CI13. p53$^{hi}$, EGFR+, (ER and/or PR)$^{hi}$, ((CK5 and/or p63 and/or CK14)$^{lo}$ and/or (CK5 and/or p63 and/or CK14)–);

CI14. CK7+, (CK18 and/or CK19)+, (CK5 and/or p63 and/or CK14)+, (ER and/or PR)–.

An alternative of the first aspect relates to a method for determining a plurality of cellular subpopulations within a tissue sample comprising the steps:

a. an acquisition step. In the acquisition step, data is acquired, or recorded from a labelled tissue sample. The data has local resolution of a single cell, meaning that the signal of one cell can be distinguished from the signal of another cell.

The labelled tissue sample is labelled with a plurality of molecular probes, each probe being specific for a biomolecule. Each of said molecular probes is characterized by a detectable marker. A signal of the detectable marker correlates with an amount of expression of the biomolecule. The biomolecules are selected from a list comprising:

i. epithelial cadherin (E-cadherin), ii. cytokeratin (CK) 18 and/or 19, iii. CK7, iv. oestrogen receptor (ER) and/or progesterone receptor (PR), v. a marker of cellular proliferation, particularly Ki-67 and/or PCNA, vi. CK5 and/or p63 and/or CK14, vii. p53, viii. a hormone receptor (HR), particularly a receptor for oestrogen and/or progesterone (ER and PR, respectively), ix. a marker of apoptosis, particularly the cleaved form of poly ADP-ribose polymerase (cPARP) and/or the cleaved form of caspase3 (cC3), x. epidermal growth factor receptor (EGFR), xi. a marker of hypoxia, particularly carbonic anhydrase (CAIX); and xii. a marker of DNA content, particularly a DNA intercalating dye;

b. an evaluation step. In the evaluation step, the data is processed such as to assign each detectable marker to an expression group selected from a high ($^{hi}$), a positive (+), a low ($^{lo}$), or a negative (−) expression level of the detectable marker in each cell comprised in the labelled tissue sample. The complex signal pattern acquired in the acquisition step is converted to four categories of a high ($^{hi}$), a positive (+), a low ($^{lo}$), or a negative (−) expression level for each recorded cell.

c. a cell assignment step. In the cell assignment step, each cell is assigned a cellular identity (CI), based on the assigned expression group, wherein the CI for each cell is selected from:

CI1: CIAX$^{hi}$, EGFR−, (ER and/or PR)+, (CK5 and/or p63 and/or CK14)+;

CI2. p53$^{hi}$, (cC3 and/or cPARP)+, (ER and/or PR)−, (CK18 and/or CK19)−, (CK5 and/or p63 and/or CK14)−;

CI3. (Ki-67 and/or PCNA)+, CK7−, (CK18 and/or CK19)−, (ER and/or PR)−, (CK5 and/or p63 and/or CK14)−;

CI4. p53$^{hi}$, EGFR+, CIAX$^{hi}$, (ER and/or PR)−, (CK5 and/or p63 and/or CK14)−;

CI5. (CK5 and/or p63 and/or CK14)+, CK7−, (CK18 and/or CK19)−, (ER and/or PR)−;

CI6. E-cadherin$^{hi}$, (CK18 and/or CK19)$^{hi}$, CK7+, (ER and/or PR)+, (CK5 and/or p63 and/or CK14)−;

CI7. CK7+, (CK18 and/or CK19)+, (ER and/or PR)−, (CK5 and/or p63 and/or CK14)−;

CI8. E-cadherin−, CK7−, (CK18 and/or CK19)−, (CK5 and/or p63 and/or CK14)−, (ER and/or PR)−;

CI9. (E-cadherin$^{lo}$ or E-cadherin−), ((CK18 and/or CK19)− or (CK18 and/or CK19)$^{lo}$), (ER and/or PR)$^{lo}$, (CK5 and/or p63 and/or CK14)−;

CI10. ((CK18 and/or CK19)$^{hi}$ or (CK18 and/or CK19)+), E-cadherin+, (ER and/or PR)$^{hi}$, CK5 and/or p63 and/or CK14)−;

CI11. ((CK18 and/or CK19)$^{hi}$ or (CK18 and/or CK19)+), E-cadherin+, (ER and/or PR)+, CK5 and/or p63 and/or CK14)−;

CI12. (E-cadherin$^{lo}$ or E-cadherin+), ((ER and/or PR)$^{lo}$ or (ER and/or PR)−), (CK5 and/or p63 and/or CK14)−;

CI13. p53$^{hi}$, EGFR+, (ER and/or PR)$^{hi}$, ((CK5 and/or p63 and/or CK14)$^{lo}$ and/or (CK5 and/or p63 and/or CK14)−);

CI14. CK7+, (CK18 and/or CK19)+, (CK5 and/or p63 and/or CK14)+, (ER and/or PR)−.

In certain embodiments, the tissue sample is a cancer tissue sample obtained from a patient. The clusters represent groups of cells that are similar to each other in the high-dimensional marker space.

In certain embodiments, the annotations of the clusters were based on the average marker expression of the clusters relative to each other. Some populations show comparatively low marker averages, for which most markers represents a population that is negative (only noise) and then there are other populations with comparatively high means which are considered positive. In these embodiments, in order to identify a group of cells as positive, there must be another group of cells that is negative/low for this marker. The differences between + and hi are more subtle, as they can only be distinguished if both populations are present, needing for example, a negative population and two different populations of positive cells where the mean of one positive cell population is higher than the other positive cell population.

Next, in a pathology group assignment step, said cancer tissue sample is assigned to a single cell pathology (SCP) patient group according to the proportion or frequency the sample contains of each cellular identity assigned in the cell assignment step, wherein the list of SCP patient groups comprises or consists of:

SCP1. >70% of single cells are CI10;

SCP2. >70% of single cells are CI11;

SCP3. ≤70% of single cells are CI10;

SCP4. wherein >70% of single cells to CI12;

SCP5. ≤70% of single cells are CI12;

SCP6. >80% of single cells are CI9;

SCP7. >80% of single cells are CI8;

SCP8. ≤70% of single cells are CI9; or CI10, or CI12;

SCP9. >60% of single cells are CI9;

SCP10. >70% of single cells are CI9; CI10, or CI12;

SCP11. >60% of single cells are CI7;

SCP12. >70% of single cells are CI6;

SCP13. >50% of single cells are CI5;

SCP14. >60% of single cells are CI3;

SCP15. >70% of single cells are CI4;

SCP16. >50% of single cells are CI2;

SCP17. >50% of single cells are CI1;

SCP18. >90% of single cells are CI14.

In certain embodiments, the cancer tissue sample comprises or essentially consists of neoplastic cells derived from a tissue characterised by expression of steroid hormone receptor expression, particularly neoplastic cells derived from breast, ovary or endometrial tissue, more particularly neoplastic cells derived from human breast or human mammary epithelium.

In certain embodiments, the method of obtaining information about the average expression of said plurality of biomolecules, and related described system, comprises constructing of an image of the cancer tissue sample, for example as an output of the method and/or system.

This can be achieved, for example, by immunohistochemistry employing dye-labelled ligands, or by a mass spectrometry based method including but not limited to imaging mass cytometry.

In certain embodiments, the cancer tissue sample is a section, particularly a histological slide.

In certain embodiments, the cancer tissue sample is a monolayer of adherent cells or cells otherwise immobilised on a solid surface.

In certain embodiments, the plurality of biomolecules is labelled by contacting the sample with a plurality of metal-conjugated or fluorescent dye-conjugated antibodies and/or nucleic acid probes.

In certain embodiments, the method of obtaining information about the average expression of said plurality of biomolecules is targeted imaging mass cytometry at a sub-cellular resolution, particularly at a resolution of ≤5 μm, or even ≤1 μm.

WO2015128490A1, incorporated herein by reference in its entirety, discloses subjecting multiple cells of the labelled tissue sample to laser ablation at multiple known locations using a laser spot size of 4 μm or less, to form a plurality of plumes; and subjecting plumes to inductively coupled plasma mass spectrometry, whereby detection of labelling atoms in the plumes permits construction of an image of the tissue sample.

In certain embodiments, the labelling step includes additional markers selected from:

CD3 or CD90, and

CD20 or CD19, and

CD68, and

CD44 and/or CD45, and fibronectin, and vimentin, and

CD31 and/or von Willibrand factor (vWF) and/or CD34.

In certain embodiments, in the cell assignment step, additional cellular identities are assigned as a function of the cell's expression of biomolecules identified by markers according to the following list:

CI15. CD44+, CD45+, (CD3 or CD90)+, fibronectin–, E-cadherin–, ((CK5 and/or p63 and/or CK14)$^{lo}$ or (CK5 and/or p63 and/or CK14)–);

CI16. CD20+, (fibronectin$^{lo}$ or fibronectin–), ((E-cadherin$^{lo}$ or E-cadherin–), ((CK5 and/or p63 and/or CK14)$^{lo}$ or (CK5 and/or p63 and/or CK14)–);

CI17. (CD3 or CD90)+, (CD20 or CD19)+;

CI18. CD68+;

CI19. vimentin+, (CD34 and/or VWF and/or CD31)+;

CI20. vimentin–, (fibronectin+ or fibronectin$^{hi}$), (CD3 or CD90)–, (CD20 or CD19)–, CD45–, CD44–.

In certain embodiments, the single cell image as used in the assignment of cellular identities is a fragment of the image of the cancer tissue sample. In certain particular embodiments, the single cell image is a fragment which consists of the pixels inside a region where membrane-associated molecules surround a single nucleus.

The single cell segmentation can be performed using the programs Ilastik and CellProfiler. Ilastik is used to train a pixel classifier to distinguish nuclear, membrane and background regions based on all markers. The resulting probability map (image where every pixel is assigned to one of the 3 categories) is then segmented into a single-cell mask (where every pixel is assigned to and individual cell) using CellProfiler, and is illustrative of the output generated by the methods and/or systems described herein.

In certain embodiments, said method comprises two steps that take into account the cellular community or network, in which an individual cell is situated. These steps are referred to as "cellular community detection step" and "cellular community assignment step" in the following.

In the cellular community detection step, the output image of the cancer tissue sample is partitioned into multicellular regions wherein each single cell inside the multicellular region is highly interconnected as determined by a suitable graph based community detection algorithm, for example the Louvain algorithm to neighbouring cells to provide a cellular community within close physical proximity, within 4 pixels/4 uM of the outermost pixel assigned to a cell. In certain particular embodiments, the single cells within said cellular communities are more sparsely connected to single cell regions from neighbouring cellular communities than to single cell regions within their own cellular community.

In the cellular community assignment step, assigning a cellular community identity (CCI) to each cellular community which is associated with a clinical outcome according to the number of cells in the cellular community, and the proportion of each CIit contains, wherein the list of CCI comprises or consists of:

CCI1. Among cells with identities CI1-CI14, >10% of single cells are CI6, and the average size of cellular communities is >25 cells (Hazard ratio good); or CCI2. Among cells with identities CI1-CI14, >10% of single cells are CI6, and the average size of cellular communities is ≤25 cells (Hazard ratio bad); or CCI3. Among cells with identities CI1-CI14, >10% of single cells are CI2, and the average size of cellular communities is >25 cells (Hazard ratio good); or CCI4. Among cells with identities CI1-CI14, >10% of single cells are CI2, and the average size of cellular communities is ≤25 cells (Hazard ratio bad); or CCI5. Among cells with identities CI1-CI14, >10% of cells are CI3, and the average size of cellular communities is ≤25 cells (Hazard ratio good), or CCI6. Among cells with identities CI1-CI14, >5% of cells are CI19, and >10% of cells are CI20, and >3% cells are CI18, and the average size of cellular communities is <50 cells (Hazard ratio bad); or CCI7. >80% of all cells are any of the identities CI1 to CI15, and <10% are CI20, and the average size of the cellular communities is <75 cells (Hazard ratio bad); or CCI8. >20% of all cells are CI15, and/or 16 and/or CI17, and <40% cells are any of the identities CI1 to CI14, and the average size of the cellular communities is more than 75 cells (Hazard ratio good; contains small fibroblasts (or pericytes) with compressed elongated nuclei); or CCI9. >5% of cells all are CI18, and the average size of the cellular communities is >25% (Hazard ratio good); or CCI10 >80% of all cells are any of the identities CI1 to CI14, and <2% cells are CI20, and the average size of the cellular communities is >115 cells and <125 cells (Hazard ratio good).

There can be many combinations of the CCI1 to 10 community definitions in a single patient sample (cell preparation, section, or output image of the sample. Not all such combinations will translate into a patient grouping, however patient outcomes can be linked to the presence or absence of these structures in specific settings, in the sense that increasing numbers of each community are associated with increased, or decreased hazard ratio.

In another aspect of the invention, SCP information, itself an illustrative output of the described methods and/or systems, is used to select the most appropriate treatment course for a patient with said survival outcome.

In certain embodiments, the patient is assigned to a probable outcome, or drug resistance specific to a SCP group according to the sample's classification in the pathology group assignment step:

SCP4 or SCP18: likely lack of sensitivity to antineoplastic drugs which target ER;

SCP7: likely lack of sensitivity to antiangiogenic antineoplastic drugs;

SCP1, SCP11: likely good outcome, a significantly better outcome compared to clinical HR+HER– groups, Logrank score P<0.05.

SCP8, SCP14, SCP17: likely bad outcome, Logrank score P<0.05 compared to all other SCP groups For the SCP linked to a good clinical outcome above, this may indicate either a Logrank score P<0.05 compared to clinical grouping, for example HR+HER– or HR+HER+, or to all other SCP groups. For the SCP linked to a bad clinical outcome above, this can indicate a Logrank score P<0.05 compared to all other SCP groups, or to HR+HER– or HR+HER+groups.

In particular embodiments, in the patient assignment step the patient is assigned to a probable outcome, or drug sensitivity group according to the sample's SCP classification in the pathology group assignment step:

SCP1, likely good outcome, and likely sensitive to a selective oestrogen receptor modulator (SERM) antineoplastic drug, particularly a SERM drug selected from raloxifene, toremifene and tamoxifen;

a selective estrogen receptor degraders (SERD) anti-neoplastic drug, particularly a SERD selected from fulvestrant, brilandestrant and elacestrant;

an aromatase inhibitor antineoplastic drug, particularly an aromatase inhibitor antineoplastic drug selected from exemestane, letrozole, vorozole, formestane, fadrozole and anastrozole; and/or a PI3K pathway inhibitor drug, particularly a PI3K pathway inhibitor drug selected from rapamycin, dactolisib, BGT226, SF1126, PKI-587, and NVPBE235SCP2;

SCP2, likely sensitive to an antiangiogenic antineoplastic drug, particularly an antiangiogenic antineoplastic drug selected from bevacizumab, thalidomide and lenalidomide; and/or a HER2 targeting antineoplastic drug, particularly a HER2 targeting antineoplastic drug selected from trastuzumab, pertuzumab, SYD985, RCI48, A166, HER2ALT-P7, T-DM1, ARX788, KN026, BVAC-B, MT-5111, AVX901, TAS0728, MP0274, MM-302, FS102, H2NVAC, HER2.taNK cells, HER2-pulsed dendritic cells, and HER2-targeting T cells;

SCP3, likely poor outcome, likely sensitive to an anthracycline-type antineoplastic drug, particularly an anthracycline-type antineoplastic drug selected from daunorubicin, doxorubicin, epirubicine, and idarubicin;

a mitotic inhibitor-type antineoplastic drug, particularly a mitotic inhibitor-type antineoplastic drug selected from capazitaxel, docetaxel, nab-paclitaxel, paclitaxel, vinblastine, vincristine, and vinorelbine;

an antineoplastic platinum complex, particularly an antineoplastic platinum complex selected from carboplatin, satraplatin, cisplatin, dicycloplatin, nedaplatin, oxaliplatin, picoplatin, triplatin, and tetranitrate;

an alkylating antineoplastic drug, particularly an alkylating antineoplastic drug selected from altretamine, bendamustine, busulfan, carboplatin, carmustine, cisplatin, cyclophosphamide, chlorambucil, dacarbayine, ifosfamide, lomustine, mechlorethamine, melphalan, oxaliplatin, temozolomide, thiptepa, and trabectedin;

an antimetabolite-type antineoplastic drug, particularly an antimetabolite-type antineoplastic drug selected from; azacytidine, 5-fluorouracil, 6-mercaptopurine, capecitabine, clofarabine, cytarabine, decitabine, floxuridine, fludarabine, gemcitabine, hydroxyurea, hydroxycarbamide, methotrexate, nelarabine, pemetrexed, pentostatin, pralatrexate, and phototrexate;

a selective SERM antineoplastic drug, particularly a SERM drug selected from raloxifene, toremifene and tamoxifen;

a SERD antineoplastic drug, particularly a SERD antineoplastic drug selected from fulvestrant, brilandestrant and elacestrant;

an aromatase inhibitor drug, particularly an aromatase inhibitor antineoplastic drug selected from exemestane, letrozole, vorozole, formestane, fadrozole and anastrozole; and/or a PI3K pathway inhibitor drug, particularly a PI3K pathway inhibitor drug selected from rapamycin, dactolisib, BGT226, SF1126, PKI-587, and NVPBE235;

SCP4, likely lack of sensitivity to antineoplastic drugs which target ER, particularly a SERM antineoplastic drug, more particularly a SERM drug selected from raloxifene, toremifene and tamoxifen;

a SERD antineoplastic drug, more particularly a SERD antineoplastic drug selected from fulvestrant, brilandestrant and elacestrant; and/or an aromatase inhibitor antineoplastic drug, particularly an aromatase inhibitor antineoplastic drug selected from exemestane, letrozole, vorozole, formestane, fadrozole and anastrozole;

SCP5, likely sensitive to an EZH2 methyltransferase inhibitor antineoplastic drug, particularly an EZH2 methyltransferase inhibitor antineoplastic drug selected from 3-deazaneplanocin A (DZNep), tazemetostat, EPZ005687, El1, GSK126, or UNCI99;

SCP6, likely poor outcome, likely sensitive a HER2 targeting antineoplastic drug, particularly a HER2 targeting antineoplastic drug selected from trastuzumab, pertuzumab, SYD985, RCI48, A166, HER2ALT-P7, T-DM1, ARX788, KN026, BVAC-B, MT-5111, AVX901, TAS0728, MP0274, MM-302, FS102, and H2NVAC;

SCP7, likely lack of sensitivity to an antiangiogenic antineoplastic drug, particularly an antiangiogenic antineoplastic drug selected from bevacizumab, thalidomide, and lenalidomide, and likely sensitive to a HER2 targeting antineoplastic drug, particularly a HER2 targeting antineoplastic drug selected from trastuzumab, pertuzumab, SYD985, RCI48, A166, HER2ALT-P7, T-DM1, ARX788, KN026, BVAC-B, MT-5111, AVX901, TAS0728, MP0274, MM-302, FS102, and H2NVAC;

SCP8, likely bad outcome;

SCP9, likely sensitive to a HER2 targeting antineoplastic drug, particularly a HER2 targeting antineoplastic drug selected from trastuzumab, pertuzumab, SYD985, RCI48, A166, HER2ALT-P7, T-DM1, ARX788, KN026, BVAC-B, MT-5111, AVX901, TAS0728, MP0274, MM-302, FS102, and H2NVAC;

SCP10, likely sensitive to a HER2 targeting antineoplastic drug, particularly a HER2 targeting antineoplastic drug selected from trastuzumab, pertuzumab, SYD985, RCI48, A166, HER2ALT-P7, T-DM1, ARX788, KN026, BVAC-B, MT-5111, AVX901, TAS0728, MP0274, MM-302, FS102, and H2NVAC;

SCP11: likely good outcome, and likely sensitive to a HER2 targeting antineoplastic drug, particularly a HER2 targeting antineoplastic drug selected from trastuzumab, pertuzumab, SYD985, RCI48, A166, HER2ALT-P7, T-DM1, ARX788, KN026, BVAC-B, MT-5111, AVX901, TAS0728, MP0274, MM-302, FS102, and H2NVAC, and/or a PI3K pathway inhibitor drug a PI3K pathway inhibitor drug, particularly a PI3K pathway inhibitor drug selected from rapamycin, dactolisib, BGT226, SF1126, PKI-587, and NVPBE235;

SCP12: likely poor outcome, likely sensitive to an EZH2 methyltransferase inhibitor antineoplastic drug, particularly an EZH2 methyltransferase inhibitor antineoplastic drug selected from 3-deazane-planocin A (DZNep), tazemetostat, EPZ005687, E11, GSK126, and UNCI99;

SCP13: likely sensitive to
  a HER2 targeting antineoplastic drug particularly a HER2 targeting antineoplastic drug selected from trastuzumab, pertuzumab, SYD985, RCI48, A166, HER2ALT-P7, T-DM1, ARX788, KN026, BVAC-B, MT-5111, AVX901, TAS0728, MP0274, MM-302, FS102, and H2NVAC;

SCP14: likely bad outcome, and likely sensitive to
  an anthracycline-type antineoplastic drug, particularly an anthracycline-type antineoplastic drug selected from daunorubicin, doxorubicin, epirubicine, and idarubicin;
  a mitotic inhibitor-type antineoplastic drug, particularly a mitotic inhibitor-type antineoplastic drug selected from capazitaxel, docetaxel, nab-paclitaxel, pacli-taxel, vinblastine, vincristine, and vinorelbine;
  an antineoplastic platinum complex, particularly an antineoplastic platinum complex selected from car-boplatin, satraplatin, cisplatin, dicycloplatin, nedaplatin, oxaliplatin, picoplatin, triplatin and tet-ranitrate;
  an alkylating antineoplastic drug, particularly an alky-lating antineoplastic drug selected from altretamine, bendamustine, busulfan, carboplatin, carmustine, cisplatin, cyclophosphamide, chlorambucil, dacar-bayine, ifosfamide, lomustine, mechlorethamine, melphalan, oxaliplatin, temozolomide, thiptepa, and trabectedin; and/or
  an antimetabolite-type antineoplastic drug, particularly an antimetabolite-type antineoplastic drug selected from; azacytidine, 5-fluorouracil, 6-mercaptopurine, capecitabine, clofarabine, cytarabine, decitabine, floxuridine, fludarabine, gemcitabine, hydroxyurea, hydroxycarbamide, methotrexate, nelarabine, pem-etrexed, pentostatin, pralatrexate, and phototrexate;

SCP15: likely sensitive to
  an anthracycline-type antineoplastic drug, particularly an anthracycline-type antineoplastic drug selected from daunorubicin, doxorubicin, epirubicine, and idarubicin;
  a mitotic inhibitor-type antineoplastic drug, particularly a mitotic inhibitor-type antineoplastic drug selected from capazitaxel, docetaxel, nab-paclitaxel, pacli-taxel, vinblastine, vincristine, and vinorelbine;
  an antineoplastic platinum complex, particularly an antineoplastic platinum complex selected from car-boplatin, satraplatin, cisplatin, dicycloplatin, nedaplatin, oxaliplatin, picoplatin, triplatin and tet-ranitrate;
  an alkylating antineoplastic drug, particularly an alky-lating antineoplastic drug selected from altretamine, bendamustine, busulfan, carboplatin, carmustine, cisplatin, cyclophosphamide, chlorambucil, dacar-bayine, ifosfamide, lomustine, mechlorethamine, melphalan, oxaliplatin, temozolomide, thiptepa, and trabectedin;
  an antimetabolite-type antineoplastic drug, particularly an antimetabolite-type antineoplastic drug selected from; azacytidine, 5-fluorouracil, 6-mercaptopurine, capecitabine, clofarabine, cytarabine, decitabine, floxuridine, fludarabine, gemcitabine, hydroxyurea, hydroxycarbamide, methotrexate, nelarabine, pem-etrexed, pentostatin, pralatrexate, and phototrexate; and/or an inhibitor of EGFR bioactivity antineoplastic drug, particularly an inhibitor of EGFR bioactivity antine-oplastic drug selected from gefetinib, erlotinib, lapa-tinib, cetuxumib, neratinib, osimeratib, panituma-mib, vandetanib, necitumumab, and dacomitinib;

SCP16: likely good outcome, likely sensitive to
  an anthracycline-type antineoplastic drug, particularly an anthracycline-type antineoplastic drug selected from daunorubicin, doxorubicin, epirubicine, idaru-bicin;
  a mitotic inhibitor-type antineoplastic drug, particularly a mitotic inhibitor-type antineoplastic drug selected from capazitaxel, docetaxel, nab-paclitaxel, pacli-taxel, vinblastine, vincristine, and vinorelbine;
  an antineoplastic platinum complex, particularly an antineoplastic platinum complex selected from car-boplatin, satraplatin, cisplatin, dicycloplatin, nedaplatin, oxaliplatin, picoplatin, triplatin, and tet-ranitrate;
  an alkylating antineoplastic drug, particularly an alky-lating antineoplastic drug selected from altretamine, bendamustine, busulfan, carboplatin, carmustine, cisplatin, cyclophosphamide, chlorambucil, dacar-bayine, ifosfamide, lomustine, mechlorethamine, melphalan, oxaliplatin, temozolomide, thiptepa, or trabectedin; or
  an antimetabolite-type antineoplastic drug, particularly an antimetabolite-type antineoplastic drug selected from azacytidine, 5-fluorouracil, 6-mercaptopurine, capecitabine, clofarabine, cytarabine, decitabine, floxuridine, fludarabine, gemcitabine, hydroxyurea, hydroxycarbamide, methotrexate, nelarabine, pem-etrexed, pentostatin, pralatrexate, or phototrexate;

SCP17: likely bad outcome, and likely sensitive to
  a quinone-alkylating antineoplastic drug, particularly the quinone-alkylating antineoplastic drug mitomy-cin C;

SCP18: likely lack of sensitivity to antineoplastic drugs which target ER, particularly
  a SERM antineoplastic drug, more particularly a SERM drug selected from raloxifene, toremifene or tamoxifen;
  a SERD antineoplastic drug, more particularly fulves-trant, brilandestrant and elacestrant; and/or
  an aromatase inhibitor antineoplastic drug, particularly an aromatase inhibitor antineoplastic drug selected from exemestane, letrozole, vorozole, formestane, fadrozole and anastrozole;
  and likely sensitive to a
  a PI3K pathway inhibitor drug, particularly a PI3K pathway inhibitor drug selected from rapamycin, dactolisib, BGT226, SF1126, PKI-587, and NVPBE235;

The SCP classification provides two types of information to a clinician or patient, a prediction of prognosis, in terms of overall survival, and/or in some cases, a prediction of the likelihood that a SCP class of tumour will be sensitive to, or resistant to, a class, or several classes of anti-neoplastic drug treatment.

Recommendations of drug treatment for SCP can be informed by the specific cellular features observed in this class of tumours. In some embodiments only one class of drugs is recommended for patients in one SCP group. To take SCP17 as an example, in addition to the prediction of a poor prognosis for these patients, the high prevalence of EGFR– cells which express a marker for hypoxia (e.g. CIAX) that defines this group suggests that these tumours may be sensitive to drugs designed to be activated in a hypoxic environment, such as the quinone-alkylating antineoplastic class of drugs. In some embodiments, SCP classification may allow more effective selection of candidates for participation in trials for certain classes of drugs, for example SCP17 patients would be good candidates for novel hypoxia-targeting drugs.

In another embodiment, an SCP assignment assigns a likelihood of drug resistance, rather than sensitivity. Current tumour classifications used to assign or exclude ER-targeting drugs, such as hormone receptor positive, or triple negative, are shown to contain several novel SCP groupings, some with significantly differing clinical outcome, or distinguishing markers that may indicate a unique drug sensitivity. Novel thresholds provided herein distinguish the SCP4, or SCP18 subset of patients comprising many ER-negative cells highly likely to be ER drug resistant, representing a small subset of current clinical classifications. The inventors propose that classification with a likelihood of drug resistance, as for SCP4 or SCP18, rather than sensitivity, provides an important clinical benefit by excluding patients from drug trials or treatment plans comprising the indicated formulations. Detection of KRAS mutation in order to predict tyrosine-kinase therapy resistance in EGFR+ lung cancer is another example of a biomarker for drug resistance used by clinicians.

In some embodiments, the SCP is assigned a plurality of recommended drugs, which may be prescribed singly, or in combination, or consecutively. To take SCP3 as an example, firstly, survival comparisons of patients in this SCP within the parent HR+HER2−/+ clinical classification show that while both SCP1 and SCP3 comprise many CK+HR$^{high}$ cells, SCP1 patients have a good outcome, whereas SCP3 have a likelihood of poor outcome. SCP offer a nuanced prognosis compared to classical groupings which would not differentiate SCP1 from SCP3, and may, for example, affect a clinician's urgency in terms of case handling, promote choice of a more aggressive drug treatment, or consideration of combination therapy or use of a succession of targeted drugs.

Secondly, SCP3 is characterised by a heterogenous mix of tumour cells, each expressing markers which suggest sensitivity to different drugs. SCP3 tumours are defined by 70% of more cells of the cellular identity 10, expressing high levels of hormone receptors (HR). High HR expression indicates these tumours cells are likely to be sensitive to drugs targeting hormones, for example, to aromatase-inhibitors, SERM or SERD drugs. Yet poor prognosis of SCP3 indicates drug combinations might be beneficial. The additional presence of HR+ HER2− cells in SCP patients suggests that a proportion of SCP3 tumour cells will respond to PIK3 pathway inhibitors. Lastly, SCP3 tumours are also characterised by the presence of a significant, though smaller proportion of cells which are HR−. Patients with aggressive HR− tumours are often prescribed drugs targeting cell proliferation, such as mitotic inhibitors, or anti-metabolite drugs. A classification of SCP3, associated with three different types of treatment, should thus lead a clinician to consider a single treatment, a combination therapy, or consecutive treatment with the drugs listed above.

In some situations, as the SCP groups are relative, and mutually exclusive, a classification can provide implicit information on clinical outcome which informs drug choice. For the example of SCP2, although no high or low risk clinical outcome is expressly assigned, the patient is excluded from the similar SCP1 associated with very good outcome, indicating an intermediate chance of survival. This may lead a clinician to choose aggressive second-line drugs suited to the SCP2 morphology, such as anti-angiogenics, instead of first line hormone-targeted therapy, despite the presence of HR+ cells.

Information such as drug availability or cost, mutations, tumour severity grade, age, or co-morbidities may also be considered in combination with the tumour characterisation as broadly drug-sensitive according to the invention when choosing a course of treatment for such patients.

A high probability of poor prognosis alone, such as that associated with SCP8 can also useful in a clinical setting. Increased certainty, even in the context of a negative prognosis can still be useful to a patient, providing a choice of alternative treatments that may are best suited to extend survival, even if they are unlikely to cure a patient (such as for SCP6), or in certain cases with a very high risk of poor prognosis such as the highly heterogenous SCP8 tumours, palliative care may be preferred in the context of the unpleasant side effects caused by many breast cancer treatment regimens or co-morbidities.

In certain embodiments, the patient is assigned to a probable outcome group according to the presence of cellular communities that were assigned in said cellular community assignment step:

CCI1, CCI3, CCI5, CCI8, CCI9, or CCI10: likely good outcome. The presence of these CCI can indicate a significantly better outcome than the average of all samples.

CCI2, CCI4, CCI6, or CCI7: likely bad outcome. The presence of more of these CCI can indicate a significantly worse outcome than the average of all samples.

In order to determine the most appropriate indication of patient outcome, Log-transformed densities of communities or single cells, alongside the clinical subgrouping and grading, were provided to a coxph survival model in order to find significant associations of certain community or single-cell types with patient risk and to investigate the hazard ratios.

A further aspect of the invention relates to a pharmaceutical formulation for use in methods of treatment of cancer, particularly cancer derived from a tissue characterised by expression of steroid hormone receptor expression, particularly neoplastic cells derived from breast, ovary or endometrial tissue, more particularly neoplastic cells derived from human breast or human mammary epithelium, wherein the cancer patient has been assigned to an patient subgroup defined by an SCP or tumour identity according to the methods set forth herein.

A further set of embodiments relate to the methods of using pharmaceutical formulations for the treatment of cancer, particularly breast cancer, informed by the morphological features that characterize the SCP grouping of the patient sample.

One set of embodiments of this aspect of the invention relate to a pharmaceutical formulation for use in treatment of cancer, particularly breast cancer, wherein the cancer patient has been assigned to an SCP selected from SCP3, SCP14, SCP15, and SCP16 according to the methods set forth herein.

In one embodiment, the pharmaceutical formulation for use in treatment of cancer assigned to SCP3, SCP14, SCP15, or SCP16 comprises an anthracycline-type antineoplastic drug, particularly an anthracycline-type antineoplastic drug selected from daunorubicin, doxorubicin, epirubicine, idarubicin, mitoxantrone and pixantrone.

In one embodiment, the pharmaceutical formulation for use in treatment of cancer assigned to SCP3, SCP14, SCP15, or SCP16 comprises a mitotic inhibitor-type taxane-type antineoplastic drug, particularly a mitotic inhibitor-type taxane-type antineoplastic drug selected from capazitaxel, docetaxel, nab-paclitaxel, paclitaxel, vinblastine, vincristine, and vinorelbine.

In one embodiment, the pharmaceutical formulation for use in treatment of cancer assigned to SCP3, SCP14, SCP15, or SCP16 comprises an antineoplastic drug selected from vincristine, vinblastine, vinorelbine, vinflunine, cryptophycin 52, halichondrins, dolastatins and hemiasterlines, or from the group comprising colchicine, podophyllotoxin, rigosertib, steganacin, ABT-751, combretastatins and 2-methoxyestradiol.

In another embodiment, the pharmaceutical formulation for use in treatment of cancer assigned to SCP3, SCP14, SCP15, or SCP16 comprises an antineoplastic platinum complex, particularly carboplatin, satraplatin, cisplatin, dicycloplatin, nedaplatin, oxaliplatin, picoplatin, triplatin tetranitrate.

In yet another embodiment, the pharmaceutical formulation for use in treatment of cancer assigned to SCP3, SCP14, SCP15, or SCP16 comprises an alkylating antineoplastic drug, particularly an alkylating antineoplastic drug selected from altretamine, bendamustine, busulfan, carboplatin, carmustine, cisplatin, cyclophosphamide, chlorambucil, dacarbayine, ifosfamide, lomustine, mechlorethamine, melphalan, oxaliplatin, temozolomide, thiptepa, or trabectedin.

In another embodiment, the pharmaceutical formulation for use in treatment of cancer assigned to SCP3, SCP14, SCP15, or SCP16 comprises an antimetabolite-type antineoplastic drug, particularly an antimetabolite-type antineoplastic drug selected from; azacytidine, 5-fluorouracil, 6-mercaptopurine, capecitabine, clofarabine, cytarabine, decitabine, floxuridine, fludarabine, gemcitabine, hydroxyurea, hydroxycarbamide, methotrexate, nelarabine, pemetrexed, pentostatin, pralatrexate, or phototrexate.

The SCP information obtained by the method according to the above aspects of the invention is used to identify patients who may benefit from chemotherapeutic intervention targeting proliferation and cell division.

An alternative of this aspect of the invention relates to a pharmaceutical formulation for use in treatment of cancer, wherein the cancer patient has been assigned to an SCP characterised by high HR expression selected from SCP1, or SCP3 according to the methods set forth herein.

In one embodiment, the pharmaceutical formulation for use in treatment of cancer assigned to SCP1 or SCP3 comprises a selective estrogen receptor modulator (SERM) antineoplastic drug, particularly a SERM drug selected from raloxifene, toremifene or tamoxifen.

In one embodiment, the pharmaceutical formulation for use in treatment of cancer assigned to SCP1 or SCP3 comprises a selective estrogen receptor degraders (SERD) antineoplastic drug, particularly fulvestrant, brilanestrant or elacestrant.

In one embodiment, the pharmaceutical formulation for use in treatment of cancer assigned to SCP1 or SCP3 comprises an aromatase inhibitor antineoplastic drug, particularly an aromatase inhibitor antineoplastic drug selected from exemestane, letrozole, vorozole, formestane, fadrozole and anastrozole.

Another alternative of this aspect of the invention relates to a pharmaceutical formulation for use in treatment of cancer, wherein the cancer patient has been assigned to the SCP 2 according to the methods set forth herein. The pharmaceutical formulation according to this alternative comprises an antiangiogenic antineoplastic drug, particularly an antiangiogenic antineoplastic drug selected from bevacizumab, thalidomide or lenalidomide.

Similarly, the invention provides a pharmaceutical formulation comprising an EZH2 methyltransferase inhibitor antineoplastic drug, particularly an EZH2 methyltransferase inhibitor antineoplastic drug selected from 3-deazaneplanocin A (DZNep), tazemetostat, EPZ005687, El1, GSK126, or UNCI999, for use in treatment of cancer assigned to an SCP characterised by H3K27me3+ cells, or intermediate HR expression particularly from SCP selected from SCP5, or SCP12.

Another alternative of this aspect of the invention relates to a pharmaceutical formulation comprising an inhibitor of EGFR bioactivity antineoplastic drug, particularly an inhibitor of EGFR bioactivity antineoplastic drug selected from gefetinib, erlotinib, lapatinib, cetuxumib, neratinib, osimeratib, panitumamib, vandetanib, necitumumab, or dacomitinib, for use in treatment of cancer, wherein the cancer patient has been assigned to SCP15.

Yet another alternative of this aspect of the invention relates to a pharmaceutical formulation comprising a hypoxia-activated drug, for example a quinone-alkylating antineoplastic drug, particularly mitomycin C, for use in treatment of cancer, wherein the cancer patient has been assigned to SCP17.

Yet another alternative of this aspect of the invention relates to a pharmaceutical formulation comprising an HER2 targeting antineoplastic drug, therapy or vaccine, particularly a HER2 targeting antineoplastic drug selected from trastuzumab, pertuzumab, SYD985, RCI48, A166, HER2ALT-P7, T-DM1, ARX788, KN026, BVAC-B, MT-5111, AVX901, TAS0728, MP0274, MM-302, FS102, H2NVAC, and/or HER2-targeted cell therapy HER2.taNK cells, HER2-pulsed dendritic cells, HER2-targeting T cells, for use in treatment of cancer, wherein the cancer patient has been assigned to an SCP comprising HER2+ cells selected from SCP2, SCP6, SCP 7, SCP 9, SCP 10, SCP11 or SCP13. Compared to clinical classification representing the current state of the art in the examples, the invention reclassifies HER2+ tumours into SCP 11, 6,7,9,10, 13, and 2, each comprising additional markers which can be used to predict efficacy of different clinical approaches.

Yet another alternative of this aspect of the invention relates to a pharmaceutical formulation comprising PI3K pathway inhibitors, particularly rapamycin, dactolisib, BGT226, SF1126, PKI-587, NVPBE235, for use in treatment of cancer, wherein the cancer patient has been assigned to an SCP comprising HR high/+ HER2- cells selected from SCP1, SCP3, SCP11, or SCP18.

Similarly, within the scope of the present invention is administering to the patient an effective dose of a cancer drug in accordance to the patient's assignment to a specific subgroup according to the above description.

Another aspect relates to a method of diagnosis, whereby a patient is assigned to a group for whom cessation of chemotherapy is recommended. The inventors surmise that SCP1 might not require treatment despite current assessments classifying these patients into a group for whom conventional chemotherapeutic treatment is recommended.

Another aspect of the invention relates to a system for use in characterizing the tumour of a breast cancer patient, in order to classify, or stratify the breast cancer patient into a group sharing similar cellular features. The system is configured to conduct the method for tumour stratification disclosed herein.

Components of the system may include: A device for analysing a cancer tissue sample obtained from the patient;

particularly wherein the cancer tissue is derived from human breast or human mammary epithelium; a plurality of molecular probes for labelling the cancer tissue sample, each probe being specific for a biomolecule, wherein each of said molecular probes is characterized by a detectable marker, and wherein the (labelled) biomolecules are selected from a list comprising or consisting of biomolecules i. to xii as specified according to the first aspect of the invention. The device is able to obtain information about the expression of each of said plurality of biomolecules at the resolution of a single cell, and configured to assign, in a cell assignment step, a cellular identity (CI) to each single cell in said labelled tissue sample based on the expression of said plurality of biomolecules, wherein the cellular identity is assigned as a function of the cell's expression of biomolecules identified by markers according to the CI1 to CI14 as specified according to the first aspect of the invention.

The system may optionally be further configured to assign, in a pathology group assignment step, a single cell pathology (SCP) patient group according to the proportion of each cellular identity assigned in the cell assignment step the sample contains, according to the constituent cell types characterizing SCP1-18 specified in the first aspect of the invention listed above, to the sample.

An alternative of this aspect relates to a system for assigning cells comprised in a tissue sample to one of a plurality of cellular identities, the system comprising the following components:

a. an input module configured to receive data recorded from a labelled tissue sample at single-cell resolution, wherein the data comprises information on a level of expression of the biomolecule in each cell. The data has local resolution of a single cell, meaning that the signal of one cell can be distinguished from the signal of another cell. The labelled tissue sample is labelled with a plurality of molecular probes, each probe being specific for a biomolecule. Each of said molecular probes is characterized by a detectable marker. A signal of the detectable marker correlates with an amount of expression of the biomolecule.

the biomolecules are selected from a list comprising:
i. epithelial cadherin (E-cadherin),
ii. cytokeratin (CK) 18 and/or 19,
iii. CK7,
iv. oestrogen receptor (ER) and/or progesterone receptor (PR),
v. a marker of cellular proliferation, particularly Ki-67 and/or PCNA,
vi. CK5 and/or p63 and/or CK14,
vii. p53,
viii. a hormone receptor (HR), particularly a receptor for oestrogen and/or progesterone (ER and PR, respectively),
ix. a marker of apoptosis, particularly the cleaved form of poly ADP-ribose polymerase (cPARP) and/or the cleaved form of caspase3 (cC3),
x. epidermal growth factor receptor (EGFR),
xi. a marker of hypoxia, particularly carbonic anhydrase (CAIX); and
xii. a marker of DNA content, particularly a DNA intercalating dye;

b. an evaluation module configured to assign each level of expression to an expression group selected from a high ($^{hi}$), a positive (+), a low ($^{lo}$), or a negative (−) expression level in each cell comprised in the labelled tissue sample;

c. a cell assignment module configured to assign each cell to a cellular identity (CI), based on the assigned expression group, wherein the CI for each cell is selected from:

CI1: CIAX$^{hi}$, EGFR−, (ER and/or PR)+, (CK5 and/or p63 and/or CK14)+;

CI2. p53$^{hi}$, (cC3 and/or cPARP)+, (ER and/or PR)−, (CK18 and/or CK19)−, (CK5 and/or p63 and/or CK14)−;

CI3. (Ki-67 and/or PCNA)+, CK7−, (CK18 and/or CK19)−, (ER and/or PR)−, (CK5 and/or p63 and/or CK14)−;

CI4. p53$^{hi}$, EGFR+, CIAX$^{hi}$, (ER and/or PR)−, (CK5 and/or p63 and/or CK14)−;

CI5. (CK5 and/or p63 and/or CK14)+, CK7−, (CK18 and/or CK19)−, (ER and/or PR)−;

CI6. E-cadherin$^{hi}$, (CK18 and/or CK19)$^{hi}$, CK7+, (ER and/or PR)+, (CK5 and/or p63 and/or CK14)−;

CI7. CK7+, (CK18 and/or CK19)+, (ER and/or PR)−, (CK5 and/or p63 and/or CK14)−;

CI8. E-cadherin−, CK7−, (CK18 and/or CK19)−, (CK5 and/or p63 and/or CK14)−, (ER and/or PR)−;

CI9. (E-cadherin$^{lo}$ or E-cadherin−), ((CK18 and/or CK19)− or (CK18 and/or CK19)$^{lo}$), (ER and/or PR)$^{lo}$, (CK5 and/or p63 and/or CK14)−;

CI10. ((CK18 and/or CK19)$^{hi}$ or (CK18 and/or CK19)+), E-cadherin+, (ER and/or PR)$^{hi}$, CK5 and/or p63 and/or CK14)−;

CI11. ((CK18 and/or CK19)$^{hi}$ or (CK18 and/or CK19)+), E-cadherin+, (ER and/or PR)+, CK5 and/or p63 and/or CK14)−;

CI12. (E-cadherin$^{lo}$ or E-cadherin+), ((ER and/or PR)$^{lo}$ or (ER and/or PR)−), (CK5 and/or p63 and/or CK14)−;

CI13. p53$^{hi}$, EGFR+, (ER and/or PR)$^{hi}$, ((CK5 and/or p63 and/or CK14)$^{lo}$ and/or (CK5 and/or p63 and/or CK14)−);

CI14. CK7+, (CK18 and/or CK19)+, (CK5 and/or p63 and/or CK14)+, (ER and/or PR)−;

d. an output module configured to display or plot a CI for each cell.

In certain embodiments, the system additionally comprises:

e. a pathology group assignment module configured to assign said tissue sample to a single cell pathology (SCP) group according to the proportion of each cellular identity assigned by the cell assignment module, wherein the list of SCP groups comprises:

SCP1. >70% of single cells are CI10;
SCP2. >70% of single cells are CI11;
SCP3. ≤70% of single cells are CI10;
SCP4. >70% of single cells to CI12;
SCP5. ≤70% of single cells are CI12;
SCP6. >80% of single cells are CI9;
SCP7. >80% of single cells are CI8;
SCP8. ≤70% of single cells are CI9; or CI10, or CI12;
SCP9. >60% of single cells are CI9;
SCP10. >70% of single cells are CI9; CI10, or CI12;
SCP11. >60% of single cells are CI7;
SCP12. >70% of single cells are CI6;
SCP13. >50% of single cells are CI5;
SCP14. >60% of single cells are CI3;
SCP15. >70% of single cells are CI4;
SCP16. >50% of single cells are CI2;
SCP17. >50% of single cells are CI1;
SCP18. >90% of single cells are CI14 wherein the output module is configured to display or plot the SCP group.

Similarly, the invention encompasses a method of treating a patient having been diagnosed with a cancer disease characterized with a likely drug sensitivity associated with one of the SCP patient groups according to the aspects of the invention specified above. This method entails administering to the patient an effective amount of an antineoplastic drug likely to be effective for the patient group as specified according to any of the aspects of the invention specified above, or its pharmaceutically acceptable salt, as specified in detail herein.

The invention further encompasses the use of the following features in a kit, or in the manufacture of a kit for the detection of subsets of cancer patients with differing likelihood of drug sensitivity and/or clinical outcomes. First, use of molecular probes specific for the biomolecules in a list comprising or consisting of:

E-cadherin, CK18 and/or 19, CK7, ER and/or PR, a marker of cellular proliferation, particularly Ki-67 and/or PCNA, CK5 and/or p63 and/or CK14, p53, a HR, particularly a ER and/or PR, a marker of apoptosis, particularly cPARP and/or cC3, EGFR, a marker of hypoxia, particularly CAIX; and a marker of DNA content, particularly a DNA intercalating dye; and optionally CD3 or CD90; CD20 or CD19; CD68; CD44 and/or CD45; Fibronectin; vimentin, and CD31 and/or vWF and/or CD34;

wherein the molecular probe is conjugated to an isotope or fluorescent dye, particularly wherein the molecular probes are conjugated to isotopes from a list comprising or consisting of:

Indium 113, Lanthanum 139, Praseodymium 141, Neodymium 142, Neodymium 143, Neodymium 144, Neodymium 145, Neodymium 146, Neodymium 148, Neodymium 150, Samarium 147, Samarium 149, Samarium 152, Europium 151, Europium 153, Gadolinium 155, Gadolinium 156, Gadolinium 158, Gadolinium 160, Terbium 159, Dysprosium 162, Dysprosium 163, Dysprosium 164, Erbium 166, Erbium 167, Erbium 168, Thulium 169, Ytterbium 170, Ytterbium 172, Ytterbium 173, Ytterbium 174, Ytterbium 176, Lutetium 175.

Some embodiments of this aspect of the invention relate to the use of antibodies as molecular probes. An alternative embodiment relates to the use of nucleic acids as molecular probes.

Wherever alternatives for single separable features are laid out herein as "embodiments", it is to be understood that such alternatives may be combined freely to form discrete embodiments of the invention disclosed herein.

The invention further encompasses the following items

A. A method to indicate the clinical outcome of a cancer patient, wherein the method comprises the steps of:
  a. providing a cancer tissue sample obtained from the patient;
  b. labelling the cancer tissue sample with a plurality of molecular probes, each probe being specific for a biomolecule, wherein each of said molecular probes is characterized by a detectable marker, and wherein the biomolecules are selected from a list comprising or consisting of:
    i. epithelial cadherin (E-cadherin),
    ii. cytokeratin (CK) 18 and/or 19,
    iii. CK7,
    iv. oestrogen receptor (ER) and/or progesterone receptor (PR),
    v. a marker of cellular proliferation, particularly Ki-67 and/or PCNA, vi. CK5 and/or p63 and/or CK14,
    vii. p53,
    viii. a hormone receptor (HR), particularly a receptor for oestrogen and/or progesterone (ER and PR, respectively),
    ix. a marker of apoptosis, particularly the cleaved form of poly ADP-ribose polymerase (cPARP) and/or the cleaved form of caspase3 (cC3),
    x. epidermal growth factor receptor (EGFR),
    xi. a marker of hypoxia, particularly carbonic anhydrase (CAIX); and
    xii. a marker of DNA content, particularly a DNA intercalating dye;
  c. in a reading step, obtaining information about the expression of each of said plurality of biomolecules at the resolution of a single cell;
  d. in a cell assignment step, assigning a cellular identity (CI) to each single cell in said labelled tissue sample based on the expression of said plurality of biomolecules, wherein the cellular identity is assigned as a function of the cell's expression of biomolecules identified by markers according to the following list:
    CI1: $CIAX^{hi}$, EGFR−, (ER and/or PR)+, (CK5 and/or p63 and/or CK14)+;
    CI2. $p53^{hi}$, (cC3 and/or cPARP)+, (ER and/or PR)−, (CK18 and/or CK19)−, (CK5 and/or p63 and/or CK14)−;
    CI3. (Ki-67 and/or PCNA)+, CK7−, (CK18 and/or CK19)−, (ER and/or PR)−, (CK5 and/or p63 and/or CK14)−;
    CI4. $p53^{hi}$, EGFR+, $CIAX^{hi}$, (ER and/or PR)−, (CK5 and/or p63 and/or CK14)−;
    CI5. (CK5 and/or p63 and/or CK14)+, CK7−, (CK18 and/or CK19)−, (ER and/or PR)−;
    CI6. E-cadherin$^{hi}$, (CK18 and/or CK19)$^{hi}$, CK7+, (ER and/or PR)+, (CK5 and/or p63 and/or CK14)−;
    CI7. CK7+, (CK18 and/or CK19)+, (ER and/or PR)−, (CK5 and/or p63 and/or CK14)−;
    CI8. E-cadherin−, CK7−, (CK18 and/or CK19)−, (CK5 and/or p63 and/or CK14)−, (ER and/or PR)−;
    CI9. (E-cadherin$^{lo}$ or E-cadherin−), ((CK18 and/or CK19)− or (CK18 and/or CK19)$^{lo}$), (ER and/or PR)$^{lo}$, (CK5 and/or p63 and/or CK14)−;
    CI10. ((CK18 and/or CK19)$^{hi}$ or (CK18 and/or CK19)+), E-cadherin+, (ER and/or PR)$^{hi}$, CK5 and/or p63 and/or CK14)−;
    CI11. ((CK18 and/or CK19)$^{hi}$ or (CK18 and/or CK19)+), E-cadherin+, (ER and/or PR)+, CK5 and/or p63 and/or CK14)−;
    CI12. (E-cadherin$^{lo}$ or E-cadherin+), ((ER and/or PR)$^{lo}$ or (ER and/or PR)−), (CK5 and/or p63 and/or CK14)−;
    CI13. $p53^{hi}$, EGFR+, (ER and/or PR)$^{hi}$, ((CK5 and/or p63 and/or CK14)$^{lo}$ and/or (CK5 and/or p63 and/or CK14)−);
    CI14. CK7+, (CK18 and/or CK19)+, (CK5 and/or p63 and/or CK14)+, (ER and/or PR)−.
  e. in a pathology group assignment step, assigning said cancer tissue sample to a single cell pathology (SCP) patient group according to the proportion of each cellular identity assigned in the cell assignment step the sample contains, wherein the list of SCP patient groups comprises or consists of:
    SCP1. >70% of single cells are CI10;
    SCP2. >70% of single cells are CI11;

SCP3. ≤70% of single cells are CI10;

SCP4. >70% of single cells to CI12;

SCP5. ≤70% of single cells are CI12;

SCP6. >80% of single cells are CI9;

SCP7. >80% of single cells are CI8;

SCP8. ≤70% of single cells are CI9; or CI10, or CI12;

SCP9. >60% of single cells are CI9;

SCP10. >70% of single cells are CI9; CI10, or CI12;

SCP11. >60% of single cells are CI7;

SCP12. >70% of single cells are CI6;

SCP13. >50% of single cells are CI5;

SCP14. >60% of single cells are CI3;

SCP15. >70% of single cells are CI4;

SCP16. >50% of single cells are CI2;

SCP17. >50% of single cells are CI1;

B. The method according to item A, wherein the method of obtaining information about the average expression of said plurality of biomolecules comprises constructing of an image of the cancer tissue sample.

C. The method according to items A or B, wherein the cancer tissue sample is a section.

D. The method according to any one of the items B or C, wherein the cancer tissue sample is a monolayer of adherent cells, or cells otherwise immobilised on a solid surface.

E. The method according to any one of the items A-D, wherein the plurality of biomolecules is labelled by contacting the sample with a plurality of metal-conjugated or fluorescent dye-conjugated antibodies and/or nucleic acid probes.

F. The method according to any one of the items C-E, wherein the method of obtaining information about the average expression of said plurality of biomolecules is imaging mass cytometry at a subcellular resolution, particularly at a resolution of ≤5 μm, or even ≤1 μm.

G. The method according to any one of the items C-F, wherein said method comprises the steps of a. in the labelling step, including additional markers selected from:

xiii. CD3 or CD90;

xiv. CD20 or CD19;

xv. CD68;

xvi. CD44 and/or CD45;

xvii. Fibronectin;

xviii vimentin, and xix CD31 and/or von Willibrand factor (vWF) and/or CD34;

b. in the cell assignment step, including additional cellular identities selected from:

i. CI15. CD44+, CD45+, (CD3 or CD90)+, fibronectin–, E-cadherin–, ((CK5 and/or p63 and/or CK14)$^{lo}$ or (CK5 and/or p63 and/or CK14)–);

ii. CI16. CD20+, (fibronectin$^{lo}$ or fibronectin–), ((E-cadherin$^{lo}$ or E-cadherin–), ((CK5 and/or p63 and/or CK14)$^{lo}$ or (CK5 and/or p63 and/or CK14)–);

iii. CI17. (CD3 or CD90)+, (CD20 or CD19)+;

iv. CI18. CD68+;

v. CI19. vimentin+, (CD34 and/or VWF and/or CD31)+;

vi. CI20. vimentin–, (fibronectin+ or fibronectin$^{hi}$), (CD3 or CD90)–, (CD20 or CD19)–, CD45–, CD44–.

H. The method according to any one of the items C-G, wherein the single cell is a fragment of the image of the cancer tissue sample, particularly a fragment which consists of the pixels inside a region wherein membrane-associated molecules surround a single nucleus.

I. The method according to any of the items C-H, wherein said method comprises the steps of a. in a cellular community detection step, partitioning the image of the cancer tissue sample into multicellular regions, wherein each single cell inside the multicellular region is highly interconnected to neighbouring cells to provide a cellular community;

b. in a cellular community assignment step, assigning a cellular community identity (CCI) to each cellular community according to the number of cells in the cellular community, and the proportion of each CI it contains, wherein the list of CCI comprises or consists of:

CCI1. Among cells with identities CI1-CI14, >10% of single cells are CI6, and the average size of cellular communities is >25 cells; or CCI2. Among cells with identities CI1-CI14, >10% of single cells are CI6, and the average size of cellular communities is ≤25 cells; or CCI3. Among cells with identities CI1-CI14, >10% of single cells are CI2, and the average size of cellular communities is >25 cells, or CCI4. Among cells with identities CI1-CI14, >10% of single cells are CI2, and the average size of cellular communities is ≤25 cells, or CCI5. Among cells with identities CI1-CI14, >10% of cells are CI3, and the average size of cellular communities is ≤25 cells, or CCI6. >5% of all cells are CI19, and >10% of cells are CI20, and >3% cells are CI18, and the average size of cellular communities is <50 cells, or CCI7. >80% of all cells are any of the identities CI1 to CI15, and <10% cells are CI20, and the average size of the cellular communities is <75 cells, or CCI8. >20% of all cells are CI15, and/or 16 and/or CI17, and <40% cells are any of the identities CI1 to CI14, and the average size of the cellular communities is more than 75 cells, or CCI9. >5% of all cells are CI18, and the average size of the cellular communities is >25%, or CCI10 >80% of all cells are any of the identities CI1 to CI14, and <2% cells are CI20, and the average size of the cellular communities is >115 cells and <125 cells.

J. The method according to any of the items A-H, wherein the patient is assigned to a probable outcome group according to the sample's SCP classification in the pathology group assignment step:

SCP4 or SCP18: likely lack of sensitivity to antineoplastic drugs which target ER;

SCP7: likely lack of sensitivity to antiangiogenic antineoplastic drugs;

SCP1, SCP11: likely good outcome,

SCP8, SCP14, SCP17: likely bad outcome,

K. The method according to the item I, wherein the patient is assigned to a probable outcome group according to the number of cellular communities that were assigned in said cellular community assignment step:

CCI1, CCI3, CCI5, CCI8, CCI9, or CCI10: likely good outcome,

CCI2, CCI4, CCI6, or CCI7: likely bad outcome.

L. The method according to any one of the preceding items, wherein the cancer tissue sample comprises or essentially consists of neoplastic cells derived from a tissue characterised by expression of steroid hormone receptor expression, particularly neoplastic cells derived from breast, ovary or endometrial tissue, more particularly neoplastic cells derived from human breast or human mammary epithelium.

M. A pharmaceutical formulation comprising
  a. an anthracycline-type antineoplastic drug, particularly an anthracycline-type antineoplastic drug selected from daunorubicin, doxorubicin, epirubicine, idarubicin; or
  b. a mitotic inhibitor-type antineoplastic drug, particularly a mitotic inhibitor-type antineoplastic drug selected from capazitaxel, docetaxel, nab-paclitaxel, paclitaxel, vinblastine, vincristine, vinorelbine (see uz341wo); or
  c. an antineoplastic platinum complex, particularly carboplatin, satraplatin, cisplatin, dicycloplatin, nedaplatin, oxaliplatin, picoplatin, triplatin tetranitrate; or
  d. an alkylating antineoplastic drug, particularly an alkylating antineoplastic drug selected from altretamine, bendamustine, busulfan, carboplatin, carmustine, cisplatin, cyclophosphamide, chlorambucil, dacarbayine, ifosfamide, lomustine, mechlorethamine, melphalan, oxaliplatin, temozolomide, thiptepa, or trabectedin; or
  e. an antimetabolite-type antineoplastic drug, particularly an antimetabolite-type antineoplastic drug selected from; azacytidine, 5-fluorouracil, 6-mercaptopurine, capecitabine, clofarabine, cytarabine, decitabine, floxuridine, fludarabine, gemcitabine, hydroxyurea, hydroxycarbamide, methotrexate, nelarabine, pemetrexed, pentostatin, pralatrexate, or phototrexate;
  f. for use in treatment of cancer, wherein the cancer patient has been assigned to an SCP selected from SCP3, SCP14, SCP15, and SCP16.

N. A pharmaceutical formulation comprising
  a. a selective estrogen receptor modulator (SERM) antineoplastic drug, particularly a SERM drug selected from raloxifene, toremifene or tamoxifen;
  b. a selective estrogen receptor degraders (SERD) antineoplastic drug, particularly fulvestrant, brilandestrant and elacestrant; and/or
  c. an aromatase inhibitor antineoplastic drug, particularly an aromatase inhibitor antineoplastic drug selected from exemestane, letrozole, vorozole, formestane, fadrozole and anastrozole;
  for use in treatment of cancer, wherein the cancer patient has been assigned to an SCP selected from SCP1, or SCP3.

O. A pharmaceutical formulation comprising an antiangiogenic antineoplastic drug, particularly an antiangiogenic antineoplastic drug selected from bevacizumab, thalidomide or lenalidomide, for use in treatment of cancer, wherein the cancer patient has been assigned to SCP2.

P. A pharmaceutical formulation comprising an EZH2 methyltransferase inhibitor antineoplastic drug, particularly an EZH2 methyltransferase inhibitor antineoplastic drug selected from 3-deazaneplanocin A (DZNep), tazemetostat, EPZ005687, Ell, GSK126, or UNCI999; for use in treatment of cancer, wherein the cancer patient has been assigned to an SCP selected from SCP5, or SCP12.

Q. A pharmaceutical formulation comprising an inhibitor of EGFR bioactivity antineoplastic drug, particularly an inhibitor of EGFR bioactivity antineoplastic drug selected from gefetinib, erlotinib, lapatinib, cetuxumib, neratinib, osimeratib, panitumamib, vandetanib, necitumumab, or dacomitinib, for use in treatment of cancer, wherein the cancer patient has been assigned to SCP15.

R. A pharmaceutical formulation comprising a quinone-alkylating antineoplastic drug, particularly mitomycin C, for use in treatment of cancer, wherein the cancer patient has been assigned to SCP17.

S. A pharmaceutical formulation comprising an HER2 targeting antineoplastic drug, particularly a HER2 targeting antineoplastic drug selected from trastuzumab, pertuzumab, SYD985, RCI48, A166, HER2ALT-P7, T-DM1, ARX788, KN026, BVAC-B, MT-5111, AVX901, TAS0728, MP0274, MM-302, FS102, H2NVAC, and HER2.taNK cells, HER2-pulsed dendritic cells, HER2-targeting T cells, for use in treatment of cancer, wherein the cancer patient has been assigned to an SCP selected from SCP2, SCP6, SCP 7, SCP 9, SCP 10, SCP11 or SCP13.

T. A pharmaceutical formulation comprising PI3K pathway inhibitors, particularly rapamycin, dactolisib, BGT226, SF1126, PKI-587, NVPBE235, for use in treatment of cancer, wherein the cancer patient has been assigned to an SCP selected from SCP1, SCP3, SCP11, or SCP18.

1. A method to indicate the clinical outcome of a cancer patient, wherein the method comprises the steps of:
  a. providing a cancer tissue sample obtained from the patient;
  b. labelling the cancer tissue sample with a plurality of molecular probes, each probe being specific for a biomolecule, wherein each of said molecular probes is characterized by a detectable marker, particularly wherein the plurality of molecular probes is capable of distinguishing at least twenty different biomolecules, more particularly wherein the plurality of molecular probes is capable of distinguishing at least twenty five different biomolecules;
  c. in a reading step, obtaining information about the expression of each of said plurality of biomolecules at the resolution of a single cell;
  d. in a cell assignment step, assigning a cellular identity (CI) to each single cell in said labelled tissue sample based on the expression of said plurality of biomolecules, wherein the cellular identity is assigned as a function of the cell's expression of biomolecules identified by markers;
  e. in a pathology group assignment step, assigning said cancer tissue sample to a single cell pathology (SCP) patient group according to the proportion of each cellular identity assigned in the cell assignment step the sample contains.

2. The method according to item 1, wherein the method of obtaining information about the average expression of said plurality of biomolecules comprises constructing of an image of the cancer tissue sample.

3. The method according to item 1 or 2, wherein the cancer tissue sample is a section or a monolayer of adherent cells or cells otherwise immobilised on a solid surface.

4. The method according to any one of the items 1-3, wherein the method of obtaining information about the average expression of said plurality of biomolecules is imaging mass cytometry at a subcellular resolution, particularly at a resolution of $\leq 5$ μm, or even $\leq 1$ μm.

5. The method according to any one of the items 1 to 4, wherein the plurality of biomolecules is labelled by contacting the sample with a plurality of metal-conjugated or fluorescent dye-conjugated antibodies and/or nucleic acid probes.

6. The method according to any one of the items 3-5, wherein the method of obtaining information about the average expression of said plurality of biomolecules is imaging mass cytometry at a subcellular resolution, particularly at a resolution of $\leq 5$ μm, or even $\leq 1$ μm.

7. The method according to any one of the items 2-6, wherein the single cell is a fragment of the image of the cancer tissue sample, particularly a fragment which consists of the pixels inside a region wherein membrane-associated molecules surround a single nucleus.

8. The method according to any one of the items 2-7, wherein said method comprises the steps of
   a. in a cellular community detection step, partitioning the image of the cancer tissue sample into multicellular regions, wherein each single cell inside the multicellular region is highly interconnected to neighbouring cells to provide a cellular community;
   b. in a cellular community assignment step, assigning a cellular community identity (CCI) to each cellular community according to the number of cells in the cellular community, and the proportion of each CI it contains.

9. The method according to any one of the items 1-9, wherein the patient is assigned to a probable outcome group according to the sample's SCP classification in the pathology group assignment step.

10. The method according to any one of the items 1-9, wherein biomolecules for which the molecular probes are specific, are selected from a list comprising or consisting of:
   i. epithelial cadherin (E-cadherin),
   ii. cytokeratin (CK) 18 and/or 19,
   iii. CK7,
   iv. oestrogen receptor (ER) and/or progesterone receptor (PR),
   v. a marker of cellular proliferation, particularly Ki-67 and/or PCNA,
   vi. CK5 and/or p63 and/or CK14,
   vii. p53,
   viii. a hormone receptor (HR), particularly a receptor for oestrogen and/or progesterone (ER and PR, respectively),
   ix. a marker of apoptosis, particularly the cleaved form of poly ADP-ribose polymerase (cPARP) and/or the cleaved form of caspase3 (cC3),
   x. epidermal growth factor receptor (EGFR),
   xi. a marker of hypoxia, particularly carbonic anhydrase (CAIX); and
   xii. a marker of DNA content, particularly a DNA intercalating dye;
   xiii. CD3 or CD90;
   xiv. CD20 or CD19;
   xv. CD68;
   xvi. CD44 and/or CD45;
   xvii. Fibronectin;
   xviii. vimentin, and
   xix. CD31 and/or von Willibrand factor (vWF) and/or CD34.

11. The method according to any one of the items 1-10, wherein cellular identities assigned in the cell assignment step, are selected from a list comprising or consisting of:

CI1: CIAX$^{hi}$, EGFR–, (ER and/or PR)+, (CK5 and/or p63 and/or CK14)+;
   CI2. p53$^{hi}$, (cC3 and/or cPARP)+, (ER and/or PR)–, (CK18 and/or CK19)–, (CK5 and/or p63 and/or CK14)–;
   CI3. (Ki-67 and/or PCNA)+, CK7–, (CK18 and/or CK19)–, (ER and/or PR)–, (CK5 and/or p63 and/or CK14)–;
   CI4. p53$^{hi}$, EGFR+, CIAX$^{hi}$, (ER and/or PR)–, (CK5 and/or p63 and/or CK14)–;
   CI5. (CK5 and/or p63 and/or CK14)+, CK7–, (CK18 and/or CK19)–, (ER and/or PR)–;
   CI6. E-cadherin$^{hi}$, (CK18 and/or CK19)$^{hi}$, CK7+, (ER and/or PR)+, (CK5 and/or p63 and/or CK14)–;
   CI7. CK7+, (CK18 and/or CK19)+, (ER and/or PR)–, (CK5 and/or p63 and/or CK14)–;
   CI8. E-cadherin–, CK7–, (CK18 and/or CK19)–, (CK5 and/or p63 and/or CK14)–, (ER and/or PR)–;
   CI9. (E-cadherin$^{lo}$ or E-cadherin–), ((CK18 and/or CK19)– or (CK18 and/or CK19)$^{lo}$), (ER and/or PR)$^{lo}$, (CK5 and/or p63 and/or CK14)–;
   CI10. ((CK18 and/or CK19)$^{hi}$ or (CK18 and/or CK19)+), E-cadherin+, (ER and/or PR)$^{hi}$, CK5 and/or p63 and/or CK14)–;
   CI11. ((CK18 and/or CK19)$^{hi}$ or (CK18 and/or CK19)+), E-cadherin+, (ER and/or PR)+, CK5 and/or p63 and/or CK14)–;
   CI12. (E-cadherin$^{lo}$ or E-cadherin+), ((ER and/or PR)$^{lo}$ or (ER and/or PR)–), (CK5 and/or p63 and/or CK14)–;
   CI13. p53$^{hi}$, EGFR+, (ER and/or PR)$^{hi}$, ((CK5 and/or p63 and/or CK14)$^{lo}$ and/or (CK5 and/or p63 and/or CK14)–);
   CI14. CK7+, (CK18 and/or CK19)+, (CK5 and/or p63 and/or CK14)+, (ER and/or PR)–,
   CI15. CD44+, CD45+, (CD3 or CD90)+, fibronectin–, E-cadherin–, ((CK5 and/or p63 and/or CK14)$^{lo}$ or (CK5 and/or p63 and/or CK14)–);
   CI16. CD20+, (fibronectin$^{lo}$ or fibronectin–), ((E-cadherin$^{lo}$ or E-cadherin–), ((CK5 and/or p63 and/or CK14)$^{lo}$ or (CK5 and/or p63 and/or CK14)–);
   CI17. (CD3 or CD90)+, (CD20 or CD19)+;
   CI18. CD68+;
   CI19. vimentin+, (CD34 and/or VWF and/or CD31)+;
   CI20. vimentin–, (fibronectin+ or fibronectin$^{hi}$), (CD3 or CD90)–, (CD20 or CD19)–, CD45–, CD44–.

12. The method according to any one of the items 1-11, wherein SCP patient groups assigned in the pathology group assignment step, are selected from a list comprising or consisting of:
   SCP19. >70% of single cells are CI10;
   SCP20. >70% of single cells are CI11;
   SCP21. $\leq$70% of single cells are CI10;
   SCP22. wherein >70% of single cells to CI12;
   SCP23. $\leq$70% of single cells are CI12;
   SCP24. >80% of single cells are CI9;
   SCP25. >80% of single cells are CI8;
   SCP26. $\leq$70% of single cells are CI9; or CI10, or CI12;
   SCP27. >60% of single cells are CI9;
   SCP28. >70% of single cells are CI9; CI10, or CI12;
   SCP29. >60% of single cells are CI7;
   SCP30. >70% of single cells are CI6;
   SCP31. >50% of single cells are CI5;
   SCP32. >60% of single cells are CI3;
   SCP33. >70% of single cells are CI4;

SCP34. >50% of single cells are CI2;

SCP35. >50% of single cells are CI1;

SCP36. >90% of single cells are CI14.

13. The method according to any of the items 3-9, wherein cellular community identity (CCI) assigned in the cellular community assignment step, are selected from a list comprising or consisting of:

CCI1. Among cells with identities CI1-CI14, >10% of single cells are CI6, and the average size of cellular communities is >25 cells; or CCI2. Among cells with identities CI1-CI14, >10% of single cells are CI6, and the average size of cellular communities is ≤25 cells; or CCI3. Among cells with identities CI1-CI14, >10% of single cells are CI2, and the average size of cellular communities is >25 cells, or CCI4. Among cells with identities CI1-CI14, >10% of single cells are CI2, and the average size of cellular communities is ≤25 cells, or CCI5. Among cells with identities CI1-CI14, >10% of cells are CI3, and the average size of cellular communities is ≤25 cells, or CCI6. >5% of all cells are CI19, and >10% of cells are CI20, and >3% cells are CI18, and the average size of cellular communities is <50 cells, or CCI7. >80% of all cells are any of the identities CI1 to CI15, and <10% are CI20, and the average size of the cellular communities is <75 cells, or CCI8. >20% of all cells are CI15, and/or 16 and/or CI17, and <40% cells are any of the identities CI1 to CI14, and the average size of the cellular communities is more than 75 cells, or CCI9. >5% of all cells are CI18, and the average size of the cellular communities is >25%, or CCI10 >80% of all cells are any of the identities CI1 to CI14, and <2% cells are CI20, and the average size of the cellular communities is >115 cells and <125 cells.

14. The method according to any one of the preceding items, wherein the cancer tissue sample comprises or essentially consists of neoplastic cells derived from a tissue characterised by expression of steroid hormone receptor expression, particularly neoplastic cells derived from breast, ovary or endometrial tissue, more particularly neoplastic cells derived from human breast or human mammary epithelium.

The invention is further illustrated by the following examples and figures, from which further embodiments and advantages can be drawn. These examples are meant to illustrate the invention but not to limit its scope.

DESCRIPTION OF THE FIGURES

FIG. 16 shows antibody conjugates used in staining panel.

FIG. 17 shows (a-c) Coxph and (d-f) log rank tests for differences in overall survival between each single-cell pathology subgroup and the rest of the patients (a, d) in the cohort, (b, e) in similar SCP subgroups, and (c, f) in the patients clinically categorized as HR+/HER2−.

FIG. 18 shows that when compared to clinically defined subtypes, adding SCP grouping or tumour and stromal community information improved the ability to predict a patient's overall survival using Cox proportional hazards modelling likelihood ratio tests between nested coxph models. The null hypothesis is that the larger model (more variables) is not better than the smaller one. P values <0.05 reject the null hypothesis.

FIG. 19 shows the relationship between single cell pathology (SCP) groupings and standard of care clinical histopathology groups.

EXAMPLES

Methods

Clinical Data

Figure 1:
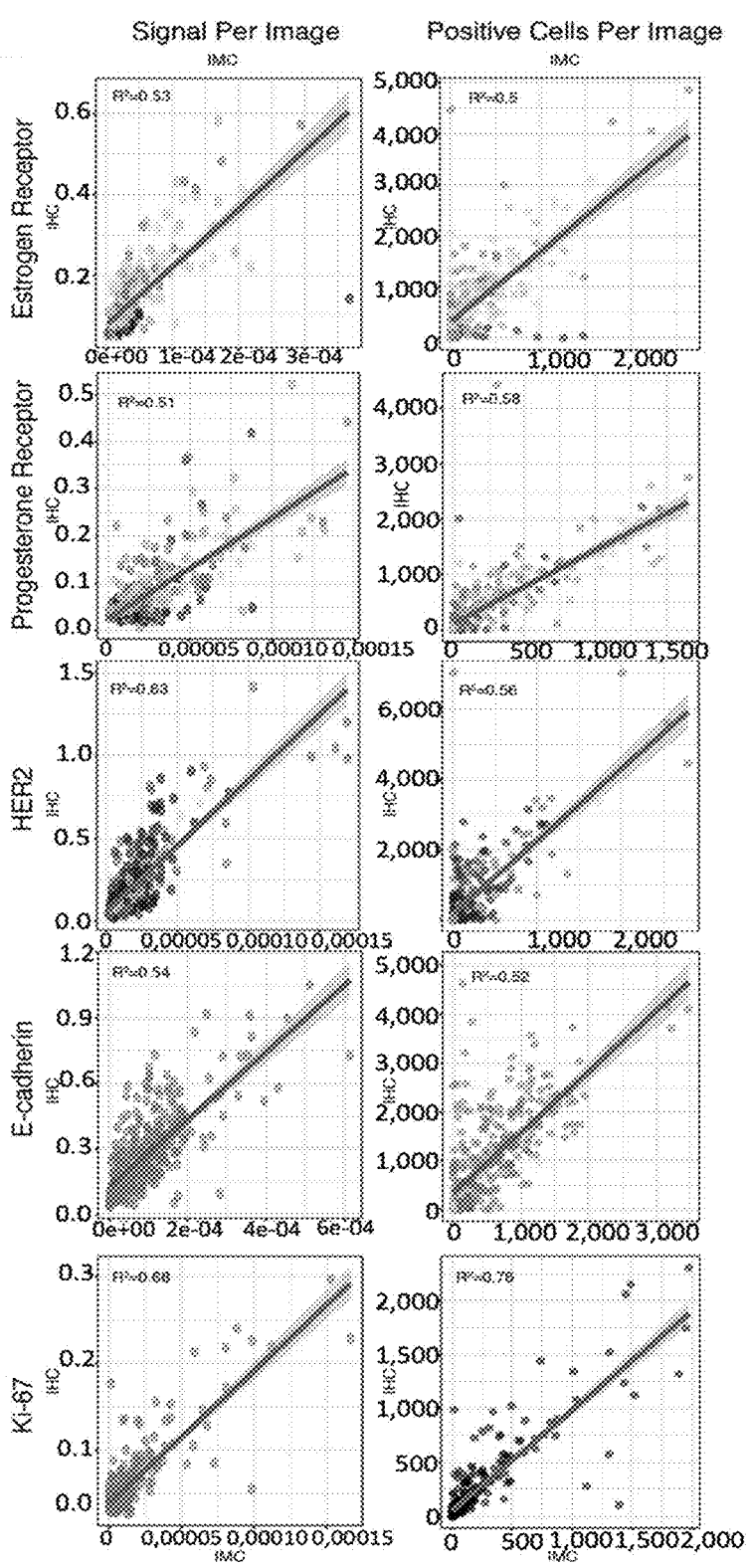
FIG. 1 shows a comparison and reproducibility analysis between the IHC and IMC images. Scatter plots show the correlation between the total quantified IMC signal (ion counts/$\mu m^2$) in sections of the same tumour core compared with either quantification of IHC signal (optical density/$\mu m^2$), or the number of positively stained cells in sections from the same tumour core (n=319 cores).

Tumour samples and patient metadata were collected from cohorts obtained from University Hospital Basel and University Hospital Zurich. The cohort from University Hospital Basel included 281 patients who were not selected for any clinical or histologic features. Pathologists evaluated the suitability of tissue sections for tissue microarray (TMA) construction (Kononen, J. et al. Nat. Med. 4, 844-847 (1998)). TMA contained one 0.8-mm tumour core per patient, in some cases an additional matched healthy breast tissue sample, and a few control samples (liver tissue). The cohort from University Hospital Zurich was comprised of 72 patients; the samples include four 0.6-mm cores from four different regions of each tumour as described (Kundig, P et al. J Translat. Med., 16(1), 118 (2018)). Tumour cores were punched from two central and two peripheral areas that averaged 1 cm in distance between regions. Samples were selected to contain equal proportions of the different tumour grades as well as patients with and without lymph node metastases. In total 720 images were acquired that varied in size and localization in the tumour. This project was approved by the local Commission of Ethics (ref. no. 2014-397 and 2012-0553).

Antibody Panel

An antibody panel was designed to target epitopes specific for breast cancer as well as markers for cell cycle and phospho-signalling and to distinguish epithelial, endothelial, mesenchymal, and immune cell types (FIG. 16).

Tissue Preparation and Staining

Tissue samples were formalin-fixed and paraffin-embedded at the University Hospitals of Basel and Zurich. The antibody panel was used to stain the tissue sections. Tissue sections were dewaxed in xylene overnight and rehydrated in a graded series of alcohol (ethanol:deionized water 100:0, 90:10, 80:20, 70:30, 50:50, 0:100; 5 min each). In a 95° C. water bath, heat-induced epitope retrieval was conducted in Tris-EDTA buffer at pH 9 for 20 min. The tissue microarrays were immediately cooled and then blocked with 3% BSA, 5% goat serum in TBS for 1 h. Samples were incubated overnight at 4° C. in primary antibody at 7.5 g/L diluted in TBS/0.1% Triton X-100/1% BSA. Tissue samples were washed twice with TBS/0.1% Triton X-100 and twice with TBS and dried before imaging mass cytometry measurements.

For combined immunofluorescence and imaging mass cytometry staining, tissues were stained overnight at 4° C. with primary metal-conjugated mouse HER2 ([151] Eu) and rabbit pan-Cytokeratin ($^{175}$Lu) antibodies prior to washing and the mixed addition of fluorescent and metal-conjugated anti-mouse (AF488, $^{165}$Ho) and anti-rabbit (AF555, $^{159}$Tb) secondary stains for 1 h at room temperature. A cover slip was added, and tissue was imaged for fluorescence signal. Subsequently, the cover slip was removed, and samples were washed, dried, and subjected to mass cytometry laser ablation and acquisition.

Imaging Mass Cytometry

Images were acquired using a Hyperion Imaging System (Fluidigm). The largest square area from each core of a TMA was laser ablated in a rastered pattern at 200 Hz, and raw data pre-processing was completed using commercial acquisition software (Fluidigm). IMC acquisition stability was monitored by interspersed acquisition of isotope-containing polymer (Fluidigm). All successful image acquisitions were processed, and images containing pan-marker staining variation specific to TMA location were removed. In cases where the acquisition was interrupted and later continued, 2 tumour images of the same patient were included. Therefore, the 281-patient cohort resulted in 289 tumour, 87 healthy breast and 5 liver control images. Where applicable, signal spillover between channels was corrected using functions from the CATALYST R package (version 1.5.6, Chevrier, S et al. *Cell Syst.* 6, 612-620 (2018)). The 72-patient cohort resulted in 263 tumour, 68 healthy breast and 6 control images used for analysis.

Data Processing

Data were converted to .tiff format and segmented into single cells using the flexible analysis pipeline available at https://github.com/BodenmillerGroup/ImcSegmentation-Pipeline. Briefly, individual cells and tumour/stroma regions were segmented using a combination of llastik 1.1.9 (Sommer, C et al. *From Nano to Macro* 230-233 (IEEE, 2011)) and CellProfiler 2.1.1 (Carpenter et al. *Genome Biol.*7: R100 (2006)). llastik was used to generate a probability map by classifying pixels (Single cells—nuclei, membrane and background; Tumour/Stroma—tumour, stroma and background) based on a combination of membrane and nuclei identifying antibody stains. Probability maps were then segmented into single cell, or tumour and stroma object masks using CellProfiler.

Single-cell segmentation masks and tiff images of the 35 channels were overlaid and single-cell marker expression means and spatial features were extracted using the Matlab toolbox regionprops, as implemented in histoCAT (Schapiro, D. et al. *Nat. Biotechnol.* 31, 545-552 (2013)).

The single cell IDs of each cell's direct neighbours within 4 pixels (4 μm) of the cell of interest was detected and recorded using histoCAT software. The number of pixels expanded to detect neighbours was chosen such that small gaps in segmentation would be bridged, yet no cells after the direct neighbour would be recorded (cell minor axis lengths: 5th-95th percentile 4.84-14.59 pixels, average 9.51 pixels).

Individual cell locations inside or outside of a tumour mask were identified and the distance of each cell to the tumour boundary (from inside and outside of the tumour region) was calculated using the Matlab toolbox regionprops. Distances were measured between the closest pixels of the objects in question.

Data Transformation and Normalization

The presented data were not transformed, and all analyses were based on raw IMC measurements. Single-cell marker expressions are summarized by mean pixel values for each channel. The single-cell data were censored at the 99th percentile to remove outliers, and Z-scored cluster means were visualized in heatmaps. For t-distributed stochastic neighbour embedding (tSNE) and PhenoGraph the data were normalized to the 99th percentile. To visualize the number of cells per image or patient and for survival modelling, the counts were normalized by the image area (total number of pixels) and displayed as cell density. For coxph survival modelling, these densities were multiplied by a factor of $10^{31}$ in order to yield values larger than 1 and then log-transformed.

Clustering and Metaclustering

Single cells of the large cohort from University Hospital Basel were clustered into groups of phenotypically similar cells using a combination of PhenoGraph (Levine, J. H. et al. *Cell* 162, 184-197 (2015), (Bodenmiller, Cell Syst. 2, 225-238 (2016)) for initial, unsupervised clustering and an aggregation of these clusters into larger groups based on their mean marker correlations to identify cellular metaclusters. In a first step, the data were over-clustered to detect and separate rare cell subpopulations. PhenoGraph (version 2.0) was used with default parameters (as implemented in histoCAT/Cyt) and 20 nearest neighbours. For high-dimensional clustering, 29 markers and 4 cell shape features were used: Iridium, Histone, phospho Histone, CK14, CK5, CK8/18, CK19, CK7, panCK, E/P-Cadherin, ER, PR, HER2, GATA3, SMA, Vimentin, Fibronectin, vWF/CD31, CD44, CD45, CD68, CD3, CD20, cleaved Caspase 3/cleaved PARP, Carbonic Anhydrase, phospho-S6, Ki67, p53, EGFR, Area, Eccentricity, Extent, and Number of Neighbours. Of the resulting 71 clusters, 59 epithelial/tumour groups were aggregated into larger groups following the hierarchical clustering (Euclidean distance and Ward's linkage) of their mean marker correlations. Multiscale bootstrap resampling was used to assess the uncertainty of each subtree (R package pvclust, version 2.0), and separation of the hierarchy was assigned so that significant epithelial subtrees were maintained and known biologic differences were separated. This resulted in 14 tumour cell metaclusters of varying size and subtree robustness. Clusters showing marker expression typical of stromal and immune cells, which were limited due to our tumour marker focused panel, were kept as in the original PhenoGraph clustering and not aggregated into larger groups. This metaclustering yielded 27 cellular subgroups, representing various immune, stromal, and epithelial/tumour cell types. The granularity, the level and detail at which phenotypes are divided or clustered, of the studied cell types depends on the selection of both the panel and the choice of parameters. While a more granular distinction of cell types might elucidate even more subtle difference in the marker expressions of cells, it would limit comparability between tumours as many tumour cell types would be patient specific.

Cluster Matching Across Cohorts

Single cells from the second cohort from University Hospital Zurich were clustered unsupervised and independently using PhenoGraph with the same settings described above for the first cohort and a nearest neighbour parameter of 30. The clusters were matched to the most similar metacluster of the previous cohort using Pearson correlation of the z-scored mean marker expressions. In two special cases (clusters 8 and 15) where the cluster in question was rather poorly correlated with all metaclusters but most correlated with a stromal cell type, the cluster were manually re-assigned as upon visual inspection of the images those clusters represented cells forming clear tumour bulks.

Bh-tSNE Algorithm for Visualising High-Dimensional Data

For visualization, high-dimension single-cell data were reduced to two dimensions using the non-linear dimensionality reduction algorithm t-distributed stochastic neighbour embedding (tSNE) (Amir A. D. et al. *Nat Biotechnol.* 31, 545-552 (2013)). The Barnes-Hut implementation of tSNE (bh-tSNE) was applied to 99th-percentile normalized data with default parameters (initial dimensions, 110; perplexity, 30; theta, 0.5). The algorithm was run on a randomly subsampled set of cells (20% from each image) in order to not obscure visible patterns in crowded plots and for better computational performance.

Neighbourhood Analysis

To identify significantly enriched or depleted pairwise neighbour interactions between cell types, histoCAT functions were used to perform a permutation test-based analysis of spatial single-cell neighbourhoods (Shapiro, 2017). Neighbouring cells were defined as those within 4 pixels (4 μm). A p-value cut-off of <0.01 was used for significance.

Single-Cell Pathology Patient Grouping

Patients were grouped based on the proportions of tumour cell metaclusters using the cytofkit R implementation of PhenoGraph (version 1.10.0, Levine, 2015) with 8 nearest neighbours and default parameters. The parameter number of nearest neighbours was chosen such that small groups of patients consisting of a distinct predominant cell type could be separated. A choice of a higher value for this parameter would lead to fewer groups, and hence patients with entirely unrelated predominant phenotypes grouped together. A lower value of the nearest neighbour parameter might capture more subtle differences in cellular composition of tumour types but would severely limit statistical power for group comparison and survival analysis. Patient group 18 was removed from further downstream analysis, due to lack of statistical power, as it contains only three patients with distinct tumours strongly dominated by a rare $HR^+/CK^-$ cell type.

Single-Cell Pathology Group Matching

Tumour cores from the second cohort from University Hospital of Zurich were assigned to the most similar previously defined single-cell pathology group based on their matched tumour cell type components. The inverse of Pearson correlation was used as distance metric.

Spatial Communities

The images were converted into topological neighbourhood graphs where every cell is represented by a node (visualized at the centroid), and the nodes are connected by an edge if the cells directly neighbour each other. Neighbouring cells were defined as those within 4 pixels (4 μm) of the outermost pixel assigned to a cell. Subsequently, the Louvain community detection algorithm (Blondel, V. D. et al. *J. Stat. Mech.* P10008 (2008)) (C implementation by Lefebvre and Guillaume, version 0.2, wrapped by Matlab as used by the implementation of PhenoGraph 2.0 used by histoCAT/Cyt) was applied to identify highly interconnected spatial subunits in the tissue graph. While using community detection algorithms on spatially constrained networks is known to hide underlying non-spatially driven solutions, the only aim of applying the algorithm here was to extract spatial information and identify communities based on physical proximity (Expert P. et al. *PNAS* 108(19), 7663-7668 (2011)). This analysis was performed on epithelial cells alone to identify tumour communities (without including stromal or immune cells in the graph) and again on all cells of a tissue to identify tumour microenvironment communities. A tumour-specific cohesiveness score was calculated based on the average sizes of the identified tumour communities. Communities involving fewer than 10 cells were excluded from further analysis in order to focus on cohesive cell patches and not individual disconnected cells. 15 patients were excluded from analysis based on tumour communities because the imaged regions did not contain any tumour communities consisting of at least 10 cells. In order to identify recurring similar spatial cell type communities, the cytofkit PhenoGraph (Levine, 2015, version 1.10.0) was run on the min-max normalized, absolute numbers of cells of each cell metacluster in each community. This analysis was conducted separately for the tumour communities based on only the epithelial cell types (k=80) and for the microenvironment communities based on all cells but only taking into account the individual stromal cell types and aggregating all tumour cell types into one label (cell type group 100: including all tumour cells, k=30). This analysis was conducted separately for each cohort but based on the matched metacluster cell types.

Stromal Environments

Based on their microenvironment community compositions, images were grouped into 11 different stromal environments using hierarchical clustering (Euclidean distance and Ward's linkage). This analysis was conducted separately for each cohort but based on the matched metacluster cell types.

Overlapping Classifications and Enrichments

Fisher's exact test was used to identify single-cell pathology patient groups enriched for a specific stromal environment. The test was performed using the R function fisher.test (with parameter enrichment="greater") for every potential stromal region of a patient group. The p-values were corrected for multiple testing using the Bonferroni method. This enrichment analysis was also conducted with different combinations of single-cell pathology subgroups, stromal environments, and clinical classifications.

Survival Curves and Coxph Regression Models

Kaplan-Meier survival curves and coxph survival regression models were generated using the R package survival (version 2.42-4). The overall survival as well as the disease-free survival of patients in different clinical or single-cell-defined subgroups was analysed. Both log rank tests and coxph models were employed to investigate whether a patient subgroup significantly deviated from the survival of the remaining patients or from the survival of other patients of similar SCP groups or the same clinical classification. Log-transformed densities of communities or single cells, alongside the clinical subgrouping and grading, were provided to a coxph survival model in order to find significant associations of certain community or single-cell types with patient risk and to investigate the hazard ratios. Nested coxph models were compared using likelihood ratio tests (R package anova.coxph) to assess whether additional variables improved the survival model.

Example 1

Imaging mass cytometry was used to simultaneously quantify 35 biomarkers resulting in 720 high-dimension immunohistochemistry pathology images of tumour tissue from 352 breast cancer patients for whom long-term survival data were available. Spatial, single-cell analysis identified tumour and stromal single-cell phenotypes, their organization and heterogeneity, and enabled categorization of breast cancer cellular architecture based on cellular composition and tissue organization. The analysis revealed multi-cellular features of the tumour microenvironment and novel breast cancer subgroups associated with distinct clinical outcomes. Thus, spatially resolved, single-cell analysis can characterize intra-tumour phenotypic heterogeneity in a disease-relevant manner with the potential to inform patient-specific diagnosis.

Spatially Resolved Single-Cell Phenotypes

Figure 2:
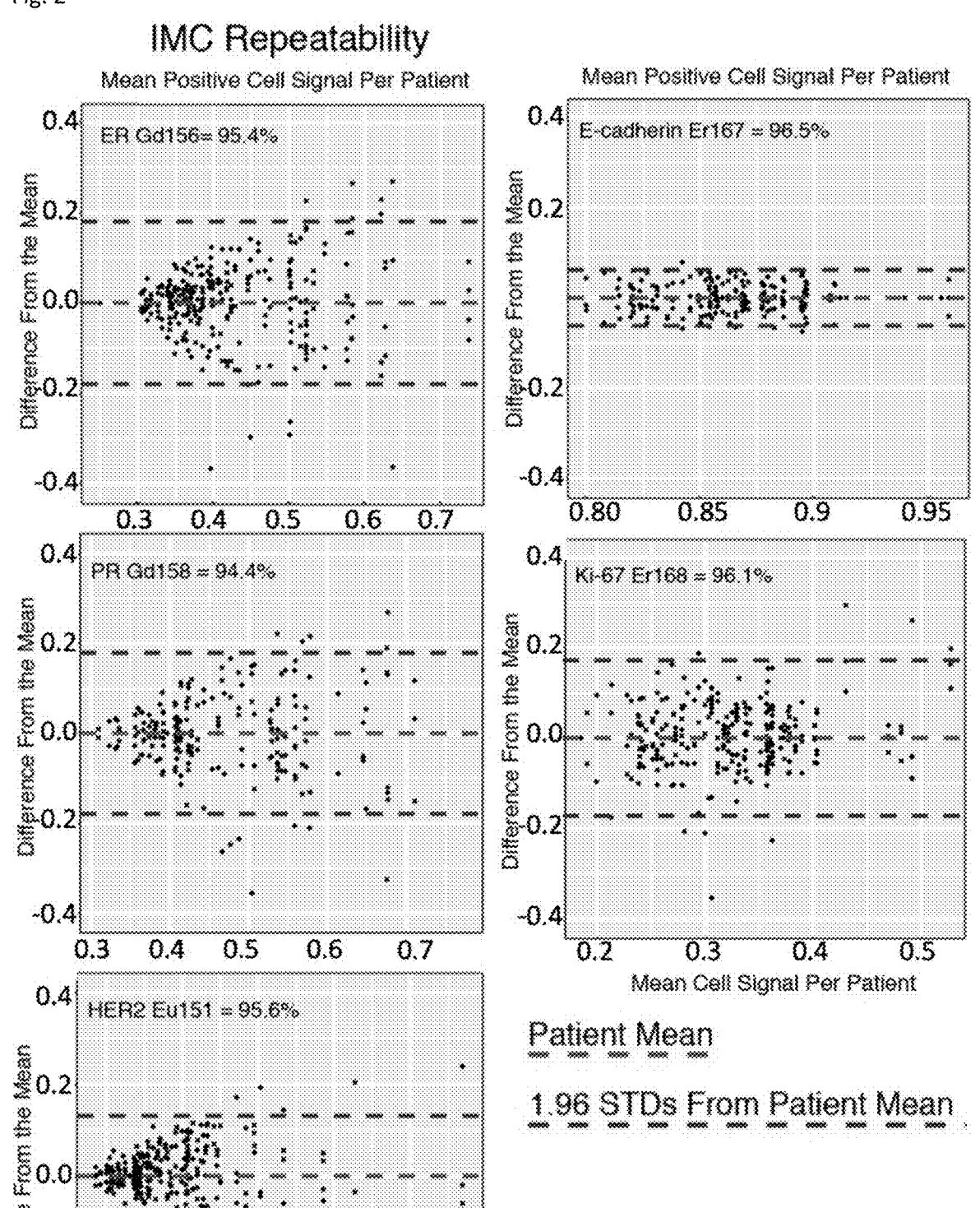
FIG. 2 shows Bland-Altman plots indicating the reproducibility of IMC signal in positively stained cells across images from different regions of the same tumour, adapted to visualize the average across four samples on the x-axis and the difference of every individual sample to the tumour average on the y-axis. Only images containing positively stained cells and more than 200 cells in total were taken into account for this analysis (ER: n=280 cores from 72, PR: n=213 cores from 66 patients, HER2: n=291 cores from 72 patients, Ki67: n=281 cores from 72 patients, E/P-Cadherin: n=200 cores from 65 patients). The red line represents the overall average of the differences to the tumour mean, and the blues lines represent the 95% confidence interval (1.96*standard deviation). The percentage of observations that fall within the confidence interval is indicated at the top of each plot.

To comprehensively quantify the cellular heterogeneity and spatial organization of breast cancer tissue, a breast-histology-specific imaging mass cytometry (IMC) panel was designed designed to image samples from 281 tumours representing all clinical subtypes and pathology grades. IMC combines immunohistochemistry staining using metal iso-tope-labelled antibodies with laser ablation and mass spec-trometry-based detection to produce high-dimension images (Giesen et al., Nat. Methods 11, 417-422 (2014)). The 35-antibody panel simultaneously quantified clinically established breast cancer targets estrogen receptor (ER), progesterone receptor (PR), and HER2, proliferation marker Ki-67, markers of epithelial, mesenchymal, immune, and endothelial lineages, and targets that provide insight into signaling pathways, oncogenes, and epigenetics (FIG. 16). IMC produces images comparable to immunofluorescence or immunohistochemistry but with capacity for highly mul-tiplexed staining (FIGS. 1 and 2).

Figure 3:
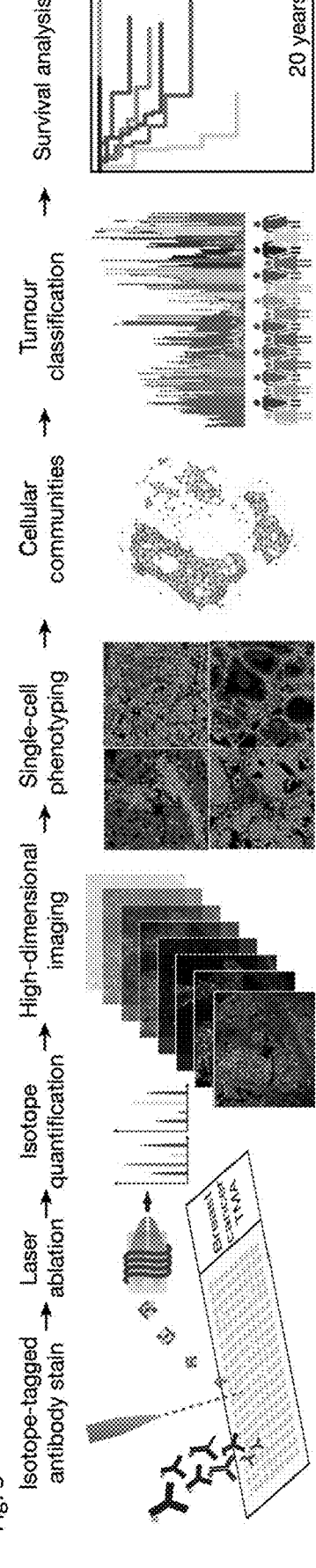
FIG. 3 shows a schematic explaining the workflow of IMC acquisition of multiplexed images from 281 breast cancer patients, the analyses of single-cell phenotypes, cellular communities, tumour and patient subclassification, and overall patient survival.
Figure 4:
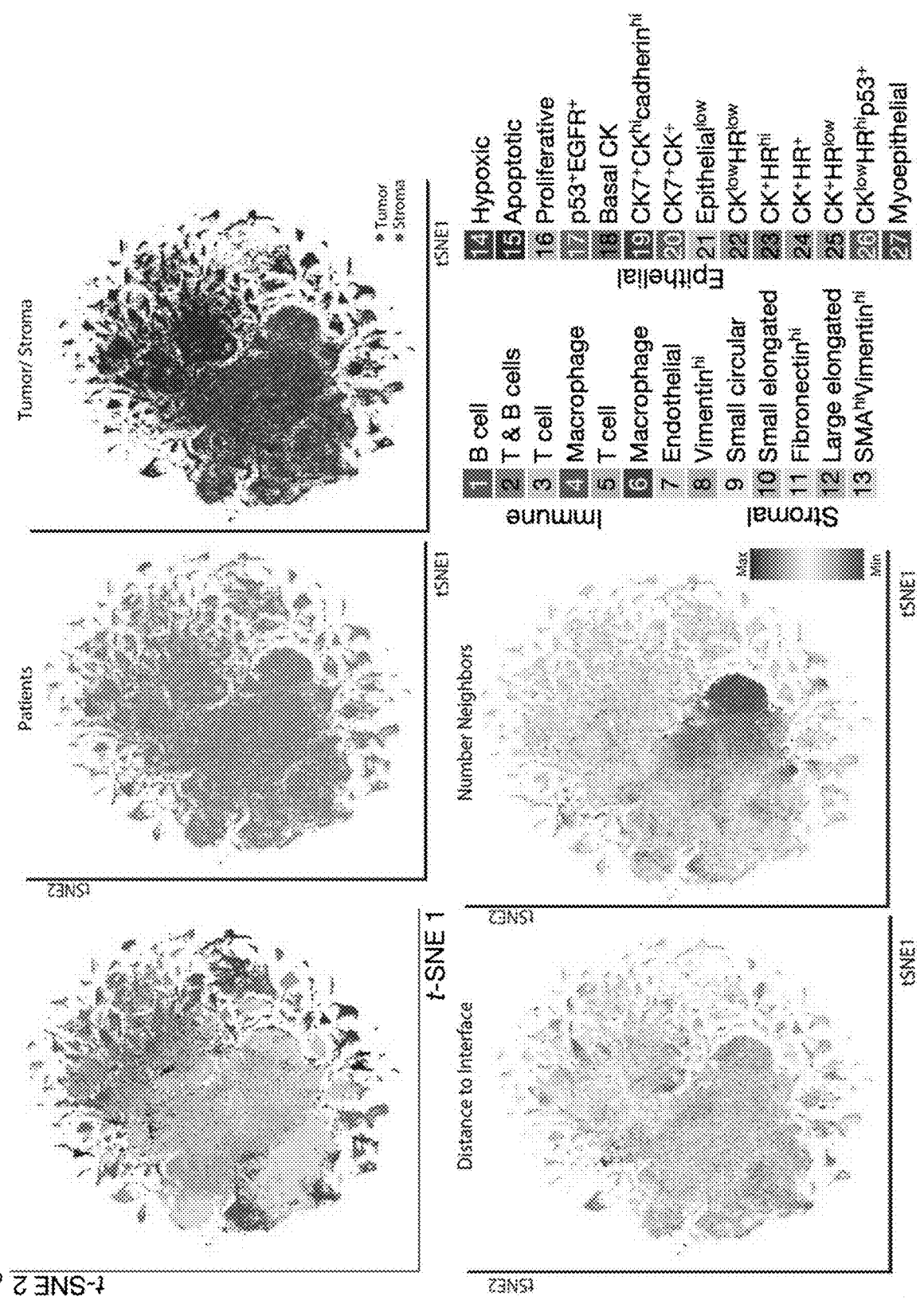
FIG. 4 shows the single-cell phenotypes in high-dimension histopathology of breast cancer illustrated by tSNE maps of 171,288 subsampled single cells from high-dimension images of breast tumours coloured according to their cellular metacluster identifier, patient identity, tumour or stroma classification, distance of each cell to the tumour stroma interface, and the number of neighbours of each cell.
Figure 5:
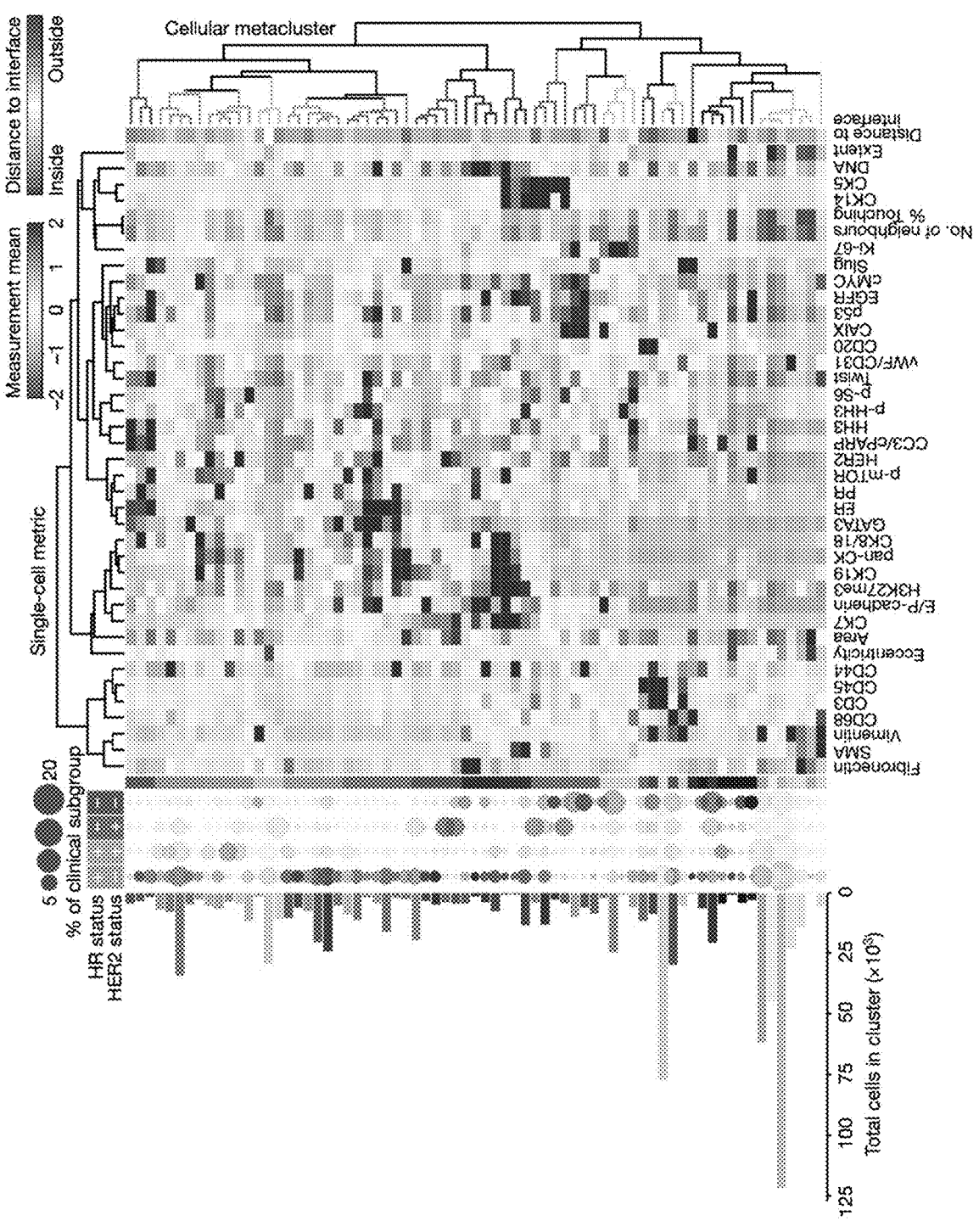
FIG. 5 shows a heatmap of the z-scored mean marker expression or distance to tumour-stroma interface for each cellular metacluster. The absolute cell counts of each cellular metacluster are displayed as a bar plot. In the bubble plot, circle size shows the relative proportion of all cells in a clinical subtype that come from each cluster, and circle opacity shows the proportion of each cluster present in the different clinical subtypes. Cellular metaclusters are represent in the colours indicated in FIG. 9 and FIG. 10.
Figure 6:
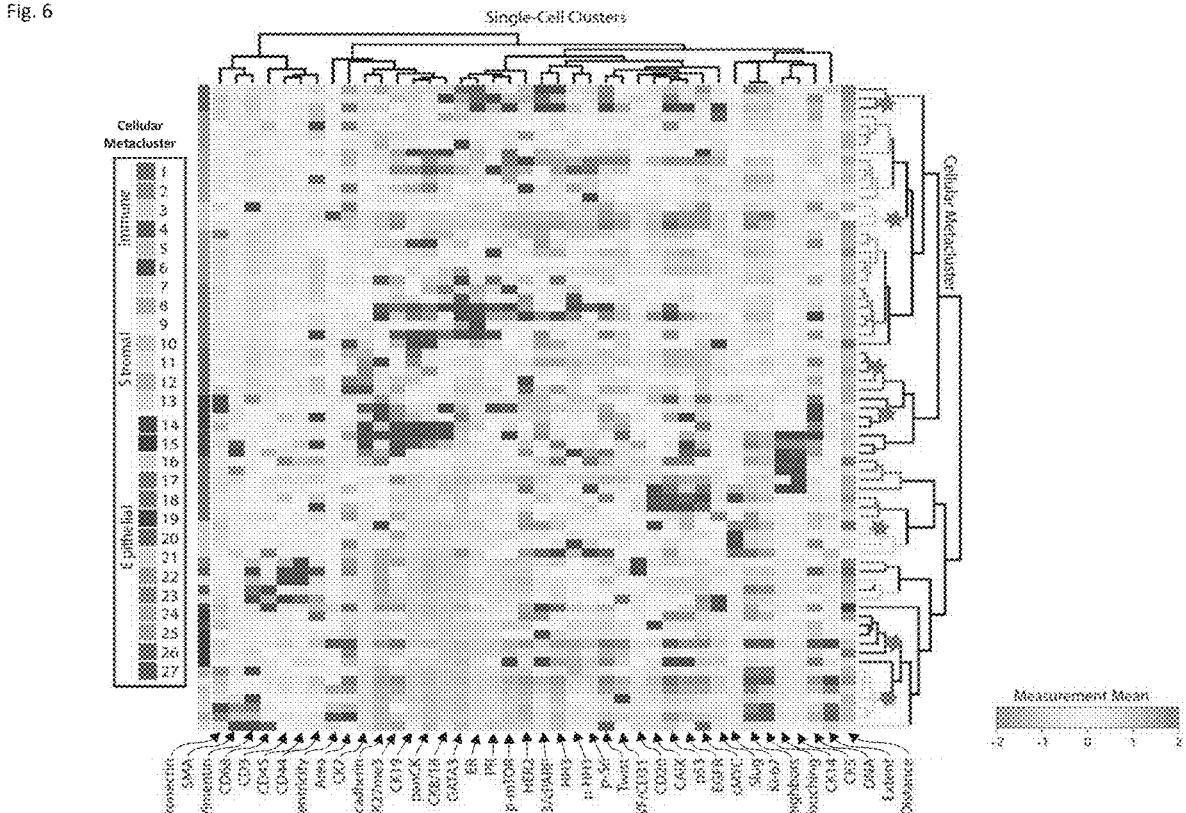
FIG. 6 shows how tumour-cell metacluster cutoffs were defined by hierarchical clustering of the diverse tumour groups defined by PhenoGraph to reduce patient diversity to 14 common tumour cell subtypes (Epithelial cellular metaclusters 14-27). The heatmap displays the z-score of mean marker expressions of single-cell phenotypic clusters identified by PhenoGraph. The colour bar and hierarchical clustering indicate the corresponding metacluster. Red stars on the hierarchical clustering tree indicate the 14 subgroups that robustly reappear as separate groups using multiscale bootstrap resampling (R function pvclust, p<0.05).

Images were segmented into single cells and tumour and stromal regions using a random forest pixel classifier (Ilas-tik), and CellProfilerhttp://f1000.com/work/citation?ids= 4035995,6862877&pre=&pre=&suf=&suf=&sa=0,0 (Bodenmiller, 2016). 855,668 cells in 381 images (289 tumour, 87 healthy breast and 5 liver controls) were iden-tified, and quantified marker expression and spatial features of each cell (FIG. 3). Clustering with PhenoGraph (Levine et al., 2015) identified cell phenotype clusters, hereafter referred to as phenotypes, of endothelial, T and B cell, macrophage, and stromal cell populations as well as 59 diverse tumour cell phenotypes (FIGS. 4 and 5). Some tumour phenotypes were unique to individual patients (FIG. 4). To identify common cellular subtypes within this diver-sity, 14 tumour-cell metaclusters were defined by hierarchi-cal clustering of the PhenoGraph-defined tumour single-cell phenotypes (FIG. 6).

Figure 7:
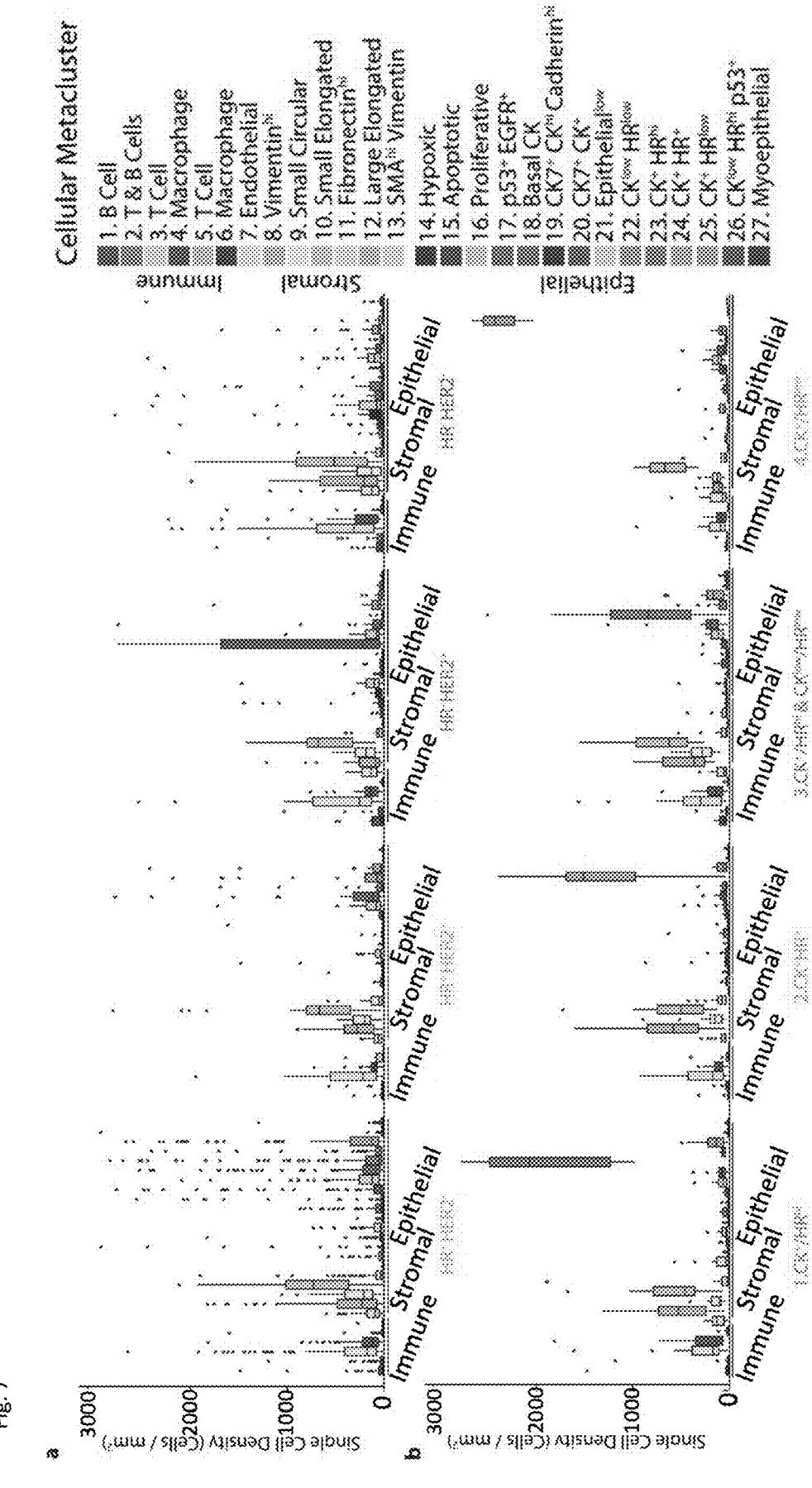
FIG. 7 shows the densities of cellular metaclusters in different clinical subtypes and SCP patient subgroups. Box plots of cellular metacluster densities in (a) patients of each clinical subtype (HR+HER2−: n=173, HR+HER2+: n=29, HR−HER2+: n=23, TripleNeg: n=48) and each (b) SCP subgroup (centre line, median; box limits, first and third quartile; whiskers, 1.5× interquartile range; points beyond whiskers, outliers; SCP1: n=17, SCP2: n=21, SCP3: n=20, SCP4: n=12, SCP5: n=32, SCP6: n=10, SCP7: n=13, SCP8: n=11, SCP9: n=20, SCP10: n=24, SCP11: n=31, SCP12: n=14, SCP13: n=15, SCP14: n=11, SCP15: n=8, SCP16: n=10, SCP17: n=9, SCP18: n=3).
Figure 7:
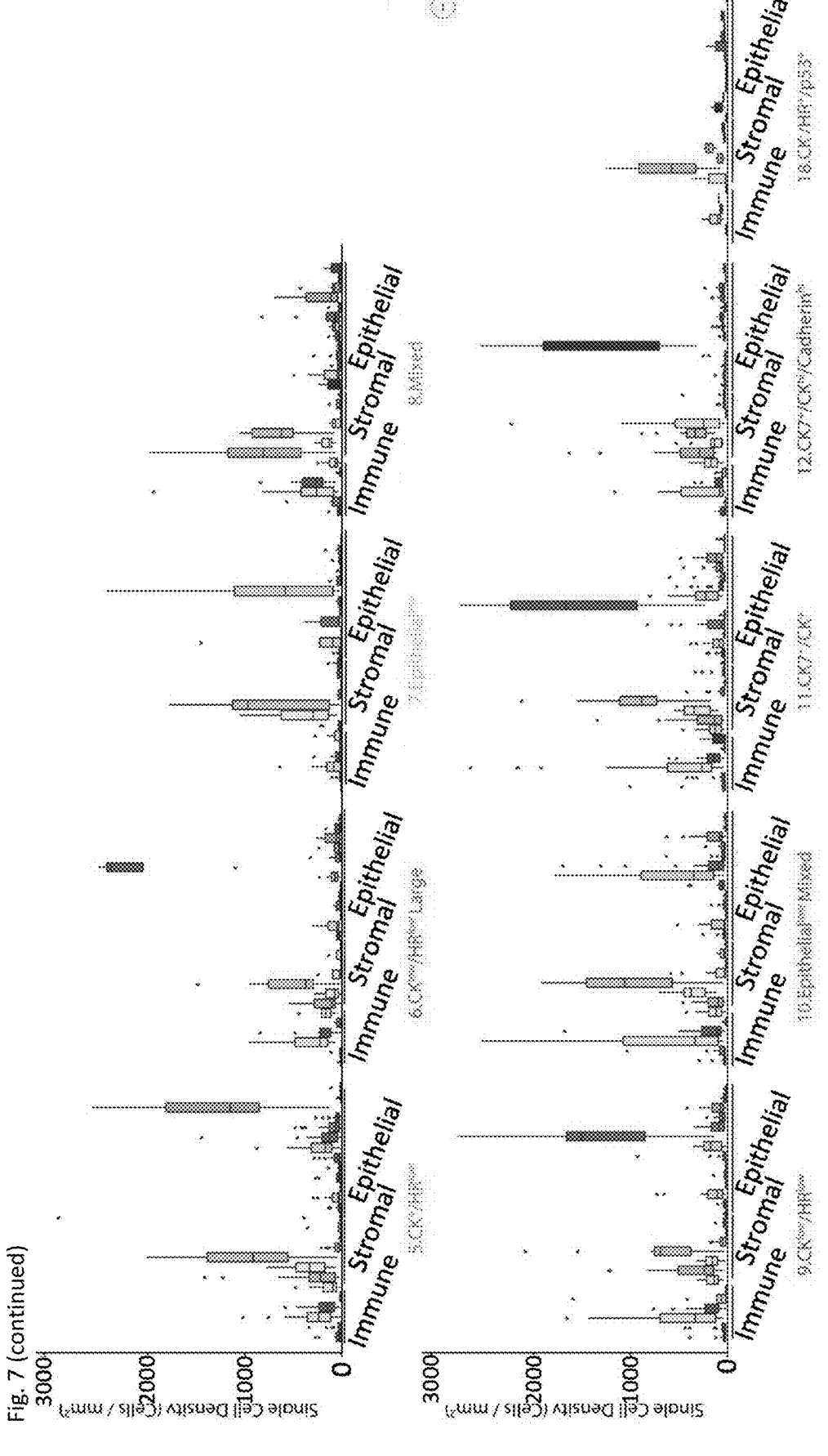
Figure 7:
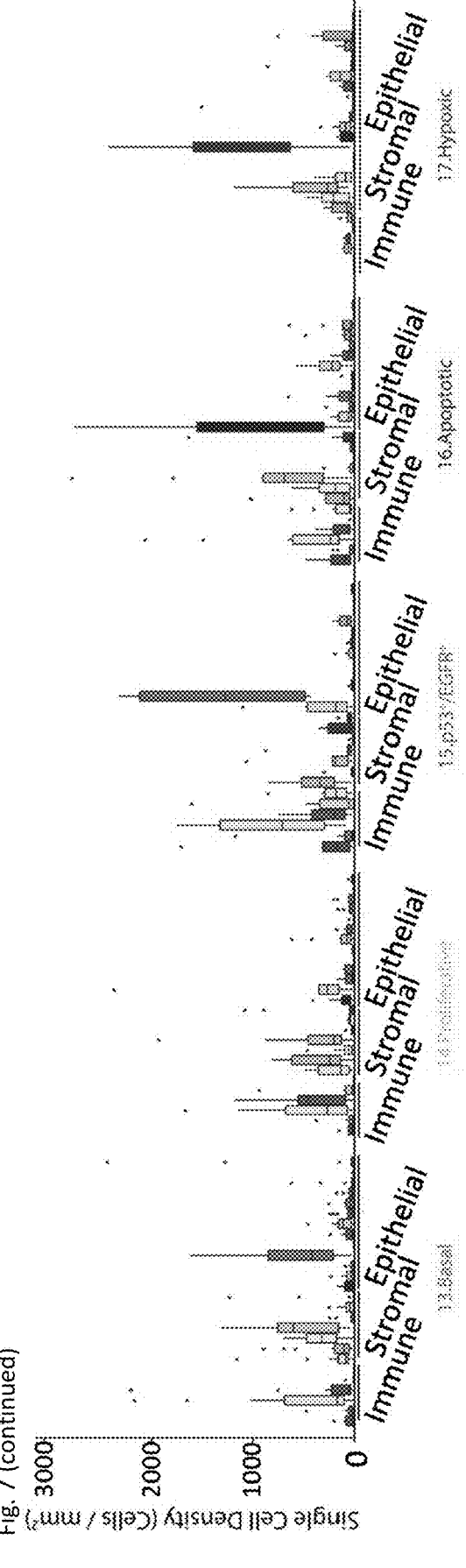

Tumours from every clinical subtype contained fibroblast, endothelial, and immune cell populations at similar densities but were enriched in tumour cell populations with variable expression of cytokeratins, hormone receptors, and HER2 reflective of clinical subtype (FIGS. 5 and 7$a$). Across all patients, immune cells were excluded from the cohesive tumour mass, although immune and fibroblast cells did infrequently infiltrate the tumour mass and rare $HR^{low/-}$ cells lacking cytokeratins invaded past the tumour-stroma front in some samples (FIGS. 5 and 7$a$). Tumour regions contained various luminal $HR^+$ epithelial cell phenotypes identified by combinations of ER, PR, GATA3, E-cadherin, and multiple cytokeratins, but hormone receptors were also expressed without cytokeratins in a few cases (metacluster 26) (FIGS. 5 and 7$b$). Of the luminal cytokeratins (CK7, CK8/18, and CK19), only CK7 was associated with specific luminal tumour cell subsets (metaclusters 19, 20) (FIG. 5). HER2 expression was not a defining metacluster feature but was observed at different levels in multiple phenotypes. Pheno-types without hormone and HER2 receptor expression (char-acteristics of triple-negative breast cancer (TNBC)) included metaclusters with high levels of Ki-67, p53, EGFR, and hypoxia marker CAIX (metaclusters 15-17), basal cytokera-tins (metacluster 18), and even luminal cytokeratins (PG clusters within metaclusters 19, 22) (FIG. 5).

Multi-Cellular Breast Cancer Architecture

Figure 8:
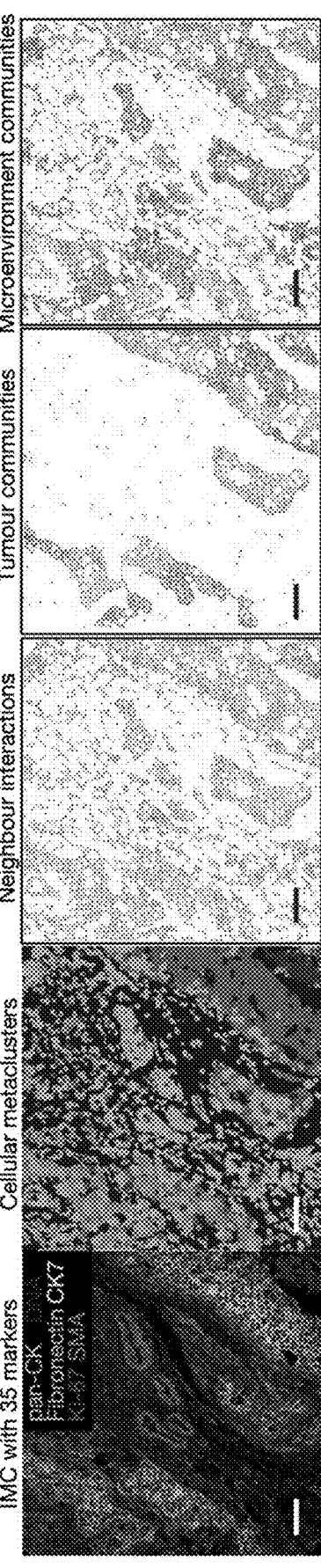
FIG. 8 shows different patterns of multi-cellular architecture in breast tumour tissues based on the defined cellular metaclusters. Cell communities were identified by constructing a topological neighbouring cell interaction network and then applying a graph-based community detection approach using the Louvain algorithm. Applied only to tumour cells, community detection identified dense epithelial patches of different sizes, termed tumour communities (TCs); when applied to all cells, microenvironment communities (MCs) containing tumour and stromal cell components were identified. Representative images depict the different steps in the spatial analysis. From left to right, pseudo-coloured IMC, single-cell mask of the same field of view labelled by cellular metacluster identifier, the neighbouring cellular interactions detected by a topologic cell interaction network, modular regions of the tumour network identifying epithelial communities labelled in colour, and modular regions in the tumour-stroma network identified as tumour microenvironment communities. Scale bar=100 μm.
Figure 9:
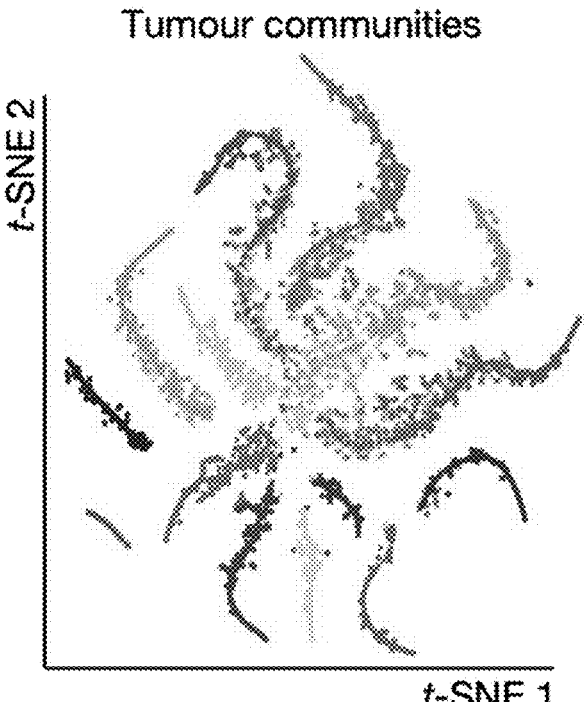
FIG. 9 shows grouping of multi-cell communities according to community size and tumour cell phenotypes (Tumour Communities, TCs). Uniquely coloured tumour communities (n=8495) were clustered by PhenoGraph based on min-max normalized absolute numbers of cells from each cellular metacluster and visualized with both tSNE maps and in stacked bar plots indicating the average number of cells from each cellular metacluster.
Figure 9:
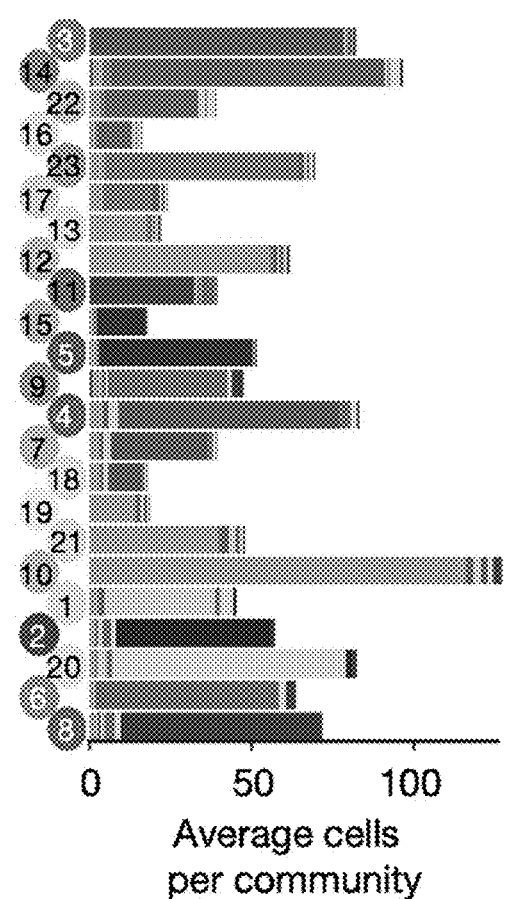
Figure 9:
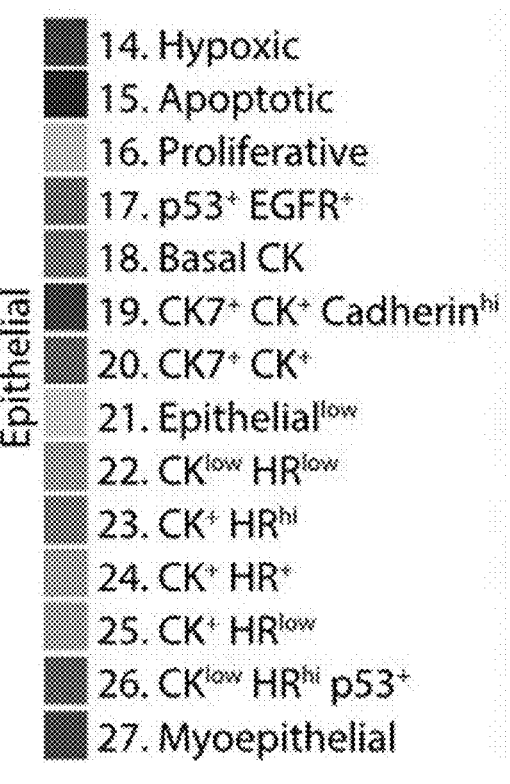
Figure 10:
FIG. 10 shows a second method of grouping of multi-cell communities as in FIG. 9, but in reference to all cells and agnostic to tumour cell type (Microenvironment Communities, MCs). Uniquely coloured microenvironment communities (n=12,854) were clustered by PhenoGraph based on min-max normalized absolute numbers of cells from each cellular metacluster, and visualized with both tSNE maps and in stacked bar plots indicating the average number of cells from each cellular metacluster.
Figure 10:
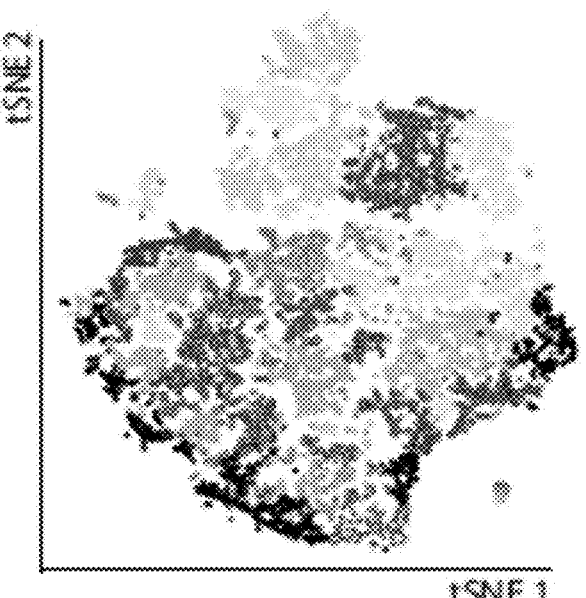
Figure 10:
Figure 10:
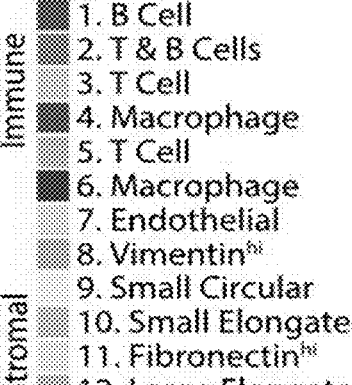
Figure 10:
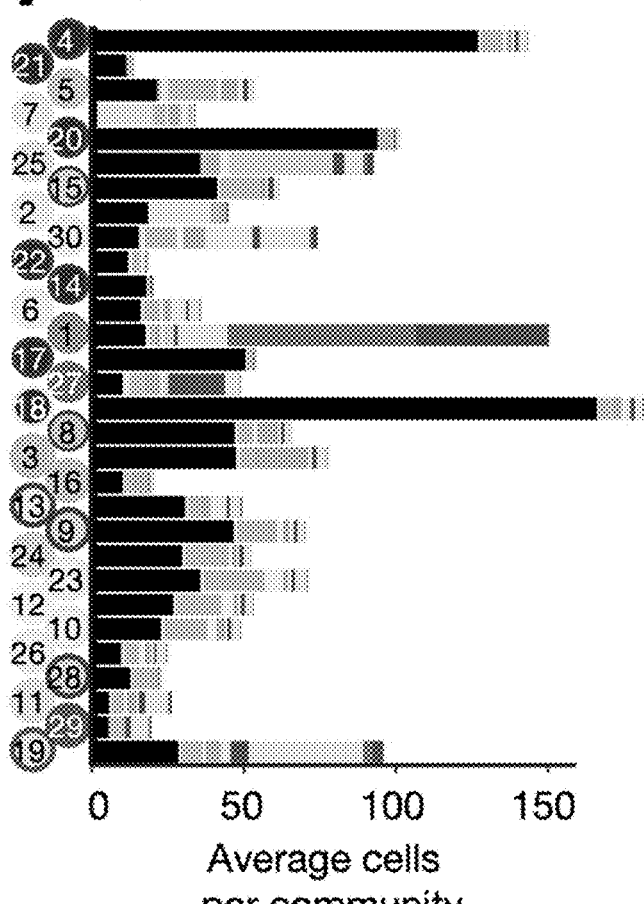

Patterns of multi-cellular architecture in breast tumour tissue were assessed based on these single-cell phenotypes. Tissue function is implemented by multicellular units, or communities, that consist of higher order, rather than paired, interactions between one or more cell phenotypes. Communities were identified by first constructing a topological neighboring cell interaction network and then applying a graph-based community detection approach using the Lou-vain algorithm (Blondel, 2008). Applied only to tumour cells, community detection identified dense epithelial patches of different sizes, termed tumour communities (TCs); when applied to all cells microenvironment commu-nities (MCs) containing tumour and stromal cell components were identified (FIG. 8). Using PhenoGraph, multi-cell communities were grouped according to community size and tumour cell phenotypes (FIG. 9 TCs) or all cells, but agnostic to tumour cell type (FIG. 10 MCs). Tumour com-munities were mostly dominated by a single cellular meta-cluster and were separated based on absolute number of cells (FIG. 9) (TCs 4, 7, 18; Supplementary Images). Some microenvironment communities consisted of fibroblasts that interacted with a variety of tumour cells (MCs 2, 5, 8); others showed sparse stroma content (MCs 14, 17, 18, 20, 21, 22) or were enriched for T cells (MCs 19, 25, 30), macrophages (MC 27), large networks of T and B cells (MC 1), or endothelial cells (MCs 13, 6, 30, 25, 7) (FIG. 10). Fibroblast-enriched communities had few interacting immune cells, aligning with the known roles of fibroblasts as agents of tumour desmoplasia and immune exclusion.

Single-Cell Pathology Subgroups are Related to Clinical Outcome

Figure 11A:
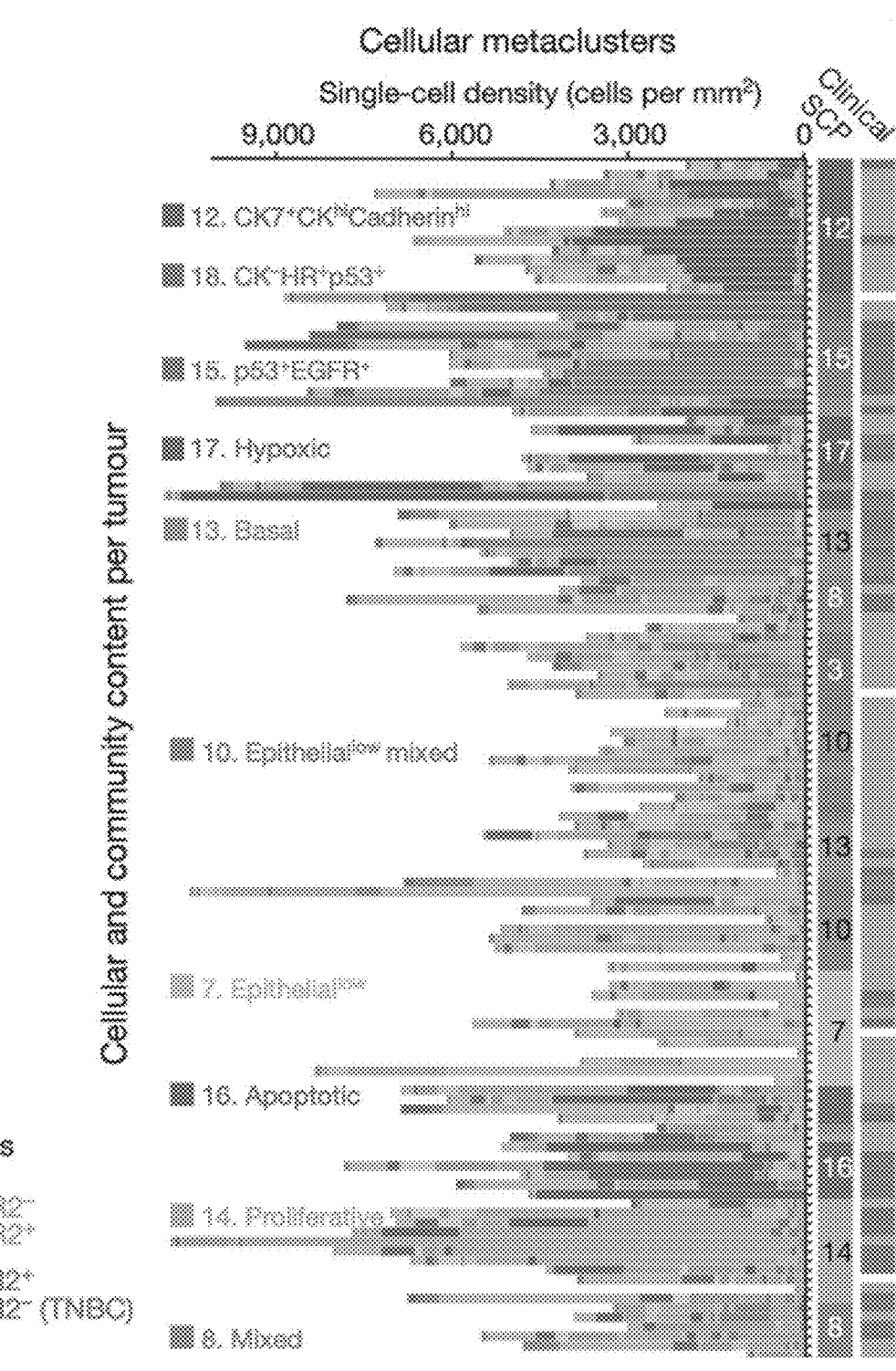
FIG. 11 shows patient tumours grouped based on the tumour cell metacluster composition using unsupervised clustering, identifying 18 single-cell pathology (SCP) subgroups that split the classic clinical subtypes. (a) Hierarchically clustered stacked bar plot shows the cellular metacluster densities in each tumour sample. Coloured columns indicate classical clinical subtypes, and the novel SCP subgroups. (b) Heatmap indicates the proportions of different epithelial tumour communities present within each image.
Figure 11:
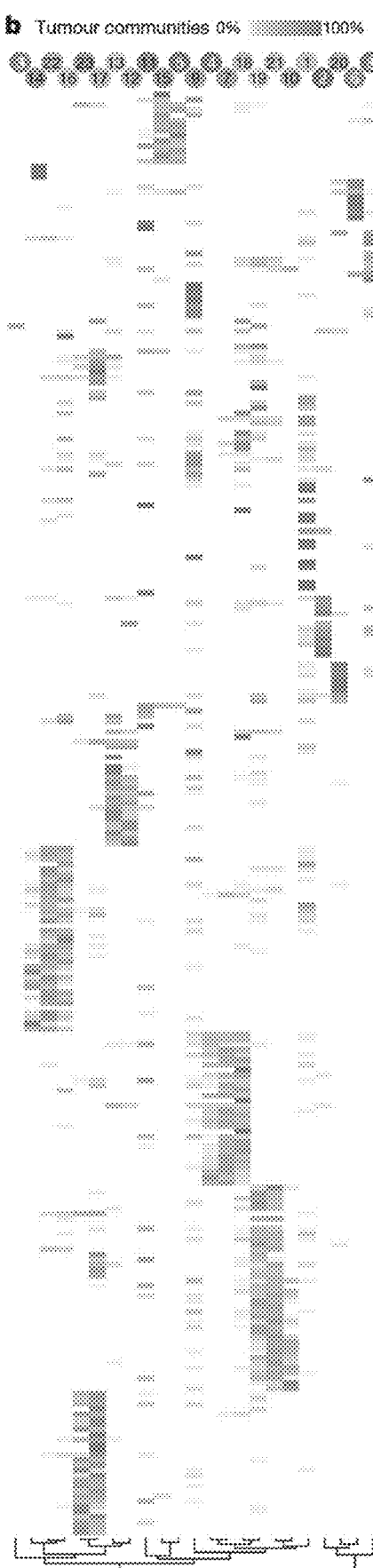
Figure 12:
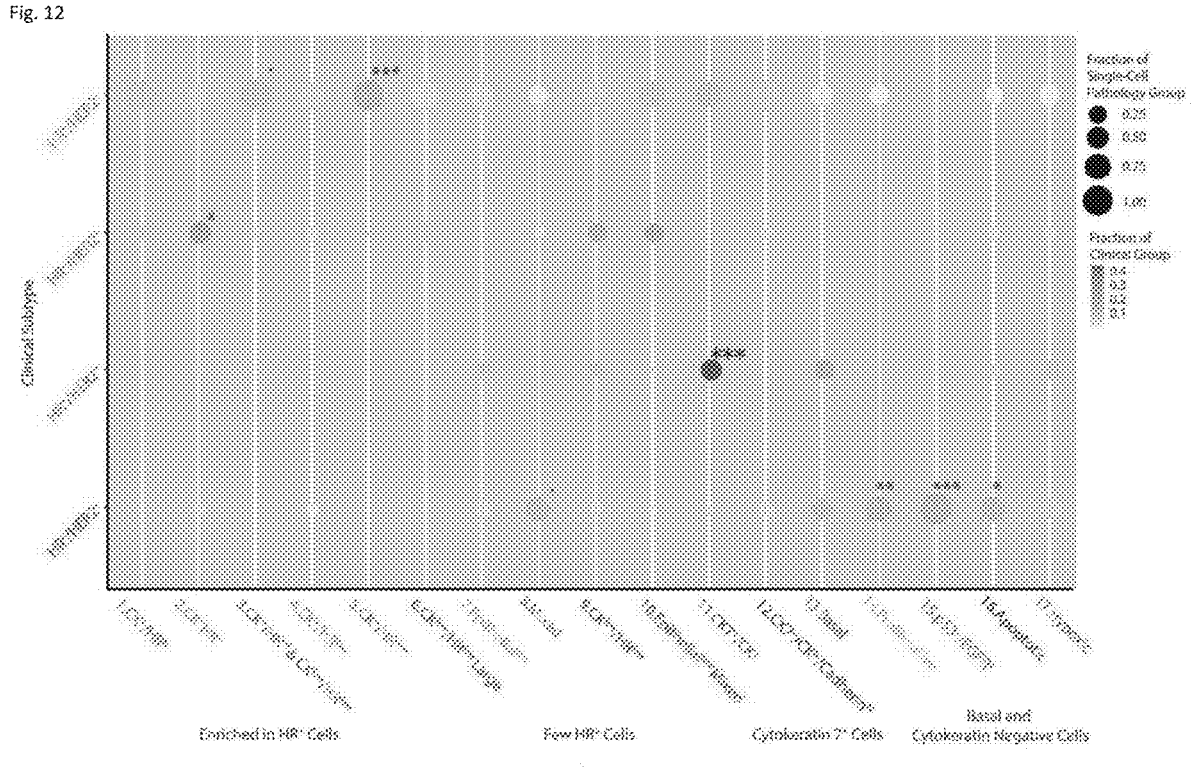
FIG. 12 shows comparisons and enrichments between SCP breast cancer groups and histological based clinical classifications. Bubble plot visualizing overlap between SCP breast cancer patient subgroups (SCP1: n=17, SCP2: n=21, SCP3: n=20, SCP4: n=12, SCP5: n=32, SCP6: n=10, SCP7: n=13, SCP8: n=11, SCP9: n=20, SCP10: n=24, SCP11: n=31, SCP12: n=14, SCP13: n=15, SCP14: n=11, SCP15: n=8, SCP16: n=10, SCP17: n=9, SCP18: n=3 excluded due to low n value) and clinical subtypes (HR+HER2−: n=173, HR+HER2+: n=29, HR-HER2+: n=23, TripleNeg: n=48). One-sided Fisher's exact test for enrichment. •p<0.1, *p<0.05, p<0.01, *p<0.001.

The organization of single cells into communities con-tributes to breast cancer tissue architecture and tumour subtypes with different clinical outcomes was then investi-gated. Cells from multiple cellular metaclusters were found in every clinically defined breast cancer subtype (FIG. 7), supporting the conclusion that general pathology classifica-tion does not fully elucidate inter- and intra-patient cellular heterogeneity. To determine whether the single-cell pathol-ogy landscape would provide a higher resolution patient classification than classic histology-based clinical subtypes, patient tumours were grouped based on the tumour cell metacluster composition using unsupervised clustering, identifying 18 single-cell pathology (SCP) subgroups that split the classic clinical subtypes (FIGS. 11$a$ and 12). SCP subgroups had various proportions of the epithelial tumour communities (FIG. 11$b$), and individual SCP subgroups had distinct clinical outcomes when compared to all other patients, to SCP subgroups of the same clinical classifica-tion, and to other SCP subgroups containing similar cellular metaclusters but different architectures (FIGS. 12 and 13, FIGS. 17 and 18).

Figure 13:
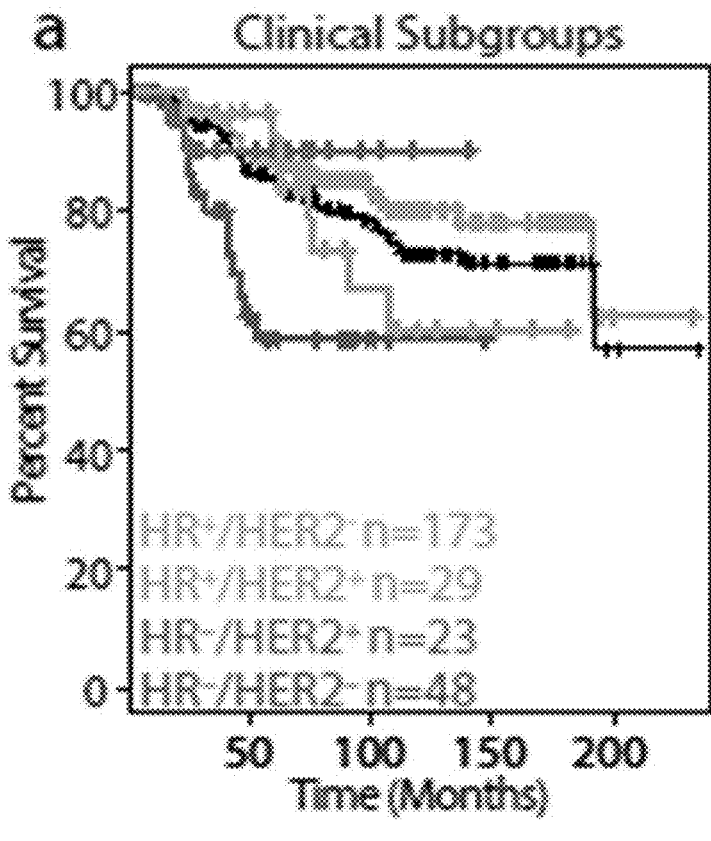
FIG. 13 shows SCP groups have distinct clinical outcomes. Kaplan-Meier curves show the overall survival for each patient group (n=278 patients total) based on (a) clinical subgroups, (b) clinical grade, (c-f) SCP subgroup. Two-sided log rank test ⊗ p<0.05 compared to all other samples, ★p<0.05 compared to similar subgroups, ★p<0.05 compared to other HR+/HER2− patients.
Figure 13:
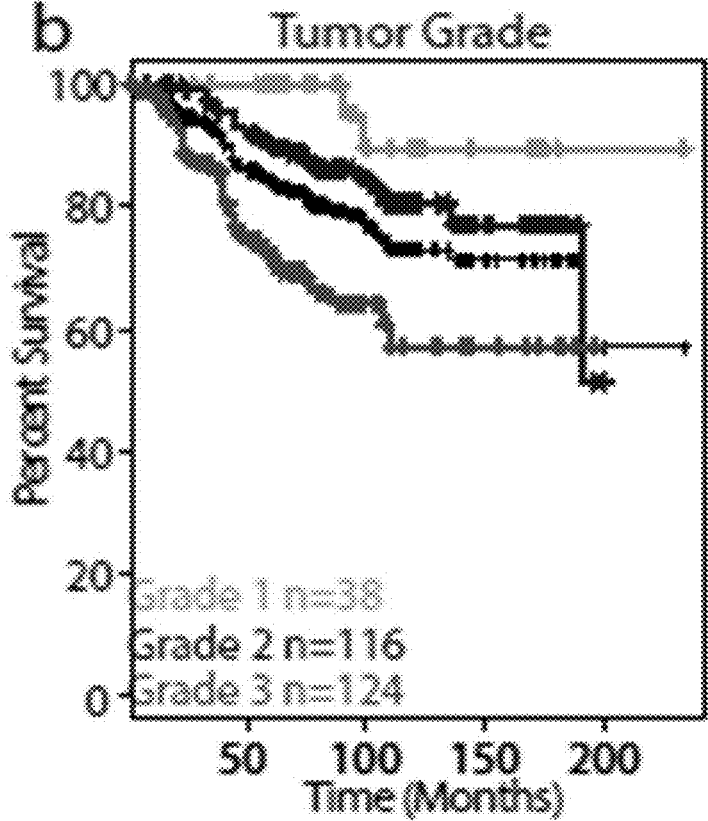
Figure 13:
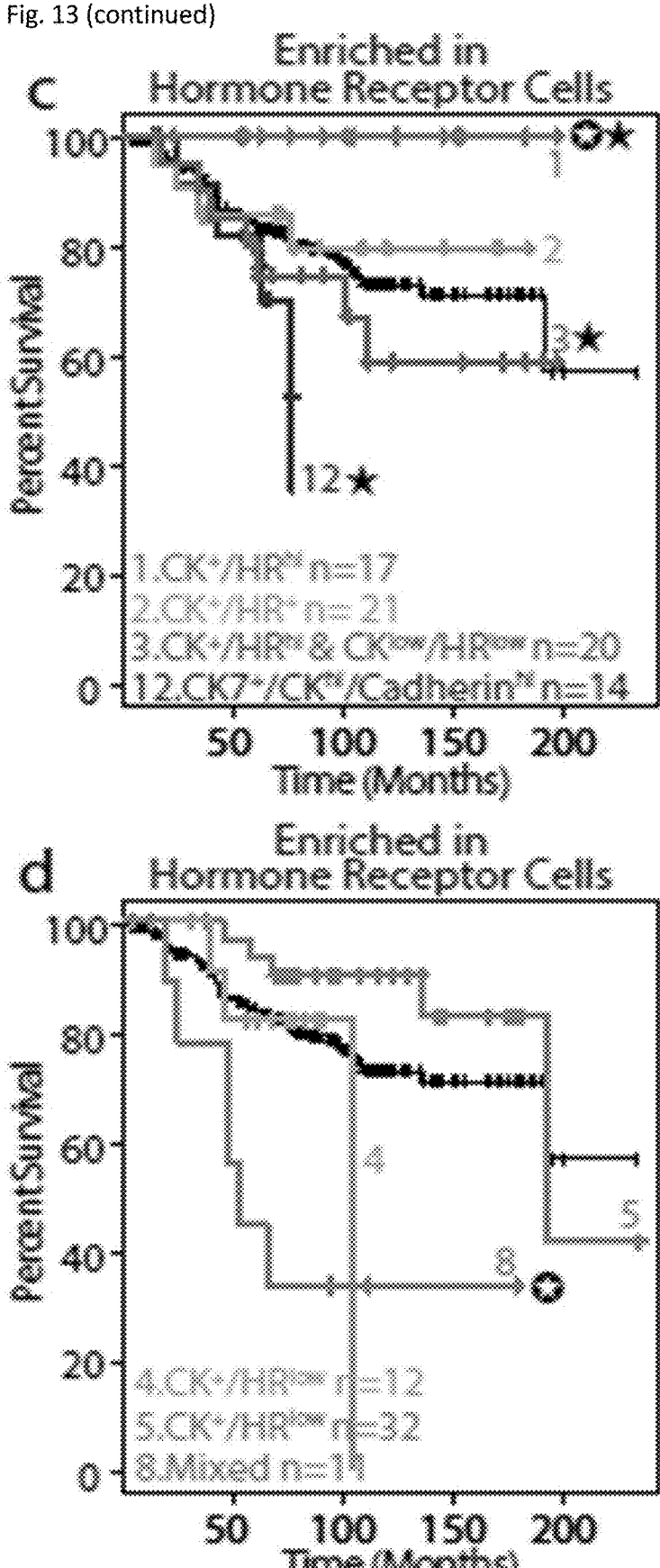
Figure 13:
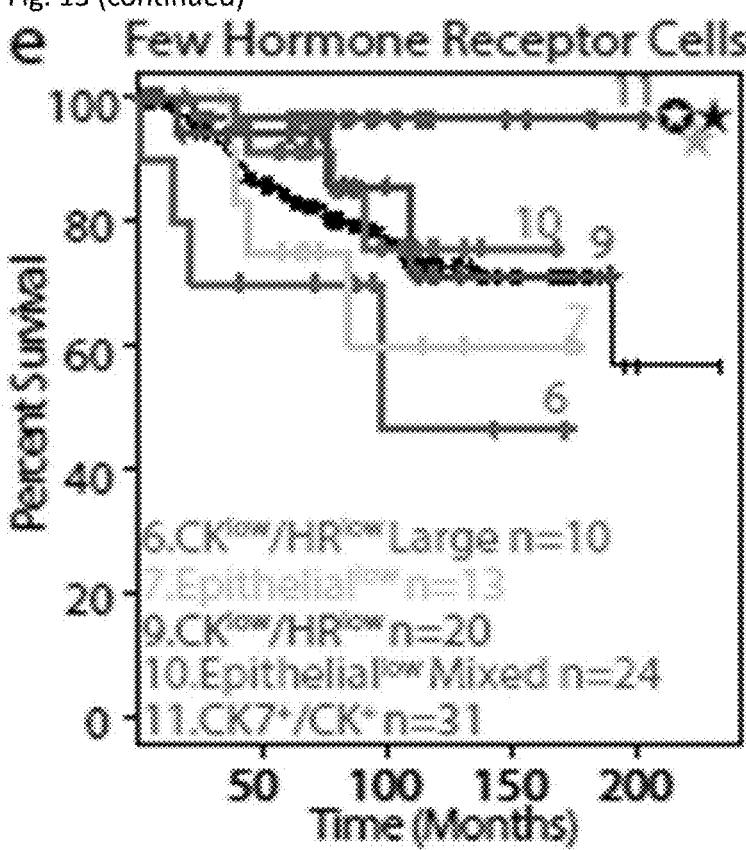
Figure 13:
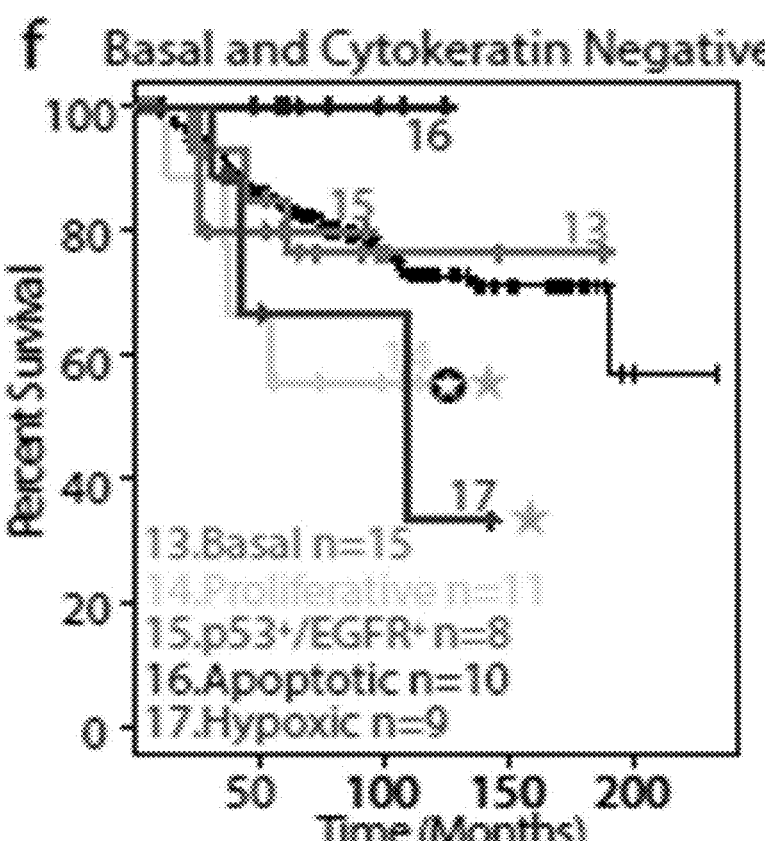
Figure 14:
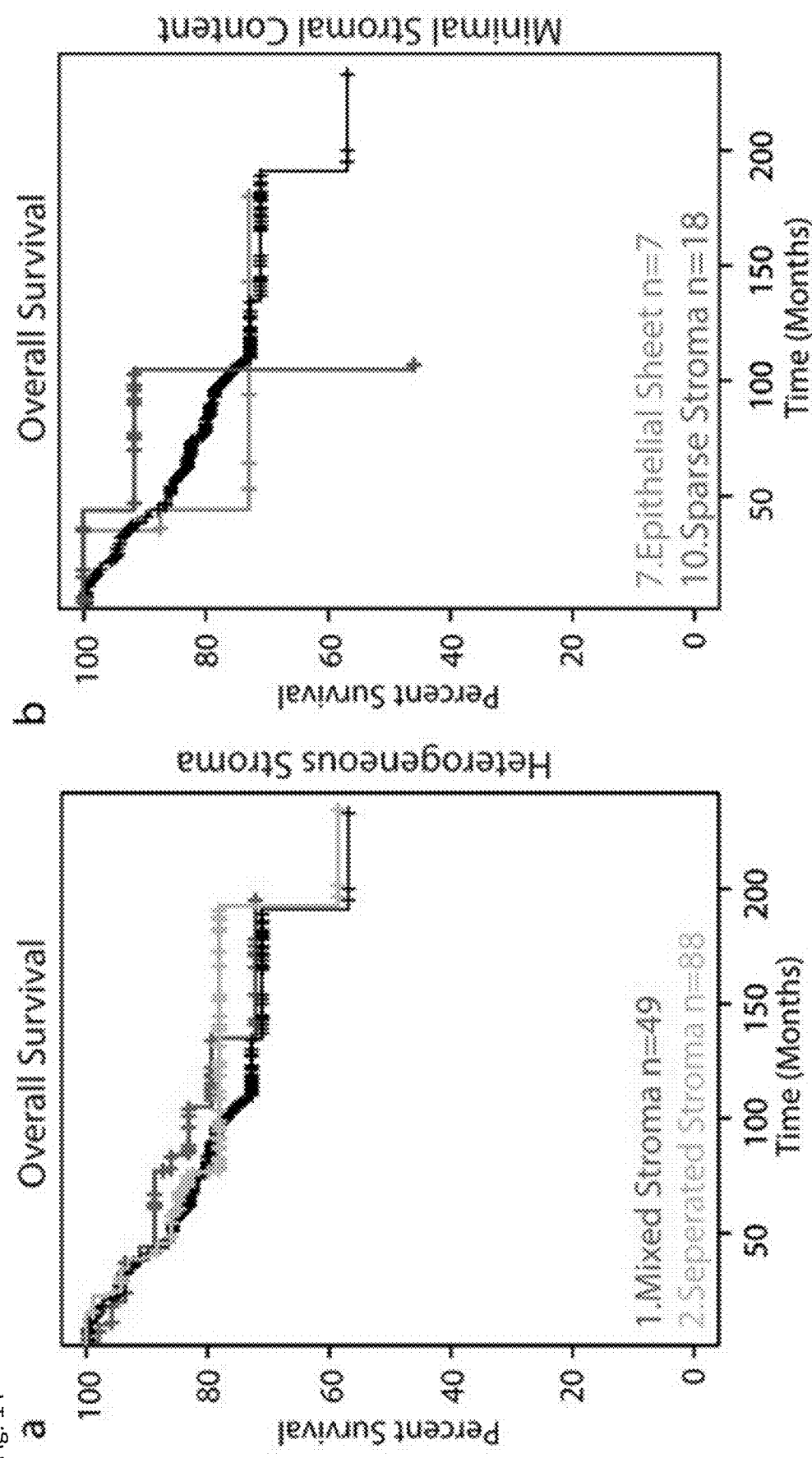
FIG. 14 shows Kaplan-Meier survival curves for overall and disease-free survival. Kaplan-Meier survival curves of (a-b) overall survival for certain stromal environments and (c-l) disease-free survival for each patient group based on (c) clinical subtype. (d) grade, (e-h) SCP subgroup, and (i-l) stromal environment. Two-sided log rank test ⊗ p<0.05 compared to all other samples.
Figure 14:
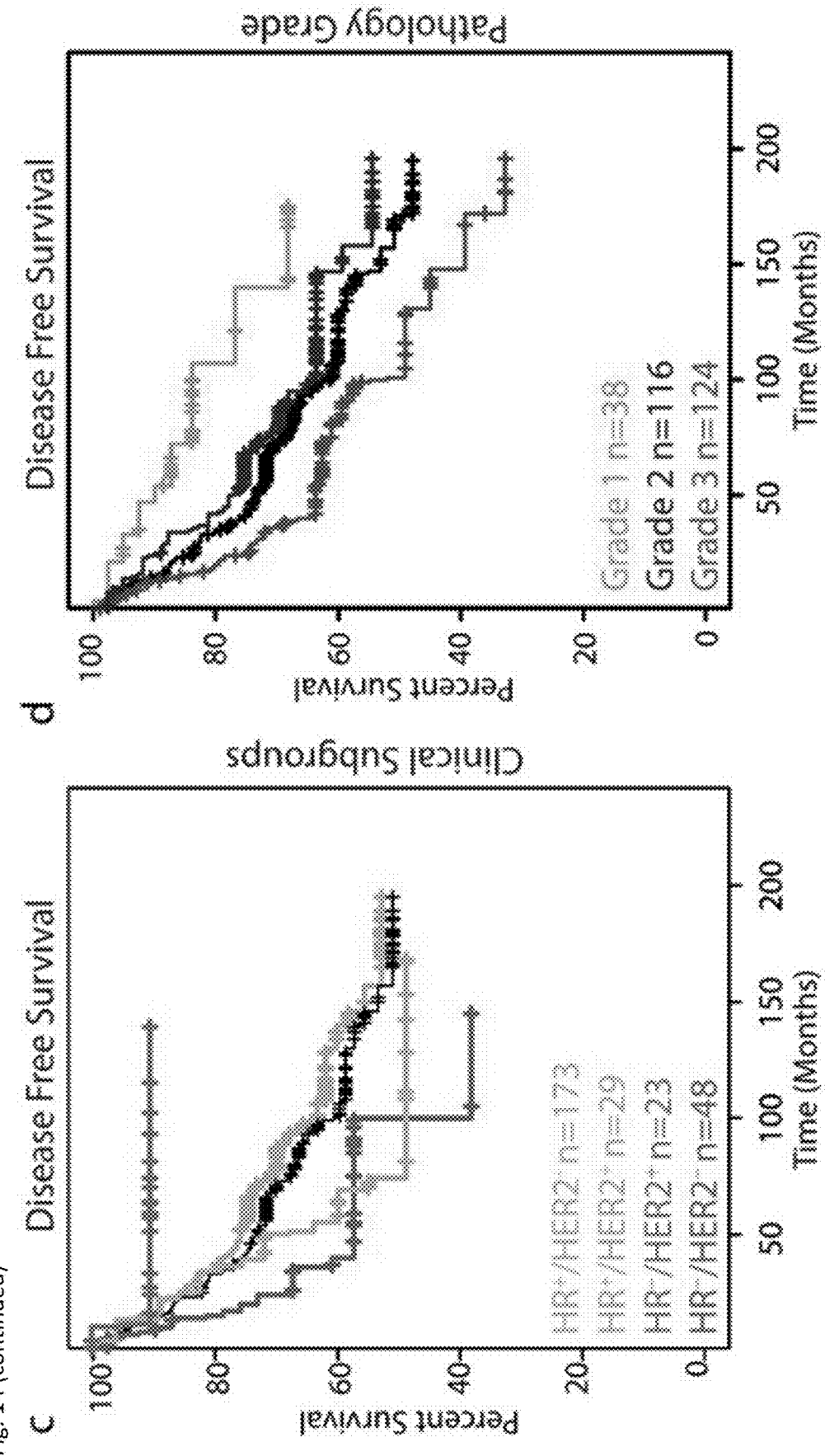
Figure 14:
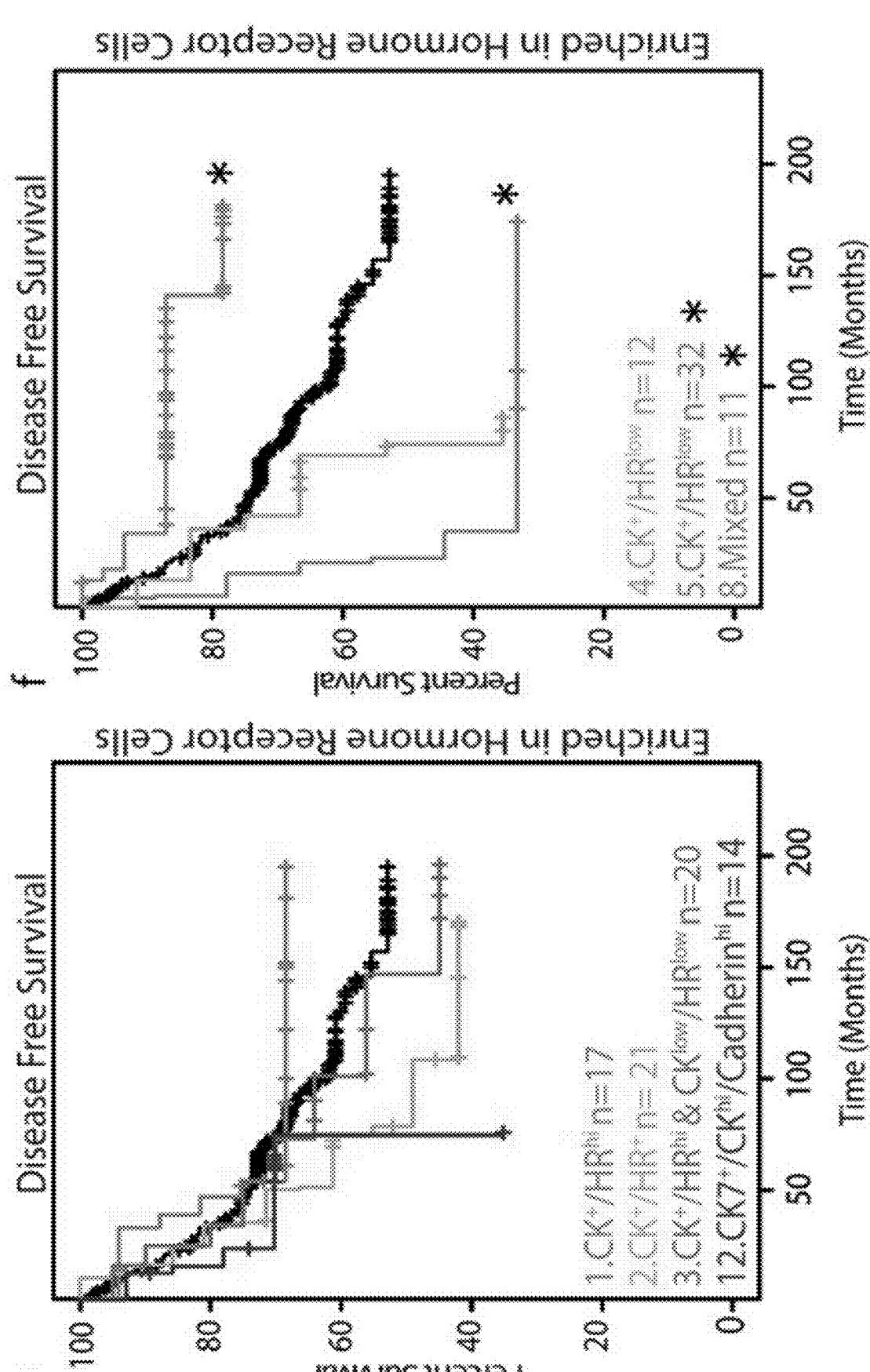
Figure 14:
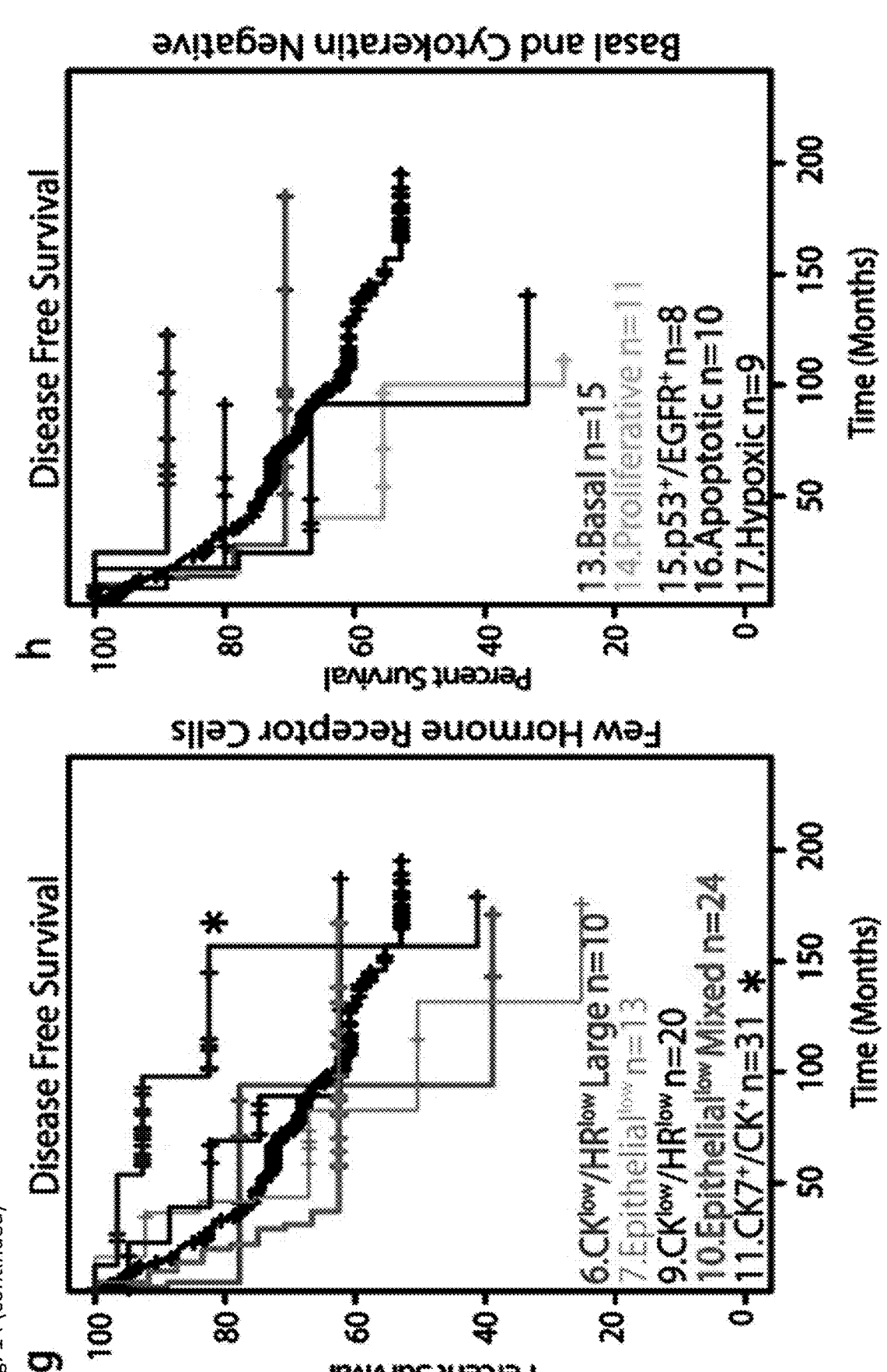
Figure 14:
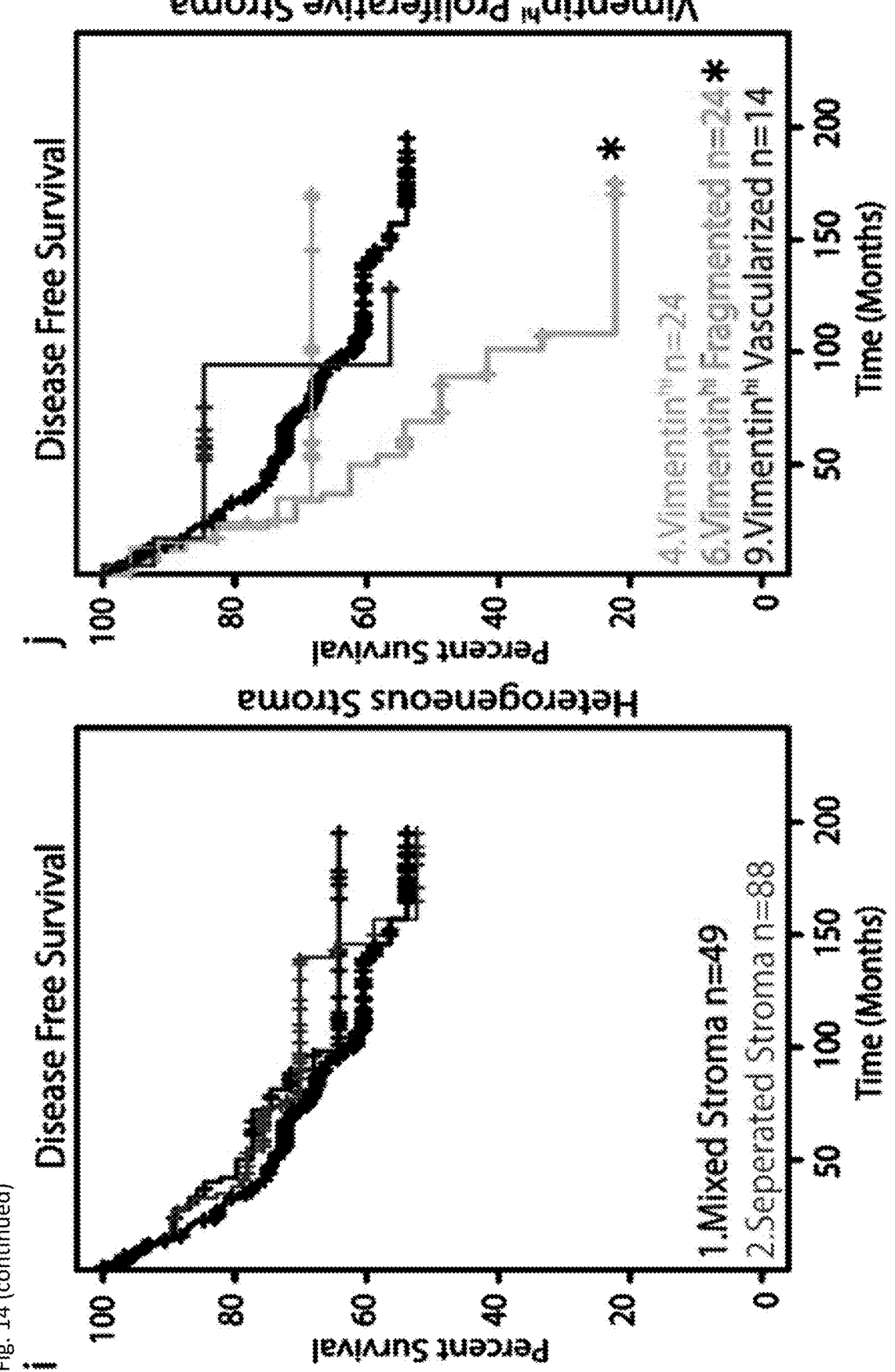
Figure 14:
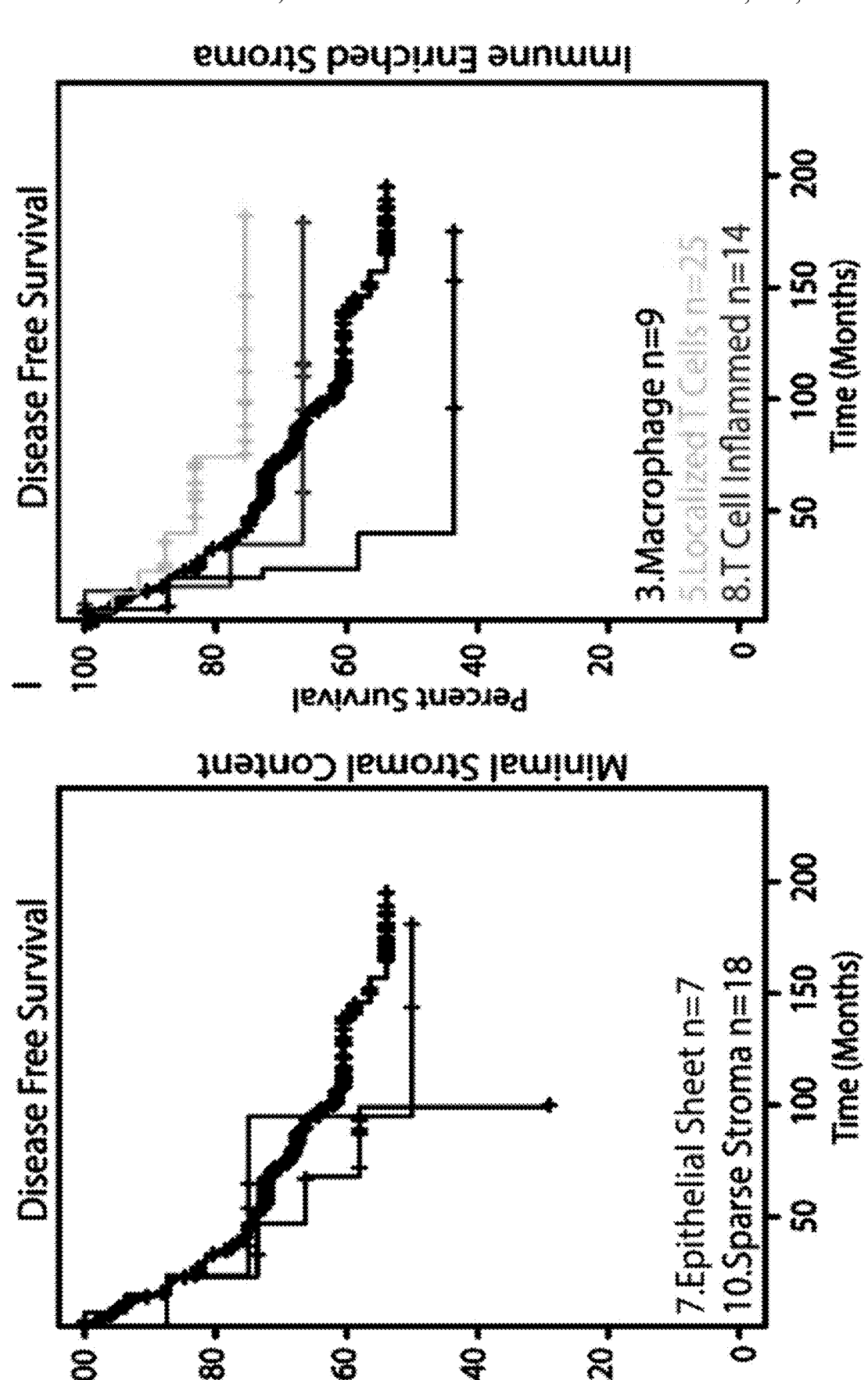

$HR^+$ clinically defined tumours were divided into those strongly enriched in cells with high expression of hormone receptors (SCPs 1-5 and 12) and tumours with few $HR^{hi/+}$ cells surrounded by many cells that expressed only low levels or lacked HRs (SCPs 6-10 and 11) that are currently not clinically classified (FIGS. 11$a$, 7, and 12). SCP 1, which contained predominantly metacluster 23 ($CK^+/HR^{hi}$ tumour cells), was only associated with patients who did not suc-cumb to disease. Conversely, SCP 3, which contains the same cellular metaclusters but differs in structure, with smaller communities and relatively higher proportions of $CK^{low}/HR^{low}$ metacluster 22 and 25 cells, was associated with poor prognosis, as were SCPs 6 and 9, which involve predominantly $CK^{low}/HR^{low}$ cells (FIGS. 11$a$, 13$c$, 13$e$, and 14). SCP 2, containing $CK^+/HR^+$ cells, was significantly enriched in the $HR^+/HER2^+$ clinical subtype, which was otherwise dominated by $CK^{low}/HR^{low}$ metacluster 22 (FIGS. 11$a$, 7, and 12). SCPs 11 and 12 were characterized by $CK7^+$ cells primarily from metaclusters 20 and 19, respectively. SCP 11 overlapped with the clinically assigned $HR^-/HER2^+$ tumour type, and, although this clinical subtype usually has poor outcomeshttp://f1000.com/work/citation?ids=4444468,5733680&pre=&pre=&suf=&suf=&sa=0,0 (Coates, A. S., et aL. *Ann, Oncol.* 26, 1533-1546 (2015), SCP 11 patients had significantly better outcomes than other patients in this cohort. In contrast, the small number of CK7$^+$ SCP 12 patients, predominantly clinically assigned as HR$^+$/HER2$^-$, did not survive long term (FIG. 11*a*, 12, 13*a*, 13*c*, 13*e*, and 14). Tumours from patients with high-risk TNBC contained distinct cell types including cells with cytokeratin expression suggestive of a luminal, not myoepithelial, cell of origin (FIGS. 4, 5, 11*a*, and 12). TNBC phenotypes without luminal epithelial markers and with high levels of hypoxic, p53$^+$/EGFR$^+$, basal, or proliferative markers distinguished SCPs 13, 14, 15, and 17 with poor outcome (FIGS. 4, 5, 11*a*, and 13). SCP 16 tumours were p53$^+$ and expressed apoptotic markers, and interestingly, patients with tumours of this group did not succumb to disease even though they were clinically classified as TNBC (FIGS. 13, and 14*f*).

By mapping the cellular spatial organization of these tumours, variable structures and cellular densities, and relationships between cellular phenotype and tissue organization were observed (FIG. 11). Heterogeneous tumours consisted of multiple phenotypically pure communities indicated by many bands on the heatmap, whereas homogeneous tumours organized in one epithelial sheet or with similar communities of different sizes have only a few clustered bands (FIG. 11*b*). Most tumours were dominated by a single tumour-cell metacluster and few community types, but tumours in SCP 8 and some in SCP 10 were unusually heterogeneous, consisting of multiple epithelial cellular metaclusters at similar proportions localized to spatially distinct communities (FIG. 11*b*). Patients in SCP8 with these heterogeneous tumours had very poor outcomes. Overall, intra-tumour phenotypic heterogeneity was spatially segregated into separate tumour communities as opposed to heterogeneous tumour masses, and patients with tumours with greater spatio-phenotypic heterogeneity had poorer outcomes.

Figure 15:
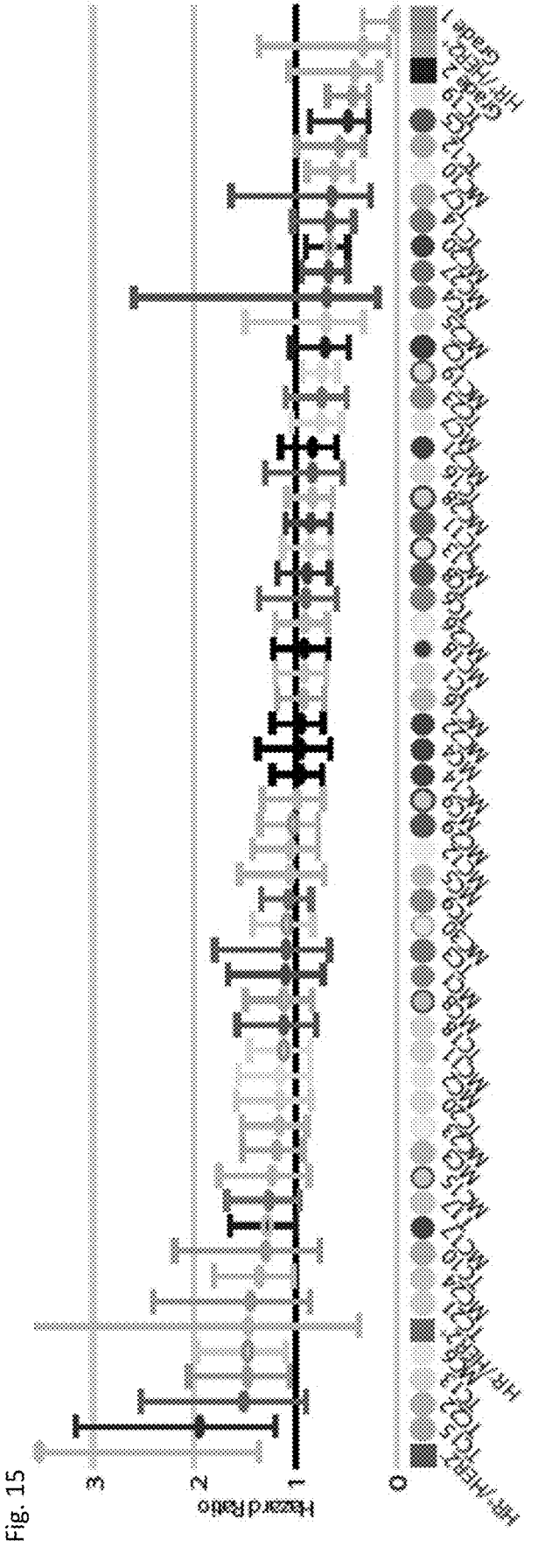
FIG. 15 shows that spatially defined cell communities are associated with patient outcome. Graph showing the relative hazard ratios and 95% confidence intervals of disease-specific overall survival for densities of tumour (T) and microenvironment (ME) cellular communities and clinical categories (molecular subtype and grade) estimated by Cox proportional hazards model (n=266 patients, n=15 patients only containing communities <10 cells were excluded).

Compared to clinically defined subtypes, SCP grouping improved the ability to predict a patient's overall survival using Cox proportional hazards modelling (FIG. 18). In order to identify features associated with patient risk not captured by clinical grading and classification, the epithelial and stromal single-cell and community contributions to the model were investigated. Almost no single-cell phenotypes or cellular metaclusters were independently associated with outcome (not shown); however, spatially defined cell communities were (FIG. 15). For certain cell types, large tumour cell communities were related to better outcome, whereas similar networks of small size were related to poor outcome (FIG. 9, 15, TCs 12 vs. 13, 17 vs. 23, 5 vs. 15). In addition, the microenvironment community MC 6, characterized by vascularization with T cell involvement, was significantly associated with increased risk of death even though it was more commonly found in the low-risk HR$^+$ clinical subgroups than other subgroups (FIG. 10, 15). In contrast, highly T cell infiltrated MC 19 and macrophage-enriched MC 27 were significantly associated with better patient outcomes even though inflammation is more common in high-risk TNBC tumours than other clinical subgroups (FIG. 10, 15). SCP-defined tumour types and tumour and stromal architectures informed prognosis beyond current clinical classifications. Tumour morphology, drug sensitivity, drug resistance, assignment of significantly high or low risk, or exclusion from significantly high or low risk, are all potentially useful information derived from SCP in a clinical context. This information has been summarised in FIG. 19.

In summary, the present invention allows a systematic, multidimensional interrogation of breast cancer histology to generate a detailed spatial map of single-cell phenotypes and cellular communities related to disease. This single-cell pathology allows better segregation of patients with distinct clinical outcomes than clinical subtyping strategy currently available in the art. The examples herein show how analysis of multi-cellular structures revealed that phenotypic heterogeneity in tumours was spatially localized to distinct regions or lesions. Moreover, the multi-cellular structures yielded patient outcome-relevant information superior to single-cell data alone. Co-occurring breast cancer phenotypes were identified, and phenotypic and spatial heterogeneity varied between clinically established subtypes. Therefore, multi-cellular spatial information is medically relevant and provides a basis for how spatial and phenotypic tissue features can influence patient disease progression.

We claim:

1. A method of treating a cancer in a patient comprising:
   a. acquiring data recorded from a labelled cancer tissue sample with local resolution of a single cell via imaging mass cytometry at a subcellular resolution of ≤5 μm, wherein
      the labelled cancer tissue sample is labelled with a plurality of molecular probes, each probe being specific for a biomolecule,
      each of said molecular probes is characterized by a detectable marker,
      a signal of the detectable marker correlates with an amount of expression of the biomolecule, and
      the biomolecules are selected from a list comprising:
         i. epithelial cadherin (E-cadherin),
         ii. cytokeratin (CK) 18 and/or 19,
         iii. CK7,
         iv. oestrogen receptor (ER) and/or progesterone receptor (PR),
         v. a marker of cellular proliferation,
         vi. CK5 and/or p63 and/or CK14,
         vii. p53,
         viii. a hormone receptor (HR),
         ix. a marker of apoptosis,
         x. epidermal growth factor receptor (EGFR),
         xi. a marker of hypoxia, and
         xii. a marker of DNA content,
   b. evaluating and processing the data such as to assign each detectable marker to an expression group selected from a high (hi), a positive (+), a low ($^{lo}$), or a negative (−) expression level of the detectable marker in each cell comprised in the labelled cancer tissue sample;
   c. assigning each cell a cellular identity (CI), based on the assigned expression group, wherein the CI for each cell is selected from:
      CI1: CIAX$^{hi}$, EGFR−, (ER and/or PR)+, (CK5 and/or p63 and/or CK14)+;
      CI2, p53$^{hi}$, (cC3 and/or cPARP)+, (ER and/or PR)−, (CK18 and/or CK19)−, (CK5 and/or p63 and/or CK14)−;
      CI3, (Ki-67 and/or PCNA)+, CK7−, (CK18 and/or CK19)−, (ER and/or PR)−, (CK5 and/or p63 and/or CK14)−;
      CI4, p53$^{hi}$, EGFR+, CIAX$^{hi}$, (ER and/or PR)−, (CK5 and/or p63 and/or CK14)−;
      CI5, (CK5 and/or p63 and/or CK14)+, CK7−, (CK18 and/or CK19)−, (ER and/or PR)−;

CI6, E-cadherin$^{hi}$, (CK18 and/or CK19)$^{hi}$, CK7+, (ER and/or PR)+, (CK5 and/or p63 and/or CK14)–;

CI7, CK7+, (CK18 and/or CK19)+, (ER and/or PR)–, (CK5 and/or p63 and/or CK14)–;

CI8, E-cadherin-, CK7–, (CK18 and/or CK19)–, (CK5 and/or p63 and/or CK14)–, (ER and/or PR)–;

CI9, (E-cadherin$^{lo}$ or E-cadherin-), ((CK18 and/or CK19)– or (CK18 and/or CK19)$^{lo}$), (ER and/or PR) 10, (CK5 and/or p63 and/or CK14)–;

CI10, ((CK18 and/or CK19)$^{hi}$ or (CK18 and/or CK19)+), E-cadherin+, (ER and/or PR)$^{hi}$, CK5 and/or p63 and/or CK14)–;

CI11, ((CK18 and/or CK19)$^{hi}$ or (CK18 and/or CK19)+), E-cadherin+, (ER and/or PR)+, CK5 and/or p63 and/or CK14)–;

CI12, (E-cadherin$^{lo}$ or E-cadherin+), ((ER and/or PR) 1° or (ER and/or PR)–), (CK5 and/or p63 and/or CK14)–;

CI13, p53$^{hi}$, EGFR+, (ER and/or PR)$^{hi}$, ((CK5 and/or p63 and/or CK14)$^{lo}$ and/or (CK5 and/or p63 and/or CK14)–);

CI14, CK7+, (CK18 and/or CK19)+, (CK5 and/or p63 and/or CK14)+, (ER and/or PR)–;

d. assigning said cancer tissue sample to a single cell pathology (SCP) patient group according to the proportion of each cellular identity assigned in the cell assignment step the sample contains, wherein the list of SCP patient groups comprises or consists of:

SCP1. >70% of single cells are CI10;

SCP2. >70% of single cells are CI11;

SCP3. ≤70% of single cells are CI10;

SCP4. >70% of single cells to CI12;

SCP5. ≤70% of single cells are CI12;

SCP6. >80% of single cells are CI9;

SCP7. >80% of single cells are CI8;

SCP8. ≤70% of single cells are CI9; or CI10, or CI12;

SCP9. >60% of single cells are CI9;

SCP10. >70% of single cells are CI9; CI10, or CI12;

SCP11. >60% of single cells are CI7;

SCP12. >70% of single cells are CI6;

SCP13. >50% of single cells are CI5;

SCP14. >60% of single cells are CI3;

SCP15. >70% of single cells are CI4;

SCP16. >50% of single cells are CI2;

SCP17. >50% of single cells are CI1;

SCP18. >90% of single cells are CI14;

wherein the patient is assigned to a probable outcome group according to the sample's SCP classification:

SCP1, likely good outcome, and likely sensitive to
   a selective oestrogen receptor modulator (SERM) antineoplastic drug;
   a selective estrogen receptor degraders (SERD) antineoplastic drug;
   an aromatase inhibitor antineoplastic drug; and/or
   a PI3K pathway inhibitor drug;

SCP2, likely sensitive to
   an antiangiogenic antineoplastic drug; and/or
   a HER2 targeting antineoplastic drug;

SCP3, likely poor outcome, likely sensitive to
   an anthracycline-type antineoplastic drug;
   a mitotic inhibitor-type antineoplastic drug;
   an antineoplastic platinum complex;
   an alkylating antineoplastic drug;
   an antimetabolite-type antineoplastic drug;
   a selective SERM antineoplastic drug;

a SERD antineoplastic drug;
   an aromatase inhibitor drug; and/or
   a PI3K pathway inhibitor drug;

SCP4, likely lack of sensitivity to antineoplastic drugs which target ER

SCP5, likely sensitive to
   an EZH2 methyltransferase inhibitor antineoplastic drug;

SCP6, likely poor outcome, likely sensitive
   a HER2 targeting antineoplastic drug;

SCP7, likely lack of sensitivity to
   an antiangiogenic antineoplastic drug,
   and likely sensitive to
   a HER2 targeting antineoplastic drug;

SCP8, likely bad outcome;

SCP9, likely sensitive to
   a HER2 targeting antineoplastic drug;

SCP10, likely sensitive to
   a HER2 targeting antineoplastic drug;

SCP11: likely good outcome, and likely sensitive to
   a HER2 targeting antineoplastic drug, and/or
   a PI3K pathway inhibitor drug a PI3K pathway inhibitor drug;

SCP12: likely poor outcome, likely sensitive to
   an EZH2 methyltransferase inhibitor antineoplastic drug;

SCP13: likely sensitive to
   a HER2 targeting antineoplastic drug;

SCP14: likely bad outcome, and likely sensitive to
   an anthracycline-type antineoplastic drug;
   a mitotic inhibitor-type antineoplastic drug;
   an antineoplastic platinum complex;
   an alkylating antineoplastic drug; and/or
   an antimetabolite-type antineoplastic drug;

SCP15: likely sensitive to
   an anthracycline-type antineoplastic drug;
   a mitotic inhibitor-type antineoplastic drug;
   an antineoplastic platinum complex;
   an alkylating antineoplastic drug;
   an antimetabolite-type antineoplastic drug; and/or
   an inhibitor of EGFR bioactivity antineoplastic drug;

SCP16: likely good outcome, likely sensitive to
   an anthracycline-type antineoplastic drug;
   a mitotic inhibitor-type antineoplastic drug;
   an antineoplastic platinum complex;
   an alkylating antineoplastic drug; or
   an antimetabolite-type antineoplastic drug;

SCP17: likely bad outcome, and likely sensitive to
   a quinone-alkylating antineoplastic drug;

SCP18: likely lack of sensitivity to antineoplastic drugs which target ER, and likely sensitive to a
   a PI3K pathway inhibitor drug;

e. administering to the patient an effective amount of a pharmaceutical composition comprising a drug or complex selected from the drugs and complexes to which the SCP is sensitive.

2. The method of claim 1, wherein the SCP is selected from SCP3, SCP14, SCP15, and SCP16; and the drug or complex is selected from
an anthracycline-type antineoplastic drug; or
a mitotic inhibitor-type antineoplastic drug; or
an antineoplastic platinum complex; or
an alkylating antineoplastic drug; or
an antimetabolite-type antineoplastic drug.

3. The method of claim 1, wherein the SCP is SCP1 or SCP3, and the drug or complex is selected from a selective estrogen receptor modulator (SERM) antineoplastic drug;

a selective estrogen receptor degraders (SERD) antineoplastic drug; and/or an aromatase inhibitor antineoplastic drug.

4. The method of claim 1, wherein the SCP is SCP2, and the drug or complex is an antiangiogenic antineoplastic drug.

5. The method of claim 1, wherein the SCP is SCP5 or SCP12, and the drug or complex is an EZH2 methyltransferase inhibitor antineoplastic drug.

6. The method of claim 1, wherein the SCP is SCP15, and the drug or complex is an inhibitor of EGFR bioactivity antineoplastic drug.

7. The method of claim 1, wherein the SCP is SCP17, and the drug or complex is a quinone-alkylating antineoplastic drug.

8. The method of claim 1, wherein the SCP is selected from SCP2, SCP6, SCP 7, SCP 9, SCP 10, SCP11, and SCP13, and the drug or complex is selected from a HER2 targeting antineoplastic drug.

9. The method of claim 1, wherein the SCP is selected from SCP1, SCP3, SCP11, and SCP18, and the drug or complex is selected from PI3K pathway inhibitors.

10. The method according to claim 1, wherein the method of obtaining information about the average expression of said plurality of biomolecules comprises constructing an image of the tissue sample.

11. The method according to claim 1, wherein the method of obtaining information about the average expression of said plurality of biomolecules is imaging mass cytometry at a subcellular resolution of ≤5 μm.

12. The method according to claim 1, wherein said method further comprises the steps of:

in step a., including additional markers selected from:
  xiii. CD3 or CD90;
  xiv. CD20 or CD19;
  xiv. CD68;
  XV. CD44 and/or CD45;
  xvi. Fibronectin;
  xvii. vimentin, and
  xviii. CD31 and/or von Willibrand factor (vWF) and/or CD34; and
in step c., including additional cellular identities selected from:
  CI15. CD44+, CD45+, (CD3 or CD90)+, fibronectin-, E-cadherin-, ((CK5 and/or p63 and/or CK14) 1° or (CK5 and/or p63 and/or CK14)−);
  CI16. CD20+, (fibronectin$^{lo}$ or fibronectin-), ((E-cadherin$^{lo}$ or E-cadherin-), ((CK5 and/or p63 and/or CK14) 1° or (CK5 and/or p63 and/or CK14)−);
  CI17. (CD3 or CD90)+, (CD20 or CD19)+;

CI18. CD68+;
CI19. vimentin+, (CD34 and/or VWF and/or CD31)+;
CI20. vimentin-, (fibronectin+ or fibronectin$^{hi}$), (CD3 or CD90)−, (CD20 or CD19)−, CD45−, CD44−.

13. The method according to claim 11, wherein the single cell is a fragment of the image of the tissue sample.

14. The method according to claim 12 wherein said method further comprises the steps of:

in a cellular community detection step, partitioning the image of the tissue sample into multicellular regions, wherein each single cell inside the multicellular region is highly interconnected to neighbouring cells to provide a cellular community;

in a cellular community assignment step, assigning a cellular community identity (CCI) to each cellular community according to the number of cells in the cellular community, and the proportion of each CI it contains, wherein the list of CCI comprises or consists of:

CCI1. Among cells with identities CI1-CI14, >10% of single cells are CI6, and the average size of cellular communities is >25 cells; or CCI2. Among cells with identities CI1-CI14, >10% of single cells are CI6, and the average size of cellular communities is ≤25 cells; or CCI3. Among cells with identities CI1-CI14, >10% of single cells are CI2, and the average size of cellular communities is >25 cells, or CCI4. Among cells with identities CI1-CI14, >10% of single cells are CI2, and the average size of cellular communities is ≤25 cells, or CCI5. Among cells with identities CI1-CI14, >10% of cells are CI3, and the average size of cellular communities is ≤25 cells, or CCI6. >5% of all cells are CI19, and >10% of cells are CI20, and >3% cells are CI18, and the average size of cellular communities is <50 cells, or CCI7. >80% of all cells are any of the identities CI1 to CI15, and <10% are CI20, and the average size of the cellular communities is <75 cells, or CCI8. >20% of all cells are CI15, and/or 16 and/or CI17, and <40% cells are any of the identities CI1 to CI14, and the average size of the cellular communities is more than 75 cells, or CCI9. >5% of all cells are CI18, and the average size of the cellular communities is >25%, or CCI10 >80% of all cells are any of the identities CI1 to CI14, and <2% cells are CI20, and the average size of the cellular communities is >115 cells and <125 cells, wherein the patient is assigned to a probable outcome group according to the CCI classification:

CCI1, CCI3, CCI5, CCI8, CCI9, or CCI10: likely good outcome, and

CCI2, CCI4, CCI6, or CCI7: likely bad outcome.

\* \* \* \* \*